(12) United States Patent
Yuasa et al.

(10) Patent No.: US 10,941,169 B2
(45) Date of Patent: Mar. 9, 2021

(54) CRYSTAL OF CYCLIC PHOSPHONIC ACID SODIUM SALT AND METHOD FOR MANUFACTURING SAME

(71) Applicant: OTSUKA CHEMICAL CO., LTD., Osaka (JP)

(72) Inventors: Hiroaki Yuasa, Tokushima (JP); Hiroki Okazaki, Tokushima (JP)

(73) Assignee: OTSUKA CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/878,109

(22) Filed: May 19, 2020

(65) Prior Publication Data

US 2020/0277318 A1 Sep. 3, 2020

Related U.S. Application Data

(62) Division of application No. 16/460,332, filed on Jul. 2, 2019, now Pat. No. 10,774,100, which is a division of application No. 15/872,321, filed on Jan. 16, 2018, now Pat. No. 10,385,081, which is a division of application No. 15/501,525, filed as application No. PCT/JP2015/072825 on Aug. 12, 2015, now Pat. No. 9,908,909.

(30) Foreign Application Priority Data

Aug. 12, 2014 (JP) .............................. JP2014-164423

(51) Int. Cl.
| | |
|---|---|
| *C07F 9/6571* | (2006.01) |
| *A61P 19/00* | (2006.01) |
| *A61P 29/00* | (2006.01) |
| *A61P 35/00* | (2006.01) |
| *C07F 9/6574* | (2006.01) |
| *A61K 31/665* | (2006.01) |

(52) U.S. Cl.
CPC ........ *C07F 9/657163* (2013.01); *A61P 19/00* (2018.01); *A61P 29/00* (2018.01); *A61P 35/00* (2018.01); *C07F 9/65742* (2013.01); *C07F 9/657181* (2013.01); *A61K 31/665* (2013.01); *C07B 2200/13* (2013.01)

(58) Field of Classification Search
CPC ................................................ C07F 9/657163
See application file for complete search history.

(56) References Cited

U.S. PATENT DOCUMENTS

| | | | |
|---|---|---|---|
| 7,550,449 B2 | 6/2009 | Murofushi | |
| 9,040,602 B2 | 5/2015 | Moszner | |
| 9,085,593 B2 | 7/2015 | Murofushi | |
| 9,908,909 B2 | 3/2018 | Yuasa | |
| 10,385,081 B2 | 8/2019 | Yuasa | |
| 10,774,100 B2 * | 9/2020 | Yuasa | .............. C07F 9/657163 |
| 2006/0122155 A1 | 6/2006 | Murofushi | |
| 2009/0326256 A1 | 12/2009 | Murofushi | |
| 2014/0309194 A1 | 10/2014 | Murofushi | |

FOREIGN PATENT DOCUMENTS

| | | |
|---|---|---|
| CN | 101143880 A | 3/2008 |
| EP | 1402894 A1 | 3/2004 |
| JP | H06-228169 | 8/1994 |
| JP | 2004-010582 A1 | 1/2004 |
| JP | 5077893 B2 | 11/2012 |
| WO | 03/104246 A1 | 12/2003 |
| WO | 2011/065480 A1 | 6/2011 |
| WO | 2013/069404 A1 | 5/2013 |

OTHER PUBLICATIONS

E. Nozaki, et al.; "Synthesis of enantiopure 2-carba-cyclic phosphatic acid and effects of its chirality on biological functions"; Biochimica et Biophysica Acta; vol. 1811; 2011; pp. 271-277 (7 sheets)/ Cited in International Search Report.
A. Uchiyama, et al.; "Inhibition of transcellular tumor cell migration and metastasis by novel carba-derivatives of cyclic phosphatidic acid"; Biochimica et Biophysica Acta; vol. 1711; 2007; pp. 103-112 (10 sheets)/ Cited in International Search Report/ p. 3 of Specification.
Yuki Kagobutsu Kessho Sakusei Handbook; Jul. 25, 2008; pp. 17-23, pp. 37-40, pp. 45-51, pp. 57-65 and translation (54 sheets total)/ p. 3 of Specification.
J. Dubois, et al.; "Synthesis of 5,5'-Dihydroxyleucine and 4-Fluoro 5,5'-Dihydroxyleucine, the Reduction Products of 4-Carboxyglutamic and 4-Carboxy-4-Fluoroglutamic Acids"; Tetrahedron; vol. 47; No. 6; 1991; pp. 1001-1012 (12 sheets)/ p. 3 of Specification.
International Search Report for International Application No. PCT/JP2015/072825 dated Nov. 10, 2015.
Extended European Search Report for European Patent Application No. 18205596.2 dated Aug. 29, 2019 (28 sheets).
K. Lange, et al.; "Enzyme assisted syntheses of chiral building blocks for isosters of diglycerides, phospholipids and PAF"; Tetrahedron Asymmetry; Pergamon Press Ltd; vol. 15; No. 18; Sep. 20, 2004; pp. 2811-2815 (5 pages).
Luo, et al.; "Theory and Practice of Modern Physical Pharmaceuticals"; Apr. 30, 2005; pp. 1-2, pp. 487-490 (10 sheets total, including cover sheet, 1 end sheet, 2 sheets translation).

(Continued)

*Primary Examiner* — Golam M Shameem
(74) *Attorney, Agent, or Firm* — Kratz, Quintos & Hanson, LLP

(57) ABSTRACT

An object of the present invention is to provide crystal of a cyclic phosphonic acid sodium salt (2ccPA) with high purity and excellent storage stability and a method for producing the crystal. The present invention provides a crystal of a cyclic phosphonic acid sodium salt (2ccPA) represented by formula (1):

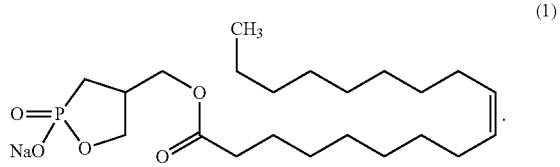

(1)

11 Claims, 27 Drawing Sheets

(56) References Cited

OTHER PUBLICATIONS

Office Action of the Chinese Patent Application No. 201580043025.2 dated Apr. 8, 2018 (8 sheets).
Extended European Search Report for European Patent Application No. 18205589.7 dated Mar. 27, 2019 (11 pages).
Partial European Search Report for European Patent Application No. 18205596.2 dated Apr. 10, 2019 (23 pages).
Office Action of Japanese Patent Application No. 2016-542597: Notification of Reasons for Refusal dated May 7, 2019 (2 pages, 3 pages translation, 5 pages total).
R. Kluger, et al.; "Endocyclic cleavage in the alkaline hydrolysis of the cyclic phosphonate methyl propylphostonate: dianionic intermediates and barriers to pseudorotaton"; Journal of the American Chemical Society; Jul. 1, 1991; vol. 113; No. 15; pp. 5714-5719 (6 pages)/ Cited in Partial European Search Report dated Apr. 10, 2019 for App. No. 18205596.2.
R.Schiller, et al.; "3, 5-Disubstituted pyranone analogues of highly antifungally active furanones: conversion of biological effect from antifungal to cytostatic"; Bioorganic & Medicinal Chemistry Letters; Dec. 1, 2010; vol. 20; No. 24; pp. 7358-7360 (3 pages)/ Cited in partial European Search Report dated Apr. 10, 2019 for App. No. 18205596.2.
R. Gupte, et al.; "Synthesis and pharmacological evaluation of the stereoisomers of 3-carba cyclic-phosphatic acid"; Bioorganic & Medicinal Chemistry Letters; Sep. 2010; vol. 20; No. 24; pp. 7525-7528 (4 sheets).
E. Nozaki, et al.; "Pharmacological evaluation of a novel cyclic phosphatidic acid derivative 3-S-cyclic phosphatidic acid (3-S-cPA)"; Bioorganic & Medicinal Chemistry; Mar., 2012; vol. 20; No. 10; pp. 3196-3210 (6 sheets).
J. Guillory; "Generation of Polymorphs, Hydrates, Solvates, and Amorphous Solids"; Polymorphism in Pharmaceutical Solids; H. Brittain ed.; Jan., 1999; New York, Basel; pp. 183-225 (46 sheets total, including 2 front sheets and 1 end sheet).
Extended European Search Report for counterpart European Patent Application No. 15831290.0 dated Mar. 20, 2018 (16 sheets).

\* cited by examiner

CRYSTAL OF CYCLIC PHOSPHONIC ACID SODIUM SALT AND METHOD FOR MANUFACTURING SAME

TECHNICAL FIELD

The present invention relates to a crystal of a cyclic phosphonic acid sodium salt and a method for producing the crystal.

BACKGROUND ART

The cyclic phosphonic acid sodium salt (a sodium salt of 9-octadecenoic acid (9Z)-(2-hydroxy-2-oxo-2$\lambda^5$-1,2-oxaphosphoran-4-yl)methyl ester) represented by the following formula (1) is a compound, typically referred to as 2ccPA.

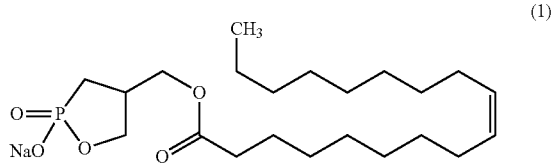

(1)

2ccPA is known to have a potent analgesic action (Patent Literature 1) and is also expected to serve as an anti-cancer agent because of its infiltration-inhibitory activity on cancer cells (Patent Literature 2), an osteoarthritis therapeutic agent because of its accelerated production of hyaluronic acid (Patent Literature 3), or other agents.

2ccPA has traditionally been produced by the production method shown in the following reaction scheme-1 (Patent Literature 2 and 4 and Non-patent Literature 1 and 2).

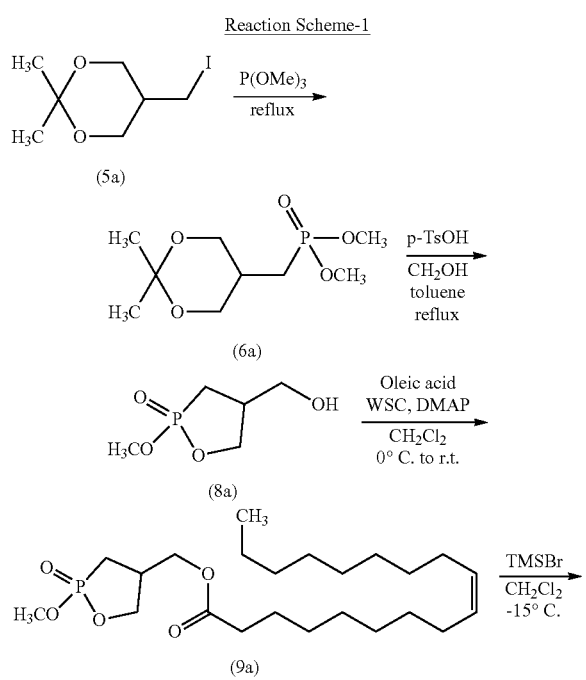

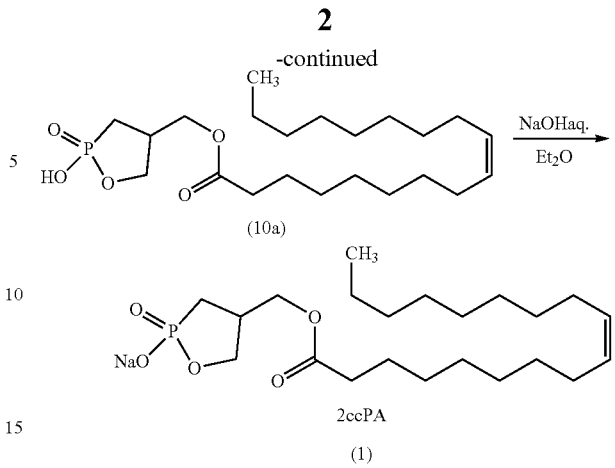

Specifically, iodine compound (5a), which is obtained by the production method disclosed in Non-patent Literature 2, is first reacted with trimethyl phosphite to prepare dimethyl phosphonate (6a). Subsequently, p-toluenesulfonic acid (p-TsOH) is allowed to act on compound (6a) to obtain compound (8a). After oleic acid is introduced to compound (8a) to prepare compound (9a), demethylation is performed, and further a sodium salt is formed, thereby producing 2ccPA.

However, because of the absence of optimization of the reaction conditions for each step and the need for purification by silica gel column chromatography in each step, the total yield of 2ccPA in this production method, obtained by performing the 5 steps described above, is as low as 18.7%, when calculated from the yields disclosed in the literature. This indicates that the method is not suitable for synthesis on a large scale. In addition, the use of bromotrimethylsilane (TMSBr) in the demethylation step generates hydrogen bromide as a by-product, which makes the reaction system strongly acidic, making the product prone to decomposition. In actuality, the yield in the demethylation step is as low as 38%.

In the final step, compound (10a) is formed into a sodium salt using a sodium hydroxide aqueous solution to induce 2ccPA. However, because freeze-drying is performed without purification, strongly basic sodium hydroxide may come to be mixed with the solid of 2ccPA. Thus, decomposition of 2ccPA by sodium hydroxide is unavoidable, causing a storage stability problem.

Therefore, there has been a demand for the development of a method for producing a crystal of 2ccPA that is convenient, and that produces a high-purity crystal exhibiting excellent storage stability at a high yield, as compared with the traditional known method.

CITATION LIST

Patent Literature

Patent Literature 1: U.S. Pat. No. 5,077,893
Patent Literature 2: JP2004-10582
Patent Literature 3: WO2013/069404
Patent Literature 4: WO03/104246

Non-Patent Literature

Non-patent Literature 1: Biochimica et Biophysica Acta, 2007, 1771, pp. 103-112
Non-patent Literature 2: Tetrahedron, 1991, Vol. 47, No. 6, pp. 1001-1012

SUMMARY OF INVENTION

Technical Problem

An object of the present invention is to provide a crystal of 2ccPA with high purity and excellent storage stability.

Another object of the invention is to provide a method for producing the crystal of 2ccPA that is convenient and that produces the crystal at a high yield.

Solution to Problem

The present inventors conducted extensive research to achieve the objects, and produced at a high yield a cyclic phosphonic acid ester, which is a precursor of 2ccPA, performing only one-time purification by silica gel column chromatography, and successfully induced 2ccPA from the cyclic phosphonic acid ester without using a strong acid or strong base.

In addition, the inventors found that the thus-produced crystal of 2ccPA is excellent in storage stability and can achieve the objects. The present invention was completed on the basis of these findings.

Specifically, the present invention provides the following crystal of 2ccPA and the method for producing the crystal.

Item 1. A crystal of a cyclic phosphonic acid sodium salt (2ccPA) represented by formula (1):

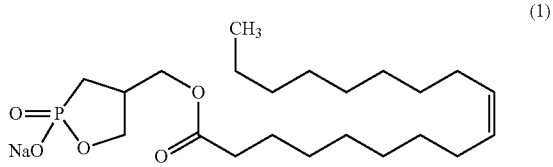

Item 2. The crystal according to Item 1, having an X-ray powder diffraction spectrum comprising a characteristic peak expressed in degrees 2θ at 15° to 17°.

Item 3. The crystal according to Item 1 or 2, having an X-ray powder diffraction spectrum comprising a characteristic peak expressed in degrees 2θ at 9° to 10°.

Item 4. The crystal according to any one of Items 1 to 3, having an X-ray powder diffraction spectrum comprising characteristic peaks expressed in degrees 2θ at 3° to 5°.

Item 5. The crystal according to Item 4, having an X-ray powder diffraction spectrum comprising characteristic peaks expressed in degrees 2θ at 4.7° to 5.0°.

Item 6. The crystal according to Item 4, having an X-ray powder diffraction spectrum comprising a characteristic peak expressed in degrees 2θ at 4.4° to 4.6°.

Item 7. The crystal according to Item 4, having an X-ray powder diffraction spectrum comprising a characteristic peak expressed in degrees 2θ at 4.1° to 4.30.

Item 8. The crystal according to Item 4, having an X-ray powder diffraction spectrum comprising a characteristic peak expressed in degrees 2θ at 3.7° to 3.9°.

Item 9. The crystal according to any one of Items 1 to 8, having a melting point of 187 to 190° C.

Item 10. A method for producing the crystal according to any one of Items 1 to 9, the method comprising step (H) of reacting a cyclic phosphonic acid ester represented by formula (9):

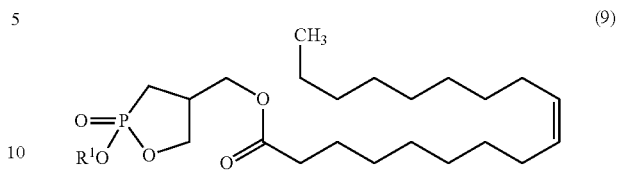

wherein $R^1$ represents alkyl, arylalkyl, or aryl with a sodium halide in an organic solvent to obtain 2ccPA, and step (I) of concentrating a solution containing the 2ccPA obtained in step (H) under reduced pressure, or cooling the solution containing the 2ccPA obtained in step (H) to precipitate the crystal.

Item 11. The method for producing the crystal according to Item 10, the method further comprising step (J) of dissolving the crystal obtained in step (I) in water and/or an organic solvent to obtain a solution, and step (K) of adding a poor solvent to the solution obtained in step (J) to perform recrystallization.

Item 12. A crystal of a cyclic phosphonic acid sodium salt (2ccPA) obtained by the method according to Item 10 or 11.

Item 13. A method for producing a crystal of a cyclic phosphonic acid sodium salt (2ccPA) represented by formula (1):

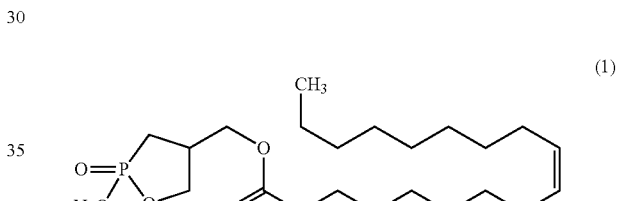

the method comprising step (H) of reacting a cyclic phosphonic acid ester represented by formula (9):

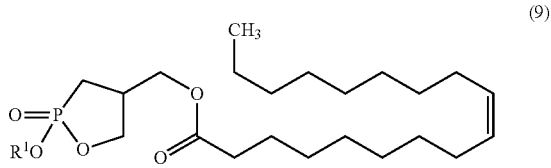

wherein $R^1$ represents alkyl, arylalkyl, or aryl with a sodium halide in an organic solvent.

Item 14. A method for producing a cyclic phosphonic acid ester represented by formula (9):

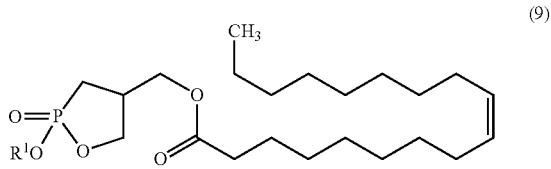

wherein $R^1$ represents alkyl, arylalkyl, or aryl, the method comprising step (G) of reacting a compound represented by formula (8):

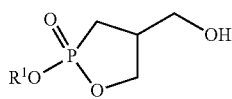
(8)

wherein R¹ is as defined above with an oleic acid compound.

Item 15. A method for producing a compound represented by formula (8):

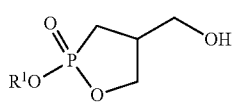
(8)

wherein R¹ represents alkyl, arylalkyl, or aryl, the method comprising step (F) of allowing a base to act on a compound represented by formula (7):

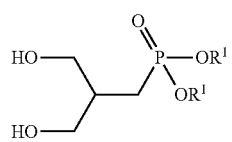
(7)

wherein two R¹ groups are the same or different and represent alkyl, arylalkyl, or aryl.

Item 16. A method for producing a compound represented by formula (7):

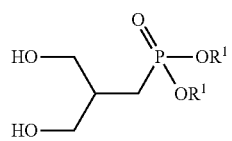
(7)

wherein two R¹ groups are the same or different and represent alkyl, arylalkyl, or aryl, the method comprising step (E) of allowing an acid to act on a compound represented by formula (6):

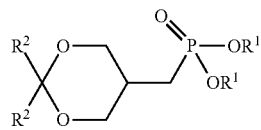
(6)

wherein R¹ is as defined above; and two R² groups are the same or different and represent alkyl, cycloalkyl, or aryl.

Item 17. A method for producing a compound represented by formula (6):

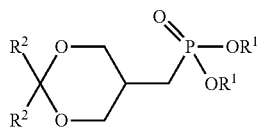
(6)

wherein two R¹ groups are the same or different and represent alkyl, arylalkyl, or aryl; and two R groups are the same or different and represent alkyl, cycloalkyl, or aryl, the method comprising step (D) of reacting a compound represented by formula (5):

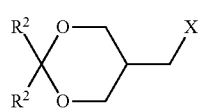
(5)

wherein R$^z$ is as defined above; and X represents a halogen atom with a phosphorous acid diester.

Item 18. A method for producing a halogen compound represented by formula (5):

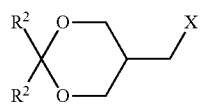
(5)

wherein two R² groups are the same or different and represent alkyl, cycloalkyl, or aryl; and X represents a halogen atom, the method comprising step (C) of reacting a compound represented by formula (4):

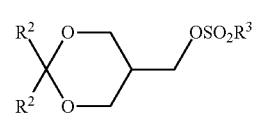
(4)

wherein R² is as defined above; and R³ represents substituted or unsubstituted alkyl or substituted or unsubstituted aryl with an alkali metal halide and/or an alkaline-earth metal halide in the presence of a base.

Item 19. A method for producing a compound represented by formula (4):

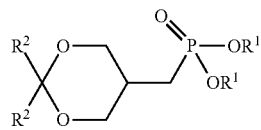
(4)

wherein two R² groups are the same or different and represent alkyl, cycloalkyl, or aryl; and R³ represents substituted or unsubstituted alkyl or substituted or unsubstituted aryl, the method comprising step (B) of reacting a compound represented by formula (3):

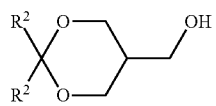
(3)

wherein R² is as defined above with a sulfonyl halide compound.

Item 20. A method for producing a compound represented by formula (5):

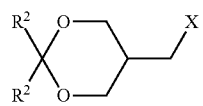
(5)

wherein two R² groups are the same or different and represent alkyl, cycloalkyl, or aryl; and X represents a halogen atom, the method comprising step (B') of reacting a compound represented by formula (3):

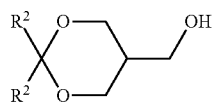
(3)

wherein R² is as defined above with a halogenating agent.

Item 21. The method for producing the crystal according to Item 10 or 13, the method further comprising the step of any one of Items 14 to 20.

Advantageous Effects of Invention

The crystal of 2ccPA according to the present invention is excellent in storage stability, and does not significantly decompose when stored for a long period of time.

Following the production method of the present invention, a high-purity crystal of 2ccPA can be produced at a high yield in a simple manner.

Specifically, the production method of the present invention includes a novel production method, and, in particular, the present invention can produce a cyclic phosphonic acid ester, which is a precursor of 2ccPA, without performing isolation and purification in each step (Telescoping).

The production method of the present invention also reduces the risk of decreases in purity without using a strong acid or strong base, and produces a crystal of 2ccPA excellent in stability from the cyclic phosphonic acid ester in a simple manner.

DESCRIPTION OF EMBODIMENTS

Figure 1:
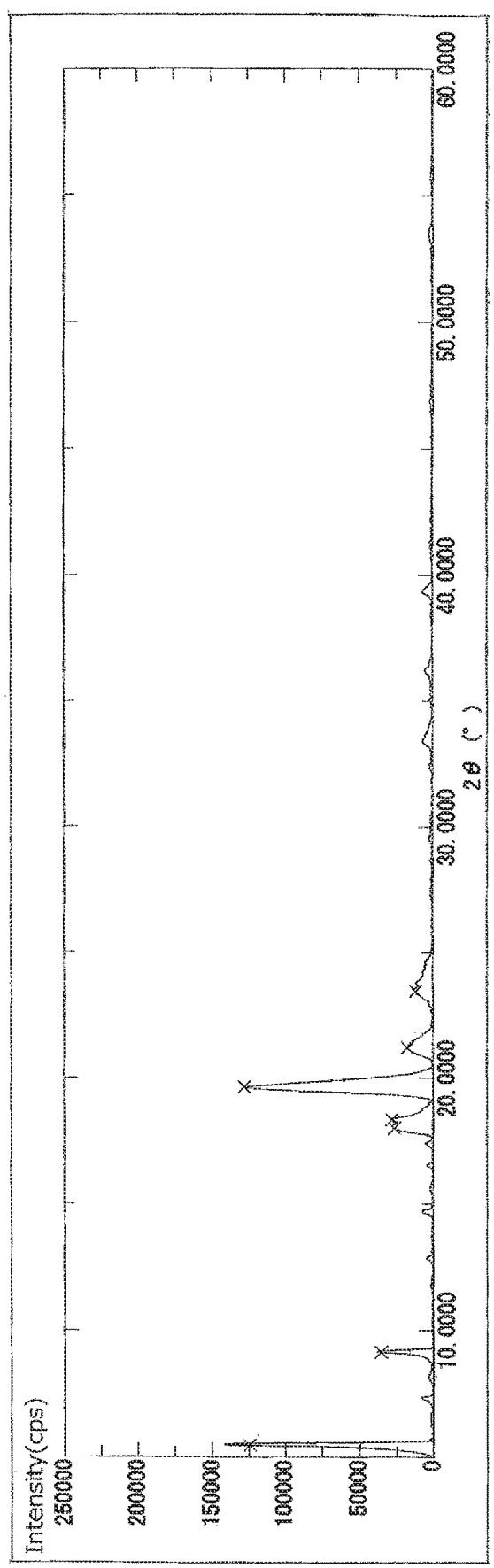
FIG. 1 illustrates an X-ray powder diffraction spectrum of the crystal of 2ccPA obtained in Example 1.
Figure 2:
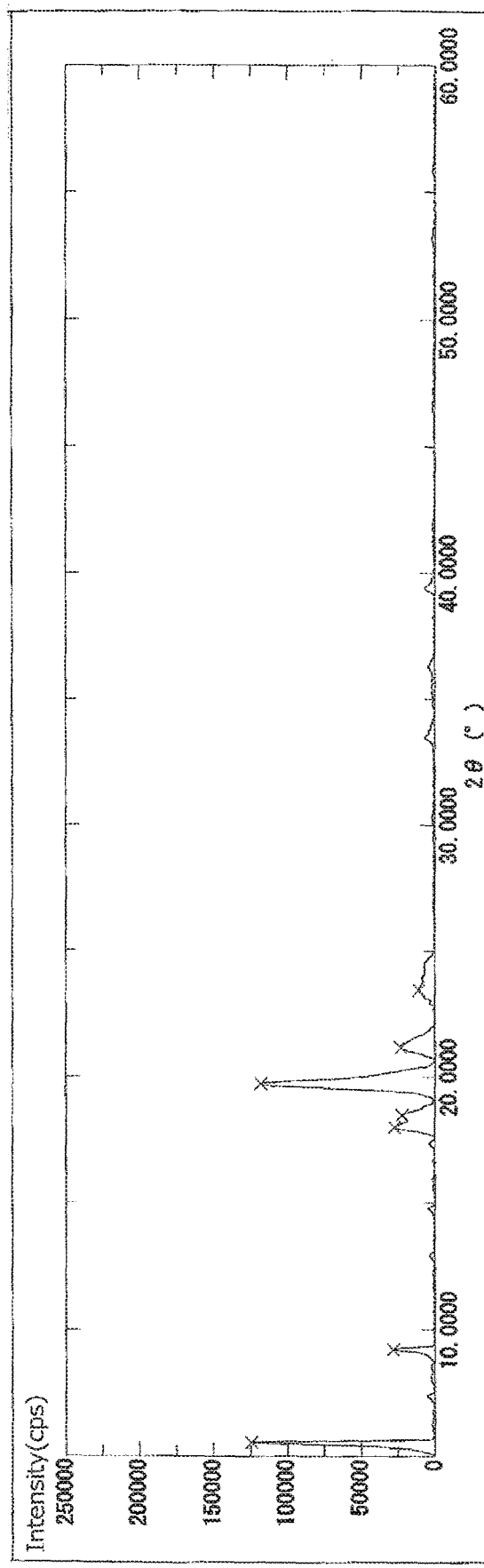
FIG. 2 illustrates an X-ray powder diffraction spectrum of the crystal of 2ccPA obtained in Example 2.
Figure 3:
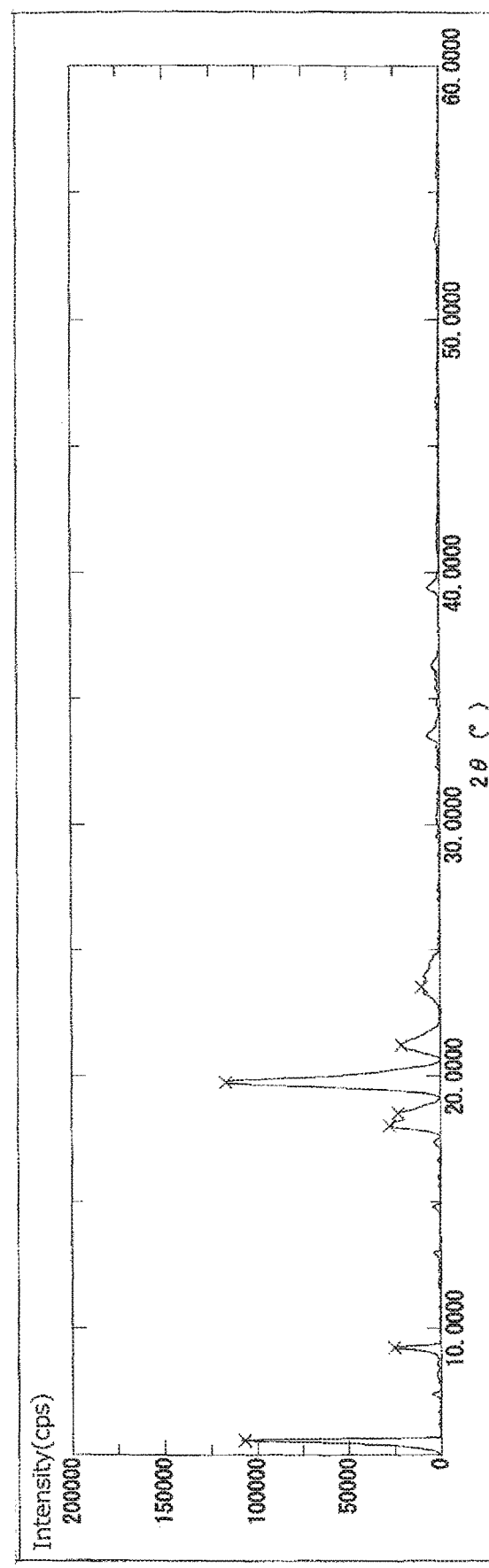
FIG. 3 illustrates an X-ray powder diffraction spectrum of the crystal of 2ccPA obtained in Example 3.
Figure 4:
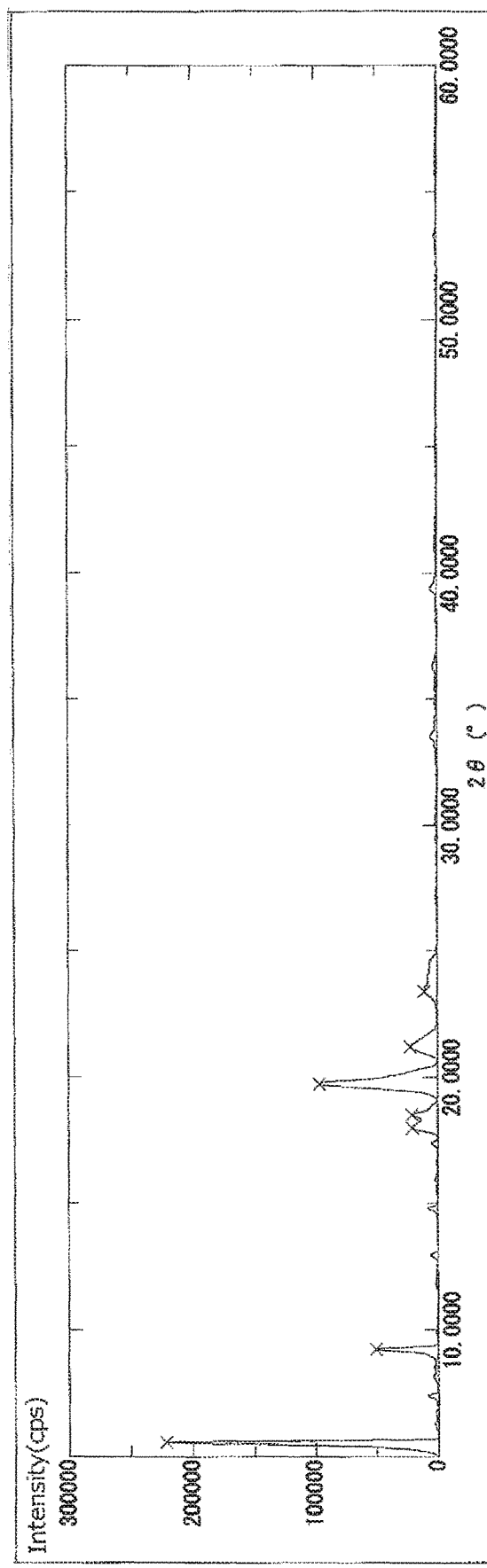
FIG. 4 illustrates an X-ray powder diffraction spectrum of the crystal of 2ccPA obtained in Example 4.
Figure 5:
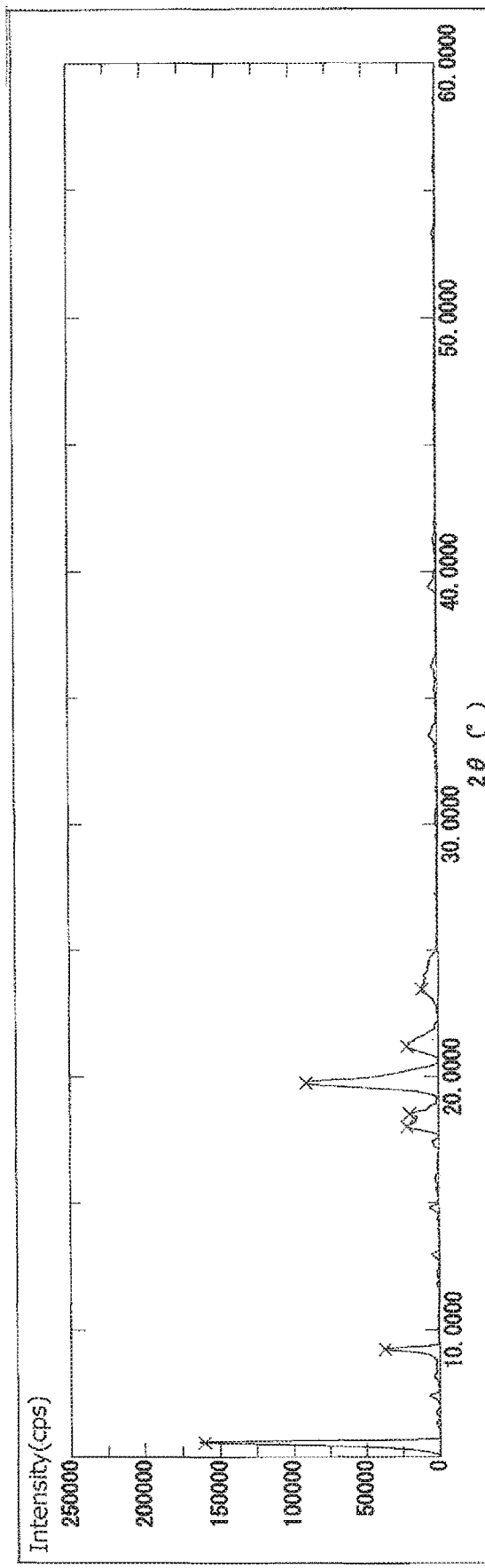
FIG. 5 illustrates an X-ray powder diffraction spectrum of the crystal of 2ccPA obtained in Example 5.
Figure 6:
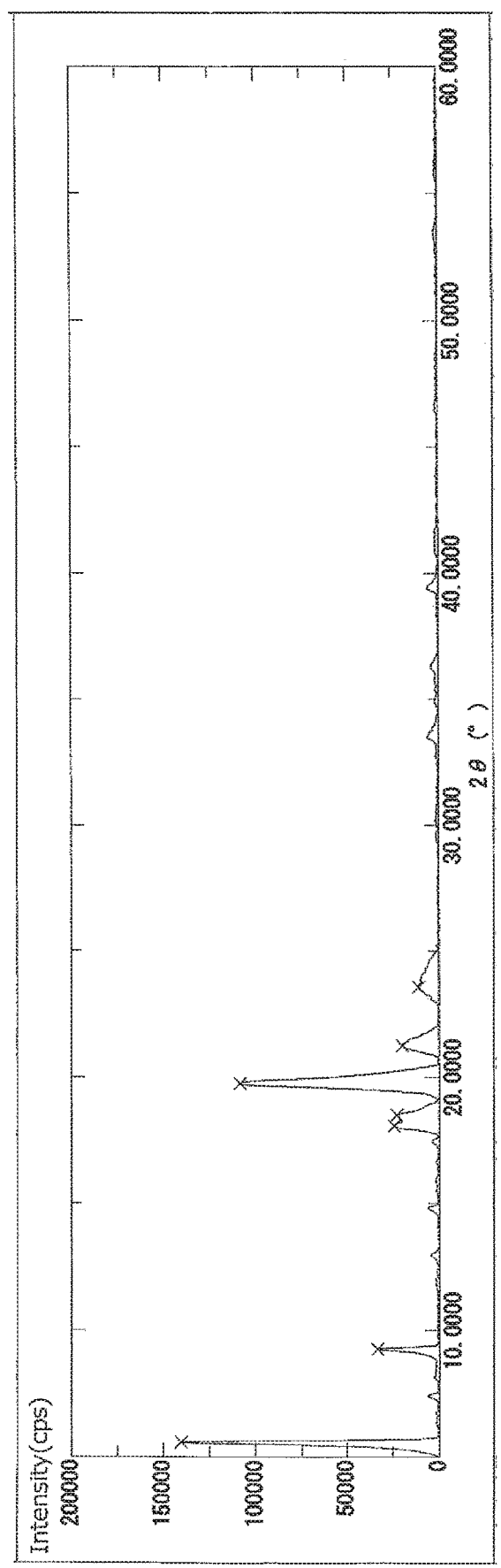
FIG. 6 illustrates an X-ray powder diffraction spectrum of the crystal of 2ccPA obtained in Example 6.
Figure 7:
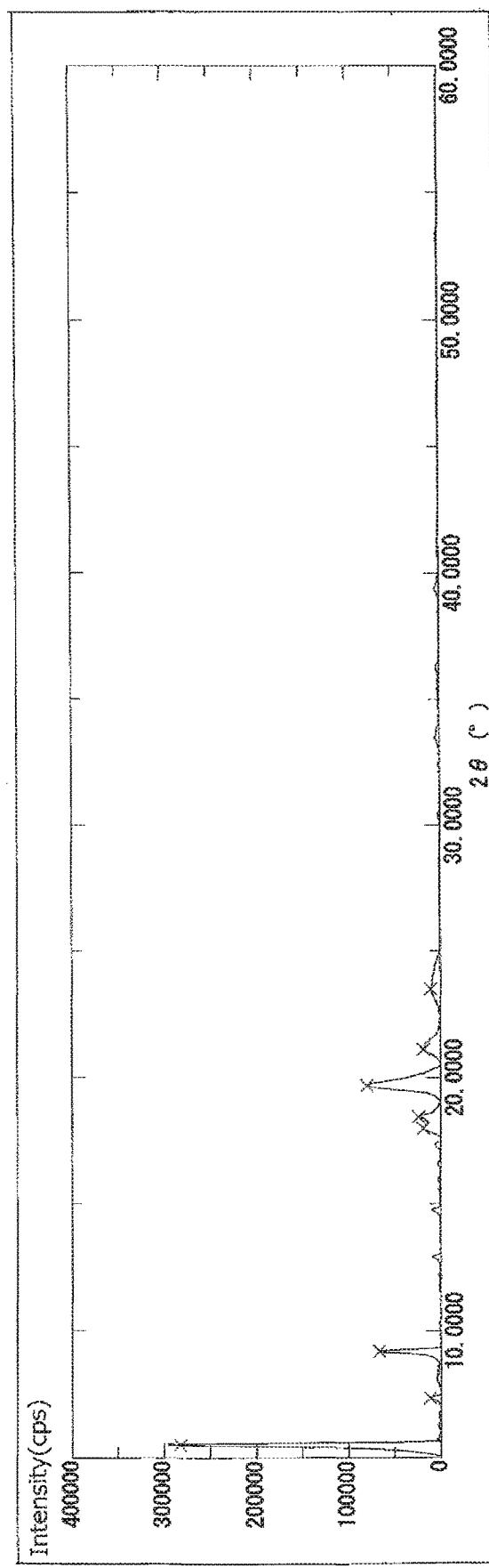
FIG. 7 illustrates an X-ray powder diffraction spectrum of the crystal of 2ccPA obtained in Example 7.
Figure 8:
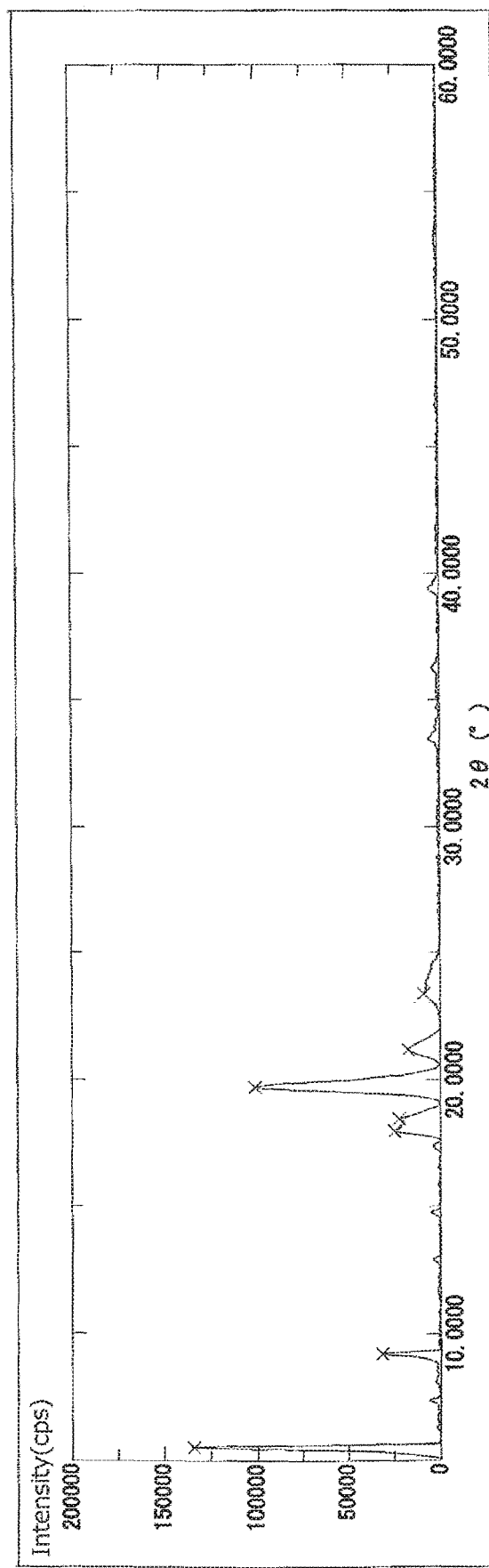
FIG. 8 illustrates an X-ray powder diffraction spectrum of the crystal of 2ccPA obtained in Example 8.
Figure 9:
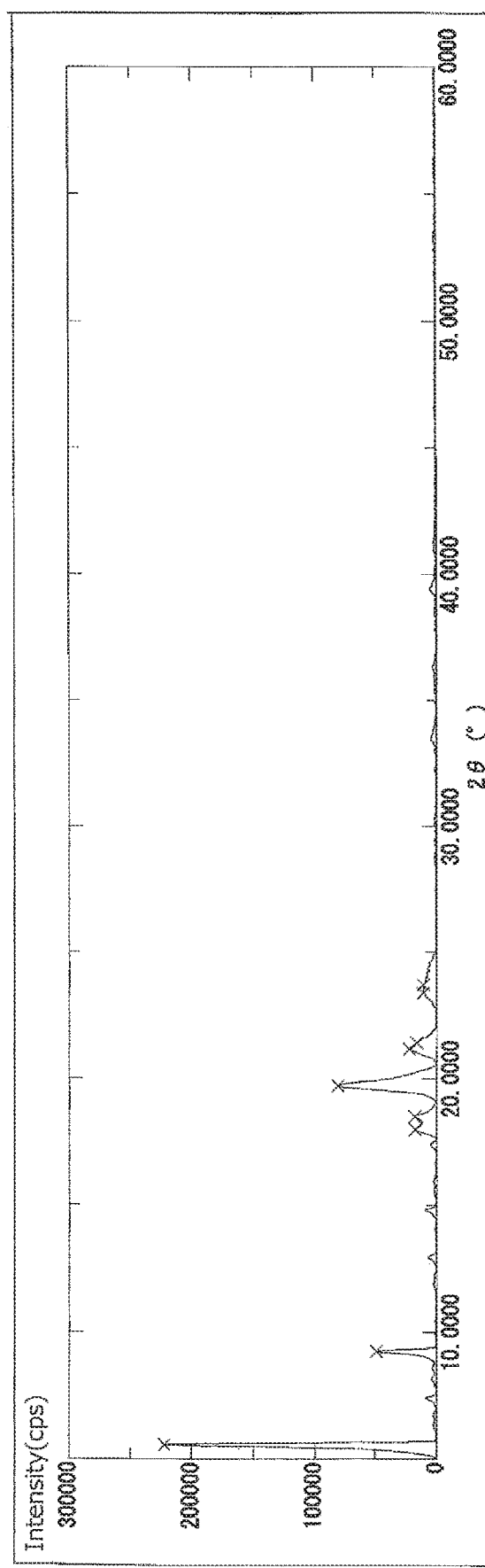
FIG. 9 illustrates an X-ray powder diffraction spectrum of the crystal of 2ccPA obtained in Example 9.
Figure 10:
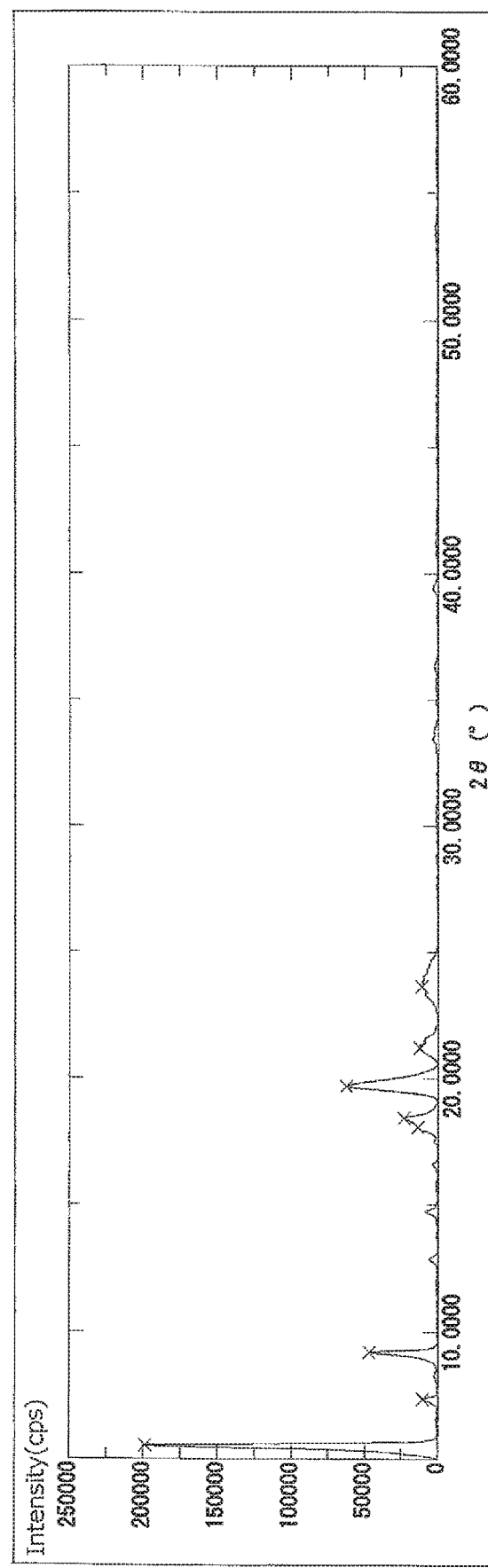
FIG. 10 illustrates an X-ray powder diffraction spectrum of the crystal of 2ccPA obtained in Example 10.
Figure 11:
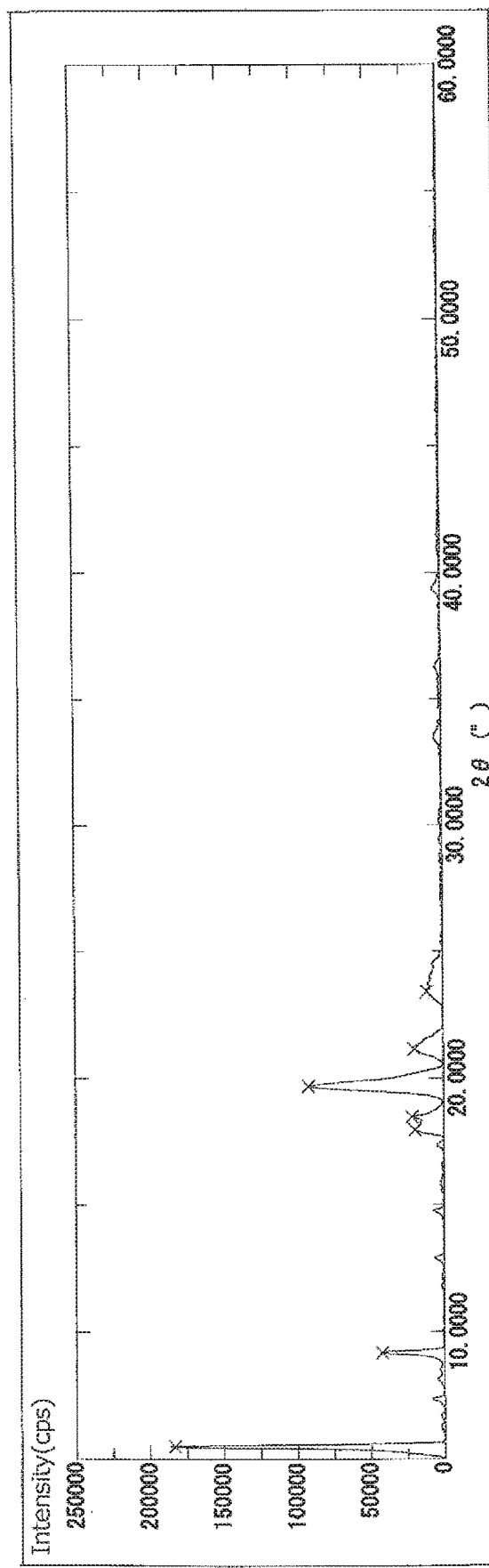
FIG. 11 illustrates an X-ray powder diffraction spectrum of the crystal of 2ccPA obtained in Example 11.
Figure 12:
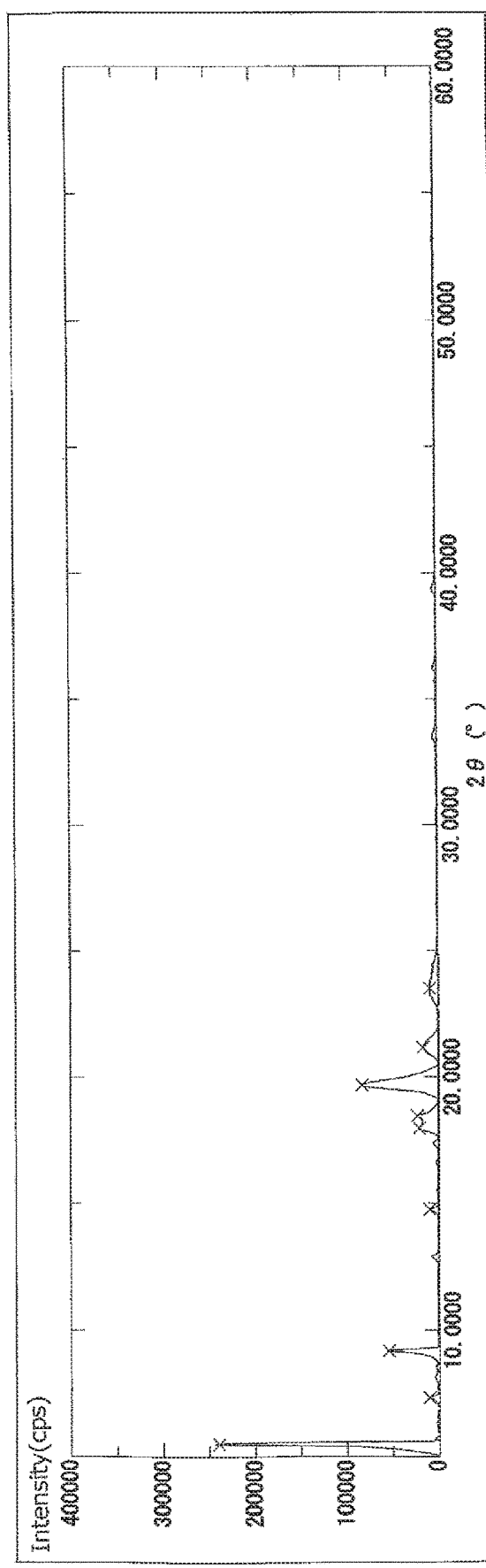
FIG. 12 illustrates an X-ray powder diffraction spectrum of the crystal of 2ccPA obtained in Example 12.
Figure 13:
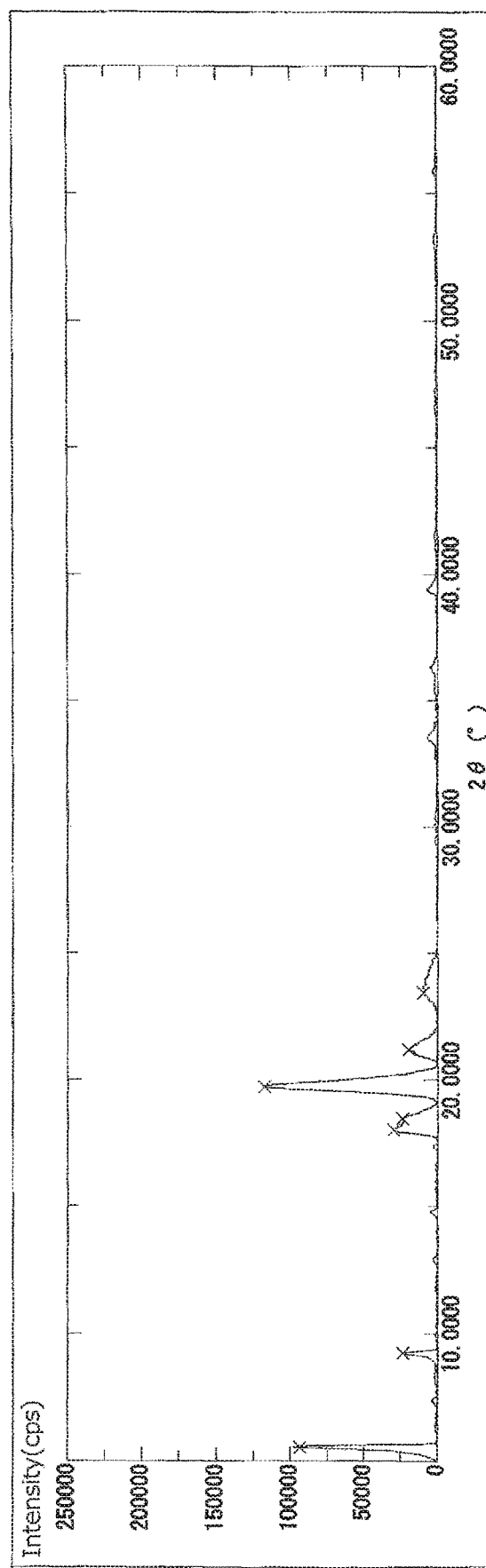
FIG. 13 illustrates an X-ray powder diffraction spectrum of the crystal of 2ccPA obtained in Example 13.
Figure 14:
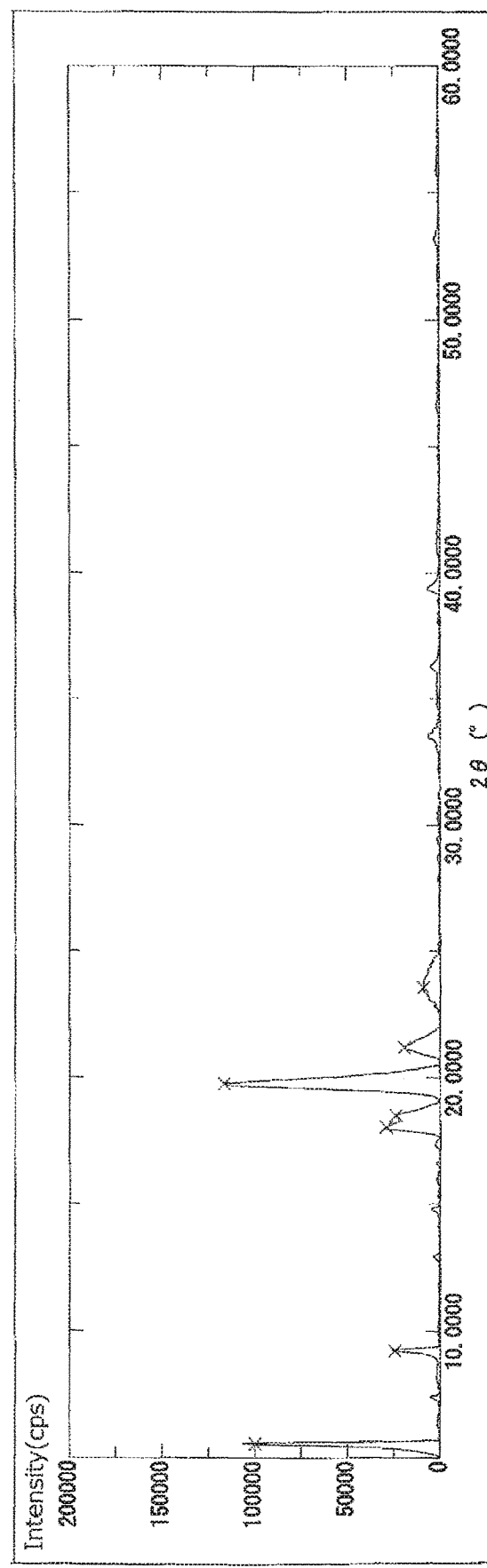
FIG. 14 illustrates an X-ray powder diffraction spectrum of the crystal of 2ccPA obtained in Example 14.
Figure 15:
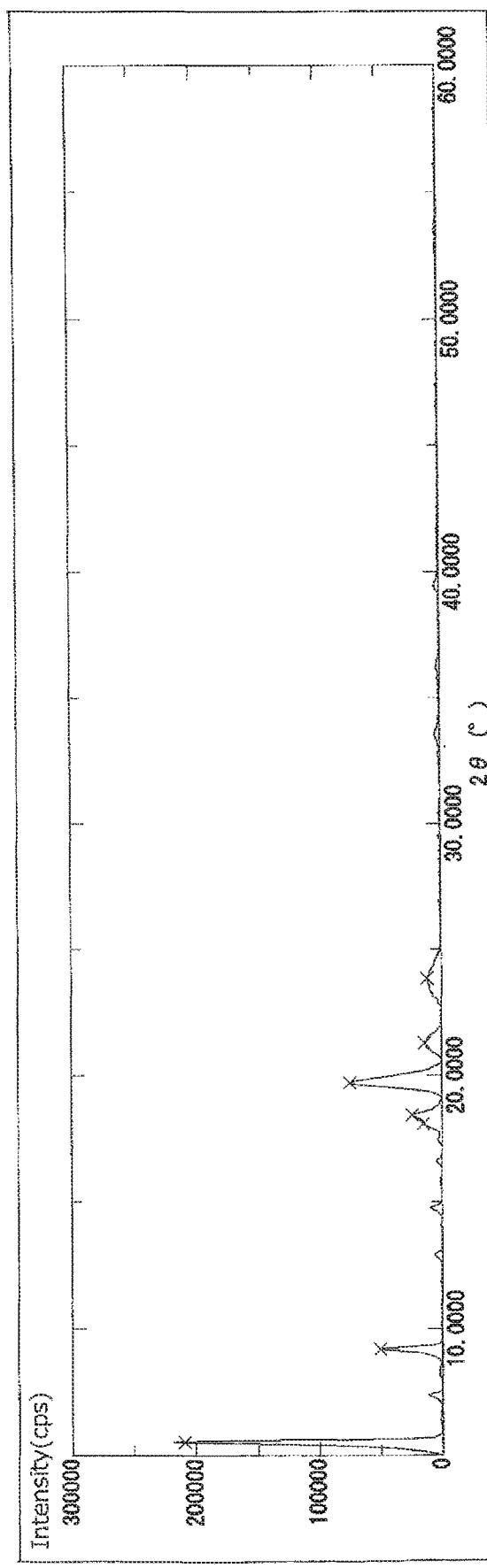
FIG. 15 illustrates an X-ray powder diffraction spectrum of the crystal of 2ccPA obtained in Example 15.
Figure 16:
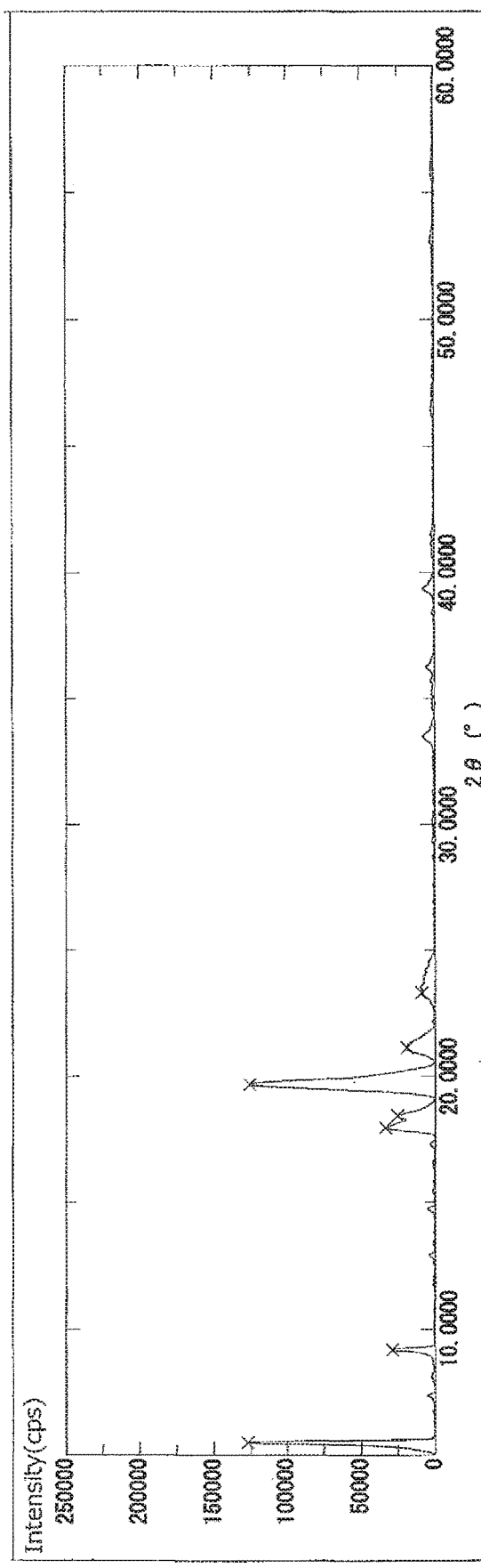
FIG. 16 illustrates an X-ray powder diffraction spectrum of the crystal of 2ccPA obtained in Example 16.
Figure 17:
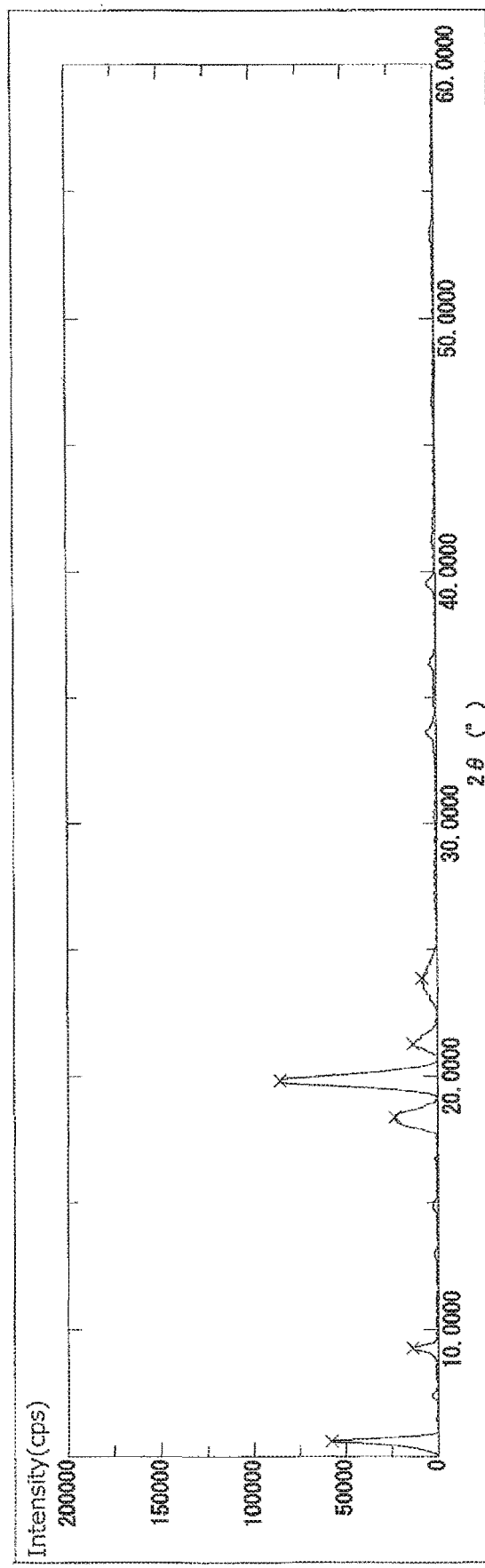
FIG. 17 illustrates an X-ray powder diffraction spectrum of the crystal of 2ccPA obtained in Example 17.
Figure 18:
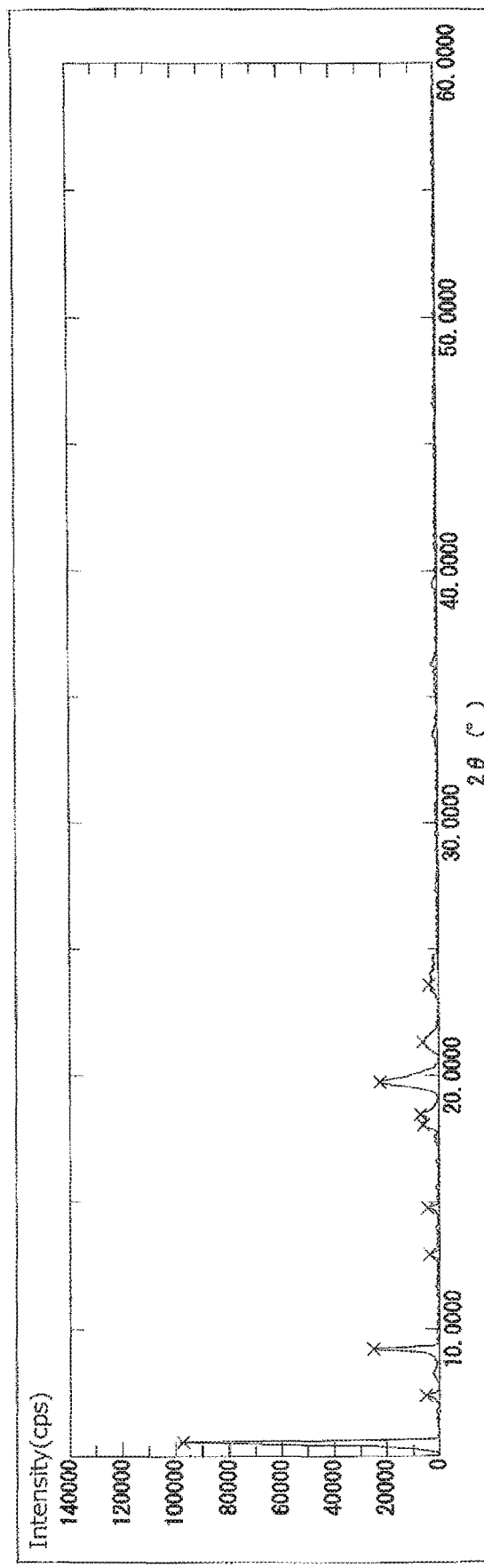
FIG. 18 illustrates an X-ray powder diffraction spectrum of the crystal of 2ccPA obtained in Example 18.
Figure 19:
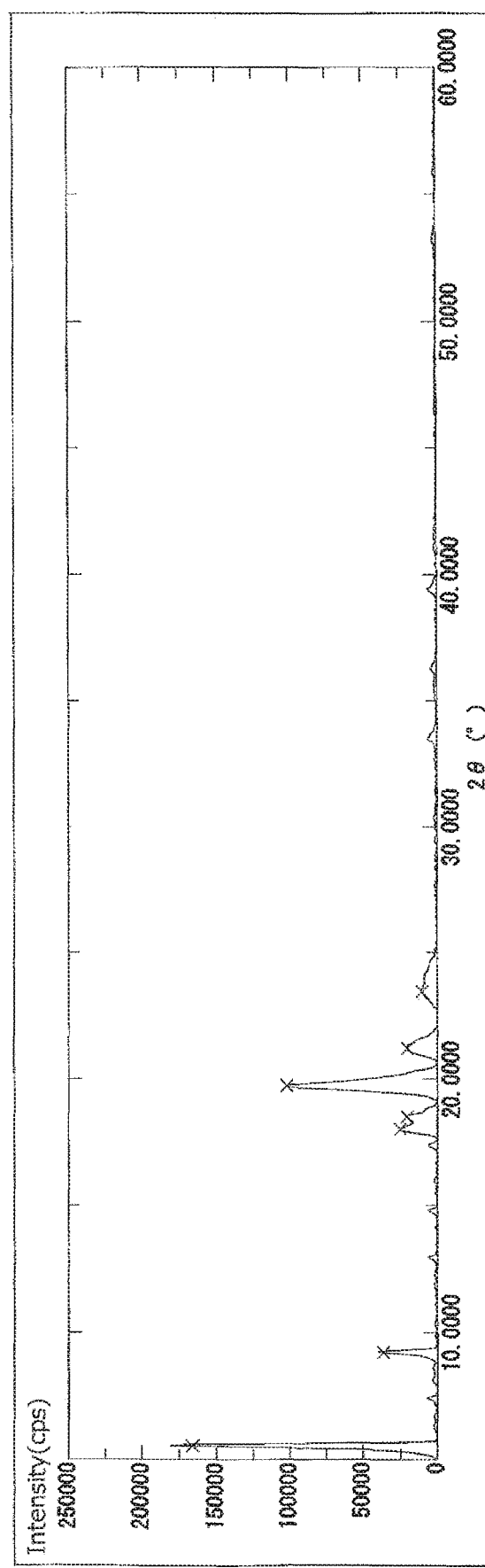
FIG. 19 illustrates an X-ray powder diffraction spectrum of the crystal of 2ccPA obtained in Example 19.
Figure 20:
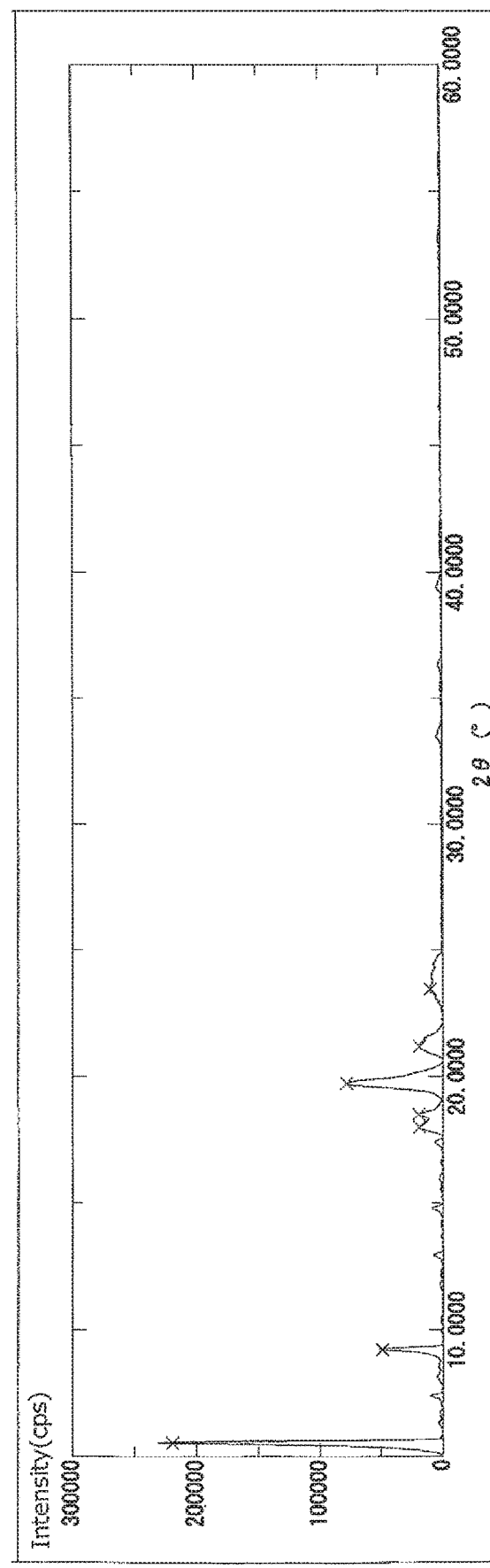
FIG. 20 illustrates an X-ray powder diffraction spectrum of the crystal of 2ccPA obtained in Example 20.
Figure 21:
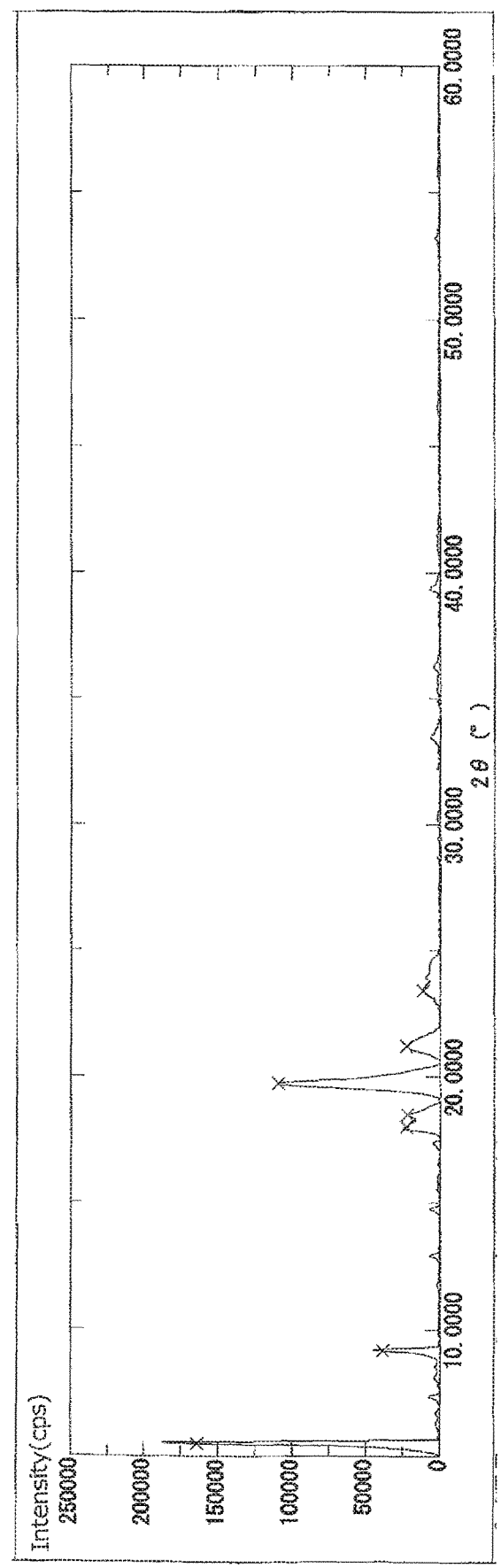
FIG. 21 illustrates an X-ray powder diffraction spectrum of the crystal of 2ccPA obtained in Example 21.
Figure 22:
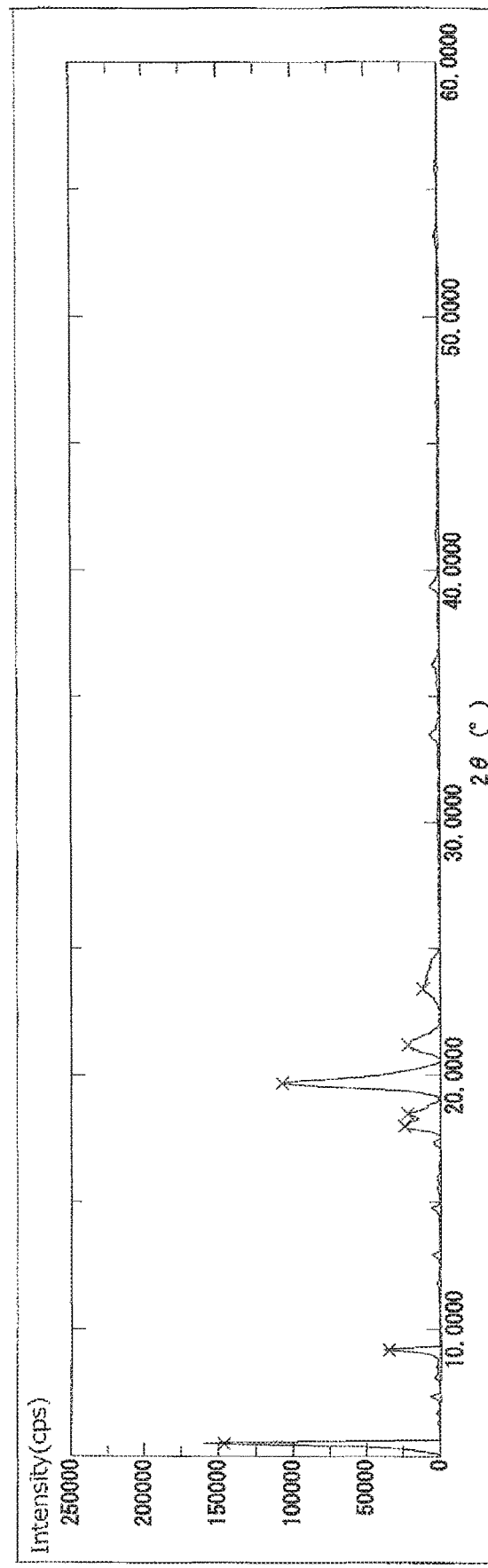
FIG. 22 illustrates an X-ray powder diffraction spectrum of the crystal of 2ccPA obtained in Example 22.
Figure 23:
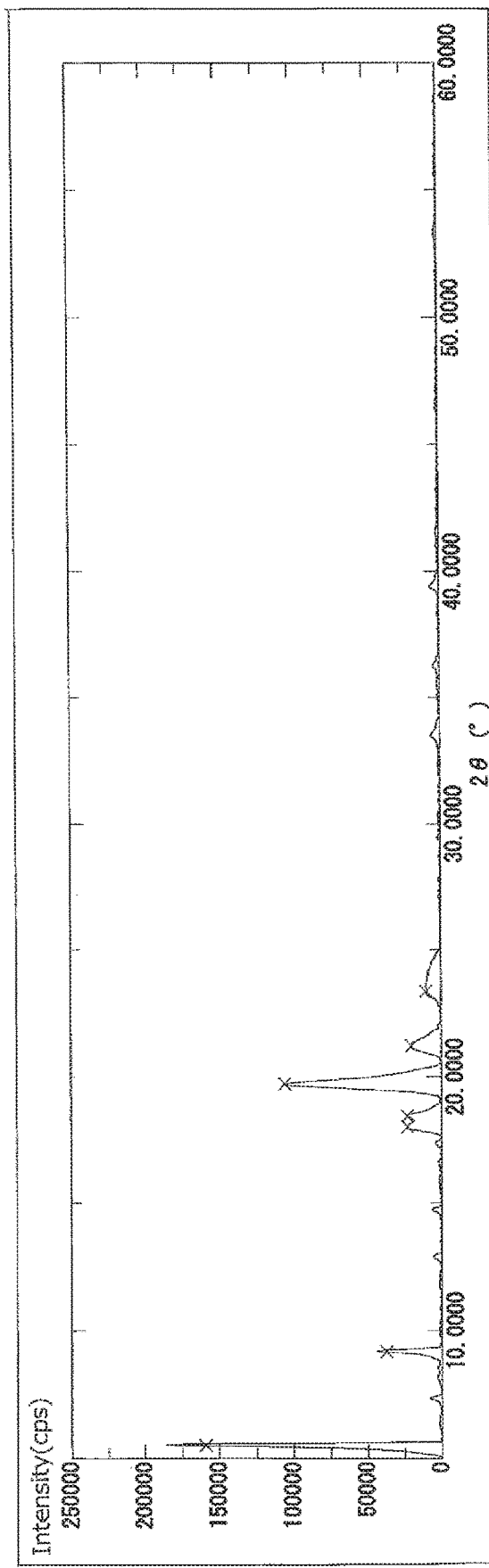
FIG. 23 illustrates an X-ray powder diffraction spectrum of the crystal of 2ccPA obtained in Example 23.
Figure 24:
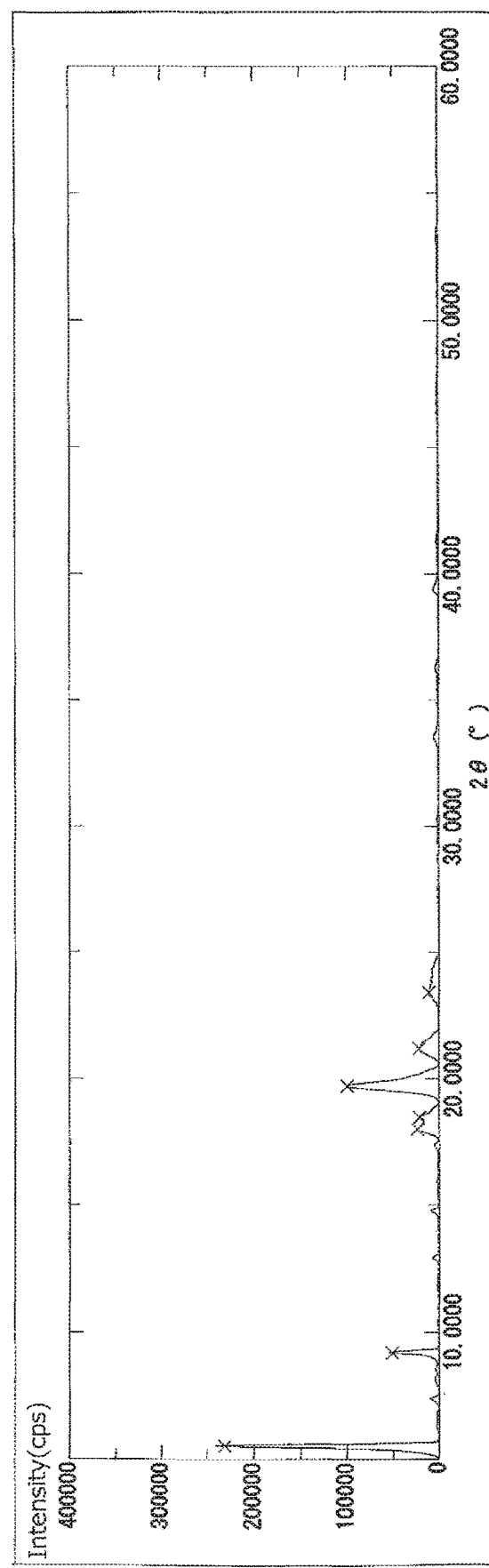
FIG. 24 illustrates an X-ray powder diffraction spectrum of the crystal of 2ccPA obtained in Example 24.
Figure 25:
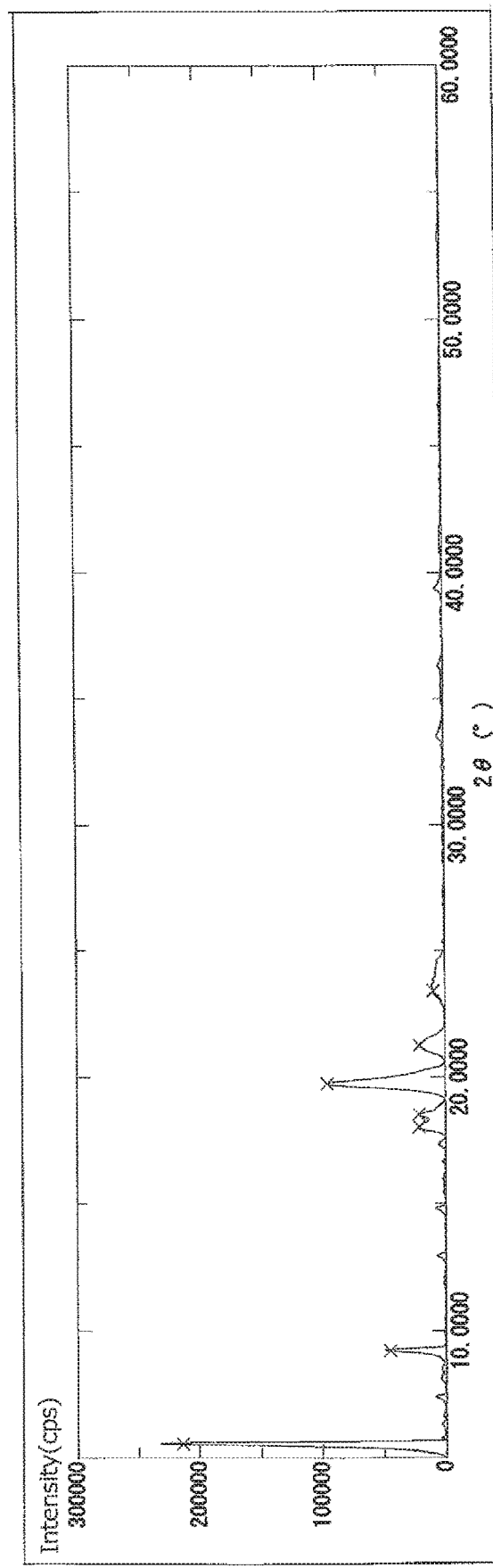
FIG. 25 illustrates an X-ray powder diffraction spectrum of the crystal of 2ccPA obtained in Example 25.
Figure 26:
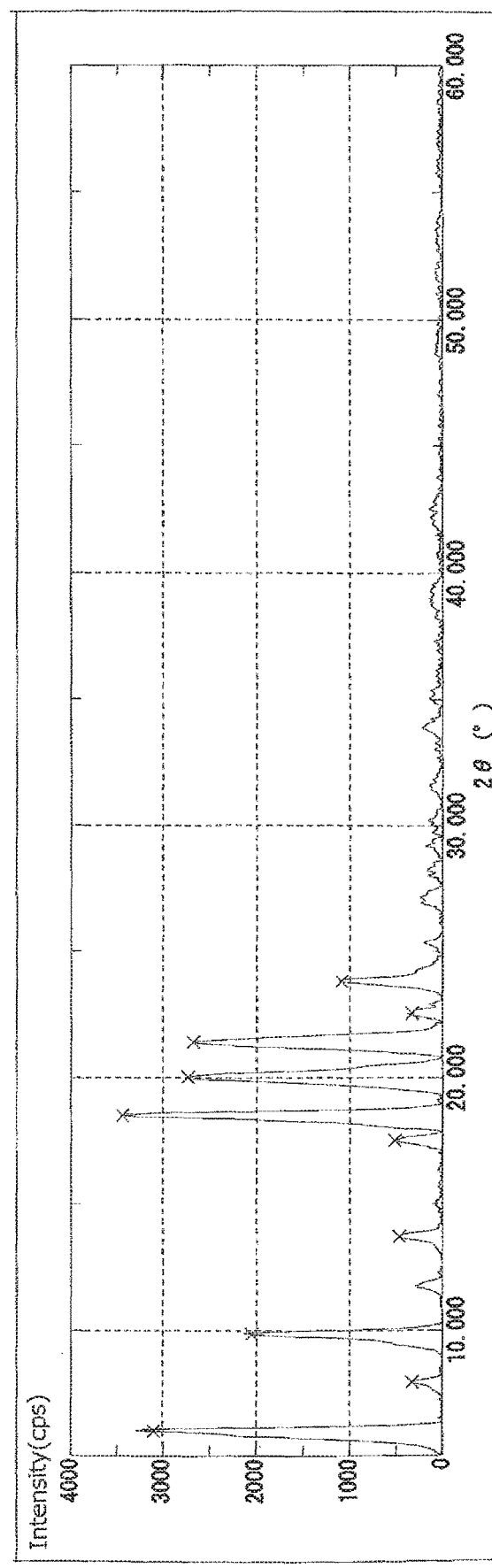
FIG. 26 illustrates an X-ray powder diffraction spectrum of the crystal of 2ccPA obtained in Example 26.
Figure 27:
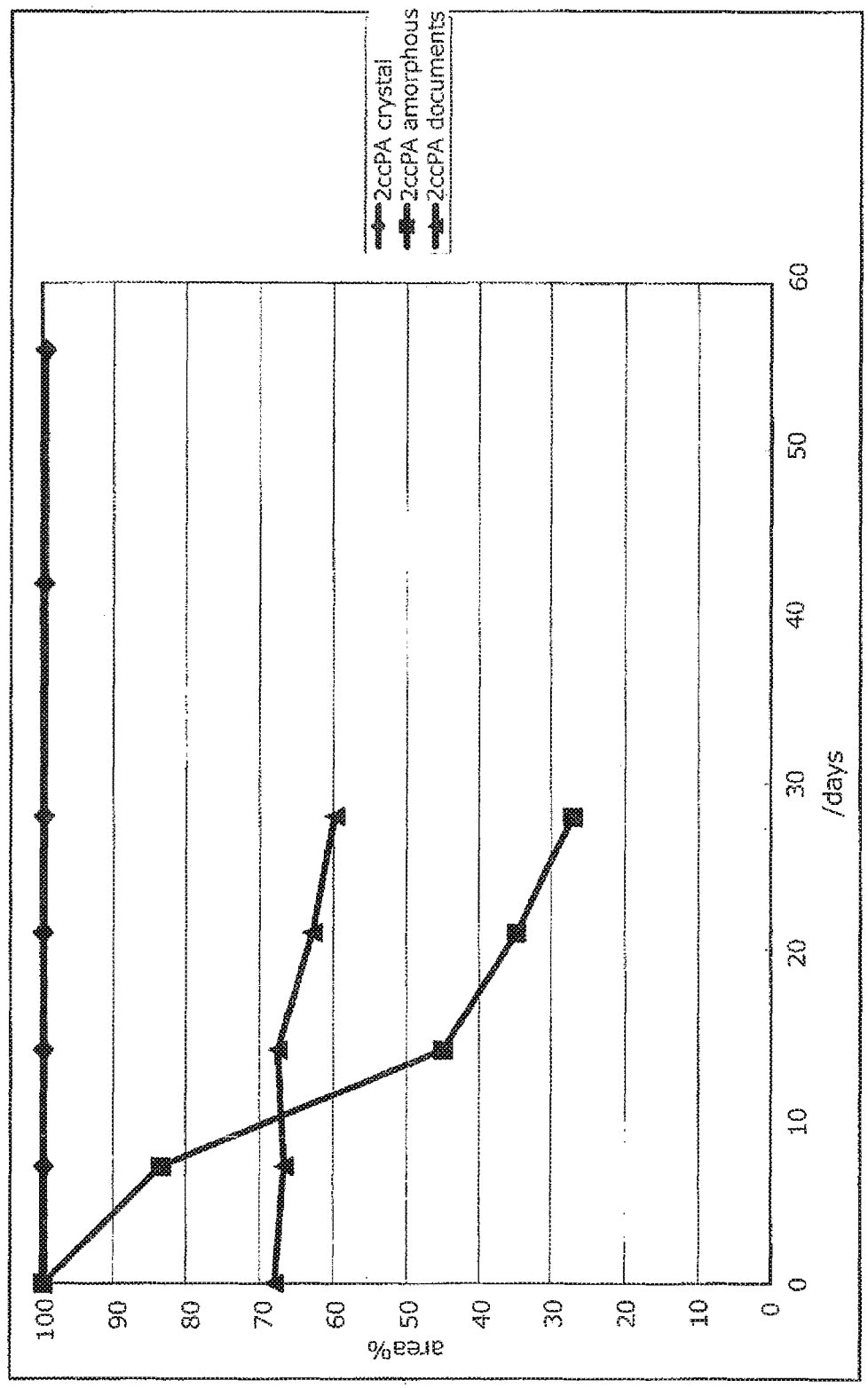
FIG. 27 is a graph illustrating the results of a stability test.

The following describes in detail a novel crystal of 2ccPA and a method for producing the crystal according to the present invention.

In this specification, the term "comprise" includes the concept of "comprise," "consist essentially of," and "consist of."

1. Crystal of Cyclic Phosphonic Acid Sodium Salt (2ccPA)

The crystal of 2ccPA of the present invention is a crystal of a cyclic phosphonic acid sodium salt (a sodium salt of 9-octadecenoic acid (9Z)-(2-hydroxy-2-oxo-2$\lambda^5$-1,2-oxa-phosphoran-4-yl)methyl ester; IUPAC name: 4-[(Z)-octa-dec-9-enoyloxymethyl]-2-oxo-1,2-$\lambda^5$-oxaphosphorane-2-olate sodium salt).

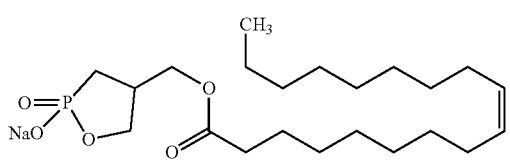

(1)

The crystal of 2ccPA exhibits a characteristic peaks in the following lattice spacing (d) in an X-ray powder diffraction spectrum obtained with monochromated copper radiation (λ=1.54059 Å), as measured with, for example, a RINT-2000 Ultima IV (produced by Rigaku Corporation, trade name).

The crystal of 2ccPA has a crystal X-ray powder diffraction spectrum comprising a characteristic peak(s) expressed in degrees 2θ at about 15° to 17° (hereinafter, "peak A"), a characteristic peak expressed in degrees 2θ at about 9° to 10° (hereinafter "peak B"), or at least one characteristic peak expressed in degrees 2θ at about 3° to 5° (hereinafter "peaks C to F").

The peaks C to F further comprise the following peaks C, D, E and/or F:

characteristic peaks at about 4.7° to 5.0° (hereinafter, "peak C")

a characteristic peak at about 4.4° to 4.6° (hereinafter, "peak D")

a characteristic peak at about 4.1° to 4.3° (hereinafter, "peak E"), and a characteristic peak at about 3.7° to 3.9° (hereinafter, "peak F").

Peak C comprises characteristic peaks at about 4.70 to 4.9° and/or about 4.9° to 5.0°.

The crystal of 2ccPA of the present invention is substantially in a laminated flaky crystalline form.

The crystal of 2ccPA of the present invention has a melting point within the range of 187° C. to 190° C. The melting point is measured with a melting point measuring apparatus B-545 (produced by Büchii).

The IR spectrum of the crystal of 2ccPA of the present invention is measured with a Spectrum One B IR spectrometer (Perkin Elmer).

The purity of the crystal of 2ccPA of the present invention is measured with high-performance liquid chromatography (HPLC) using a reverse-phase silica gel column. The purity is typically 98% or more.

The crystal of 2ccPA of the present invention is excellent in storage stability. After being hermetically sealed and stored at −20° C. and 35° C. for 3 months, the crystal of 2ccPA shows little decrease in purity and does not significantly decompose.

2. Method for Producing Crystal of 2ccPA

The method for producing the crystal of 2ccPA of the present invention comprises the following step (H) and step (I).

The method comprises:

step (H) of reacting a cyclic phosphonic acid ester represented by formula (9):

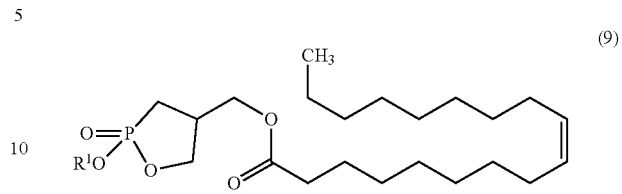

(9)

wherein $R^1$ is as defined above with a sodium halide in an organic solvent to obtain 2ccPA, and step (I) of concentrating a solution containing the 2ccPA obtained in step (H) under reduced pressure or cooling the solution containing the 2ccPA obtained in step (H) to precipitate the crystal.

The method for producing the crystal of 2ccPA of the present invention may further comprise, in addition to step (H) and step (I), the following step (J) and step (K):

step (J) of dissolving the crystal obtained in step (H) and step (I) in water and/or an organic solvent; and step (K) of adding a poor solvent to the solution obtained in step (J) to perform recrystallization.

2-1. Step (H)

Step (H) is illustrated in the following reaction scheme-2:

Reaction Scheme-2

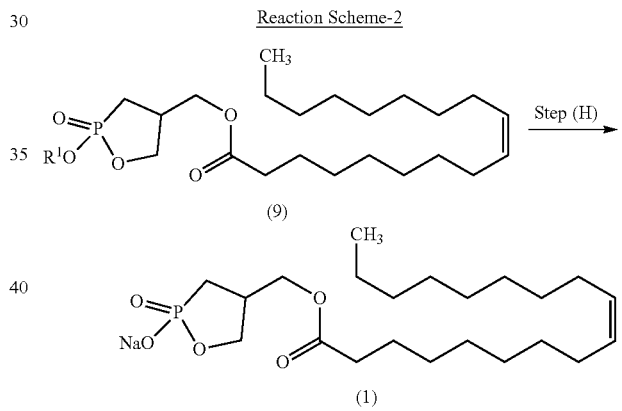

wherein $R^1$ is as defined above.

Specifically, step (H) is a step of reacting the cyclic phosphonic acid ester represented by formula (9) with a sodium halide in an organic solvent to obtain 2ccPA represented by formula (1), and step (H) produces a solution containing 2ccPA.

The cyclic phosphonic acid ester represented by formula (9) and used in step (H) is produced through the production steps described later.

In the cyclic phosphonic acid ester represented by formula (9), examples of the alkyl represented by $R^1$ include linear or branched alkyl having 1 to 10 carbon atoms. Specific examples include methyl, ethyl, n-propyl, isopropyl, n-butyl, isobutyl, s-butyl, t-butyl, n-pentyl, n-hexyl, n-heptyl, n-octyl, and n-nonyl. The alkyl represented by R: is preferably alkyl having 1 to 6 carbon atoms, more preferably alkyl having 1 to 4 carbon atoms, and particularly preferably methyl, ethyl, and isopropyl.

The alkyl may contain 1 to 5 substituents, and preferably 1 to 3 substituents, such as halogen atoms (e.g., fluorine, chlorine, and bromine), alkoxy having 1 to 6 carbon atoms, and nitro.

Examples of the arylalkyl represented by $R^1$ include arylalkyl having 7 to 16 carbon atoms (the aryl moiety has 6 to 10 carbon atoms, and the alkyl moiety has 1 to 6 carbon atoms). Specific examples include benzyl; 1-phenyl ethyl, 2-phenyl ethyl; 1-phenyl propyl, 2-phenyl propyl, 3-phenyl propyl; 1-phenyl butyl, 2-phenyl butyl, 3-phenyl butyl, 4-phenyl butyl; and naphthyl methyl. The arylalkyl represented by $R^1$ is preferably arylalkyl having 7 to 11 carbon atoms, more preferably arylalkyl having 7 or 8 carbon atoms, and particularly preferably benzyl.

The aryl constituting the arylalkyl represented by $R^1$ may contain 1 to 5 substituents, and preferably 1 to 3 substituents, such as halogen atoms (e.g., fluorine, chlorine, and bromine), alkyl having 1 to 6 carbon atoms, alkoxy having 1 to 6 carbon atoms, and nitro.

Examples of the aryl represented by $R^1$ include monocyclic, dicyclic, or more than dicyclic aryl. Specific examples of the aryl include phenyl, naphthyl, anthryl, and phenanthryl. Of these, substituted or unsubstituted phenyl is preferable. The aryl may contain 1 to 5 substituents, and preferably 1 to 3 substituents, such as halogen atoms (e.g., fluorine, chlorine, and bromine), alkyl having 1 to 6 carbon atoms, alkoxy having 1 to 6 carbon atoms, and nitro.

The sodium halide for use in step (H) may be of a wide range of known sodium halides, such as sodium fluoride, sodium chloride, sodium bromide, and sodium iodide. Of these, sodium iodide is preferable. These sodium halides may be used singly or in a combination of two or more.

The amount of the sodium halide for use is typically 1 to 5 moles, preferably 1 to 3 moles, and more preferably 1 to 1.5 moles, per mole of the compound represented by formula (9).

The organic solvent for use in step (H) is not particularly limited, as long as the solvent does not adversely affect the reaction. Examples of the organic solvent for use include ketone solvents (e.g., branched or linear ketone and cyclic ketone, such as acetone, methyl ethyl ketone, methyl butyl ketone, methyl isobutyl ketone, DIBK (diisobutyl ketone), and cyclohexanone), alcohol solvents (e.g., methanol and ethanol), ether solvents (e.g., diethyl ether, diisopropyl ether, tetrahydrofuran (THF), and 1,4-dioxane), aromatic hydrocarbon solvents (e.g., benzene, toluene, and xylene), aliphatic or alicyclic hydrocarbon solvents (e.g., n-pentane, n-hexane, cyclohexane, and petroleum ether), ester solvents (e.g., ethyl acetate), and halogenated hydrocarbon solvents (e.g., methylene chloride, chloroform, and 1,2-dichloroethylene). These organic solvents may be used singly or in a combination of two or more. Of these organic solvents, ketone solvents are preferable, with acetone, methyl ethyl ketone, and methyl isobutyl ketone being particularly preferable.

The amount of the organic solvent for use can be suitably selected from a wide range. For example, the amount of the organic solvent is typically 2 to 20 liters, and preferably 2 to 5 liters, per mole of the compound represented by formula (9).

Step (H) may be performed in an inert gas atmosphere, such as nitrogen or argon.

The reaction pressure is not particularly limited, and the reaction can be performed under ordinary pressure or increased pressure.

The reaction temperature is typically 0 to 120° C., preferably 50 to 120° C., and more preferably 70 to 120° C.

The reaction time is typically 0.1 to 100 hours, preferably 0.5 to 50 hours, and more preferably 1 to 24 hours.

After completion of the reaction, from the obtained reaction mixture, an excess amount of the reagent (e.g., the sodium halide), the unreacted starting material compound, and other components are removed by a typical separation technique, such as concentration, crystallization, and filtration to isolate the target 2ccPA represented by formula (1).

2-2. Step (I)

Step (I) is a step of concentrating a solution containing the 2ccPA obtained in step (H) under reduced pressure, or cooling the solution containing the 2ccPA obtained in step (H) to precipitate the crystal.

The reduced pressure in step (I) is not particularly limited, as long as the crystal can be precipitated under the pressure. The reduced pressure is typically lower than the atmospheric pressure.

The cooling temperature in step (I) is not particularly limited, as long as the crystal can be precipitated at the temperature. The cooling temperature is typically lower than the temperature of the solution after the reaction in step (H), and preferably 0 to 30° C., and more preferably 10 to 25° C.

The cooling time is not particularly limited, and typically 0.1 to 100 hours, preferably 0.5 to 50 hours, and more preferably 1 to 2 hours.

The obtained crystal can be used in the subsequent step (J).

2-3. Step (J)

Step (J) is a step of dissolving the crystal obtained in step (H) and step (I) in water and/or an organic solvent to obtain a solution.

The water and/or organic solvent for use in step (J) can be any water and/or organic solvent that can dissolve the crystal obtained in step (I). Examples of the organic solvent include alcohol solvents, and in particular, methanol, ethanol, 1-propanol, isopropyl alcohol, and 1-butanol are preferable.

The amount of the water and/or organic solvent for use can be suitably selected from a wide range. For example, the amount of the water and/or organic solvent is typically 0.5 to 20 liters, and preferably 0.5 to 2 liters, per mole of 2ccPA.

In the use of a mixture solvent of water and an organic solvent, the mixing ratio is not particularly limited. The mixing ratio of water to an organic solvent is preferably 1:99 to 99:1, and more preferably 30:70 to 70:30.

The temperature at which the crystal is dissolved is not particularly limited, and is typically 0 to 100° C., preferably 10 to 80° C., and more preferably 20 to 60° C.

The time period for step (J) is not particularly limited, and is typically 0.1 to 100 hours, preferably 0.5 to 50 hours, and more preferably 1 to 2 hours.

2-4. Step (K)

Step (K) is a step of adding a poor solvent to the solution obtained in step (J) to perform recrystallization.

The poor solvent for use in step (K) may be any solvent that can precipitate a crystal from the solution obtained in step (J). Specifically, the poor solvent can be any solvent that is poorer than the solvent used in step (J) (good solvent). Examples of poor solvents include ketone solvents (e.g., acetone, methyl ethyl ketone, and methyl isobutyl ketone), ether solvents (e.g., diethyl ether, diisopropyl ether, tetrahydrofuran (THF), and 1,4-dioxane), aromatic hydrocarbon solvents (e.g., benzene, toluene, and xylene), aliphatic or alicyclic hydrocarbon solvents (e.g., n-pentane, n-hexane, cyclohexane, and petroleum ether), ester solvents (e.g., methyl acetate, ethyl acetate, isopropyl acetate, and butyl acetate), halogenated hydrocarbon solvents (e.g., methylene chloride, chloroform, and 1,2-dichloroethylene), and alcohol solvents having 3 or more carbon atoms (e.g., 1-propanol).

The solvent for use in step (K) may be any solvent that is poorer than the solvent used in step (J) (good solvent). For example, if the solvent used in step (K) is methanol, an alcohol solvent having 3 or more carbon atoms (e.g., 1-propanol) can be used as a poor solvent. The organic solvents may be used singly or in a combination of two or more. Of these organic solvents, ketone solvents are preferable, and in particular, acetone, methyl ethyl ketone, and methyl isobutyl ketone are preferable.

The amount of the poor solvent for use can be suitably selected from a wide range. For example, the amount of the poor solvent is typically 1 to 30 liters, and preferably 2 to 5 liters, per mole of 2ccPA.

The temperature at which the poor solvent is added is typically −20° C. to 30° C., preferably −10° C. to 20° C., and more preferably 0° C. to 20° C.

The crystal of the cyclic phosphonic acid sodium salt (2ccPA) obtained by the production method comprising step (H) and step (I) or the production method comprising step (H) to step (K) has advantages in its high purity and excellent storage stability.

3. Method for Producing Cyclic Phosphonic Acid Ester Represented by Formula (9)

The cyclic phosphonic acid ester represented by formula (9) of the present invention is produced through the steps illustrated in the following reaction scheme-3:

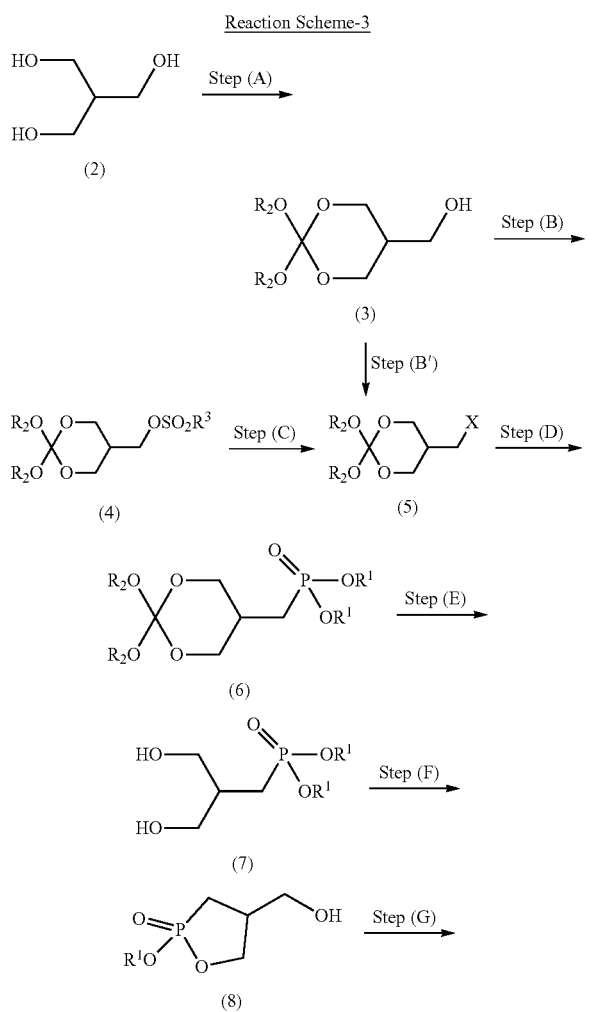

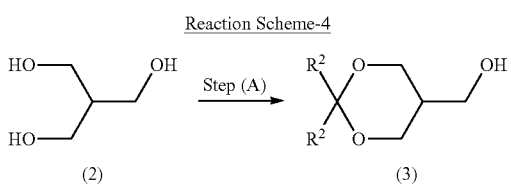

wherein $R^1$, $R^2$, $R^3$, and X are as defined above.

The following describes step (A) to step (G) in detail.

3-1. Step (A): Acetal Protection Step

Step (A) is illustrated in the following reaction scheme-4:

wherein $R^2$ is as defined above.

Specifically, step (A) is a step of reacting 2-hydroxymethyl-1,3-propanediol represented by formula (2) with a ketone compound or acetal compound in the presence of an acid to produce a cyclic acetal compound represented by formula (3) (acetal protection step).

The ketone compound for use in step (A) is not particularly limited, as long as the ketone compound is an organic compound having the keto group. Examples of the ketone compounds include a ketone compound represented by formula (10):

wherein $R^2$ is as defined above; and two $R^2$ groups may be bonded together to form alkylene, and the alkylene may be further substituted or unsubstituted.

The acetal compound for use in step (A) is not particularly limited. Examples include an acetal compound represented by the following formula (11):

$$\underset{R^2\quad R^2}{R^4O\diagdown\diagup OR^4} \quad (11)$$

wherein $R^2$ is as defined above; two $R^2$ groups may be bonded together to form alkylene, and the alkylene may be further substituted or unsubstituted; and two $R^4$ groups are the same or different and represent alkyl.

In the ketone compound represented by formula (10) or the acetal compound represented by formula (11), the alkyl represented by $R^2$ is, for example, linear or branched alkyl having 1 to 10 carbon atoms. Specific examples include methyl, ethyl, n-propyl, isopropyl, n-butyl, isobutyl, s-butyl, t-butyl, n-pentyl, n-hexyl, n-heptyl, n-octyl, and n-nonyl. The alkyl is preferably alkyl having 1 to 6 carbon atoms, more preferably alkyl having 1 to 4 carbon atoms, and particularly preferably methyl, ethyl, and isopropyl. The alkyl may contain 1 to 5 substituents, and preferably 1 to 3 substituents, such as halogen atoms (e.g., fluorine, chlorine, and bromine), aryl (e.g., phenyl and naphthyl), and carboxyl.

In the ketone compound represented by formula (10) or the acetal compound represented by formula (11), the cycloalkyl of the cycloalkyl that may be substituted or unsubstituted and represented by $R^2$ may be, for example, cycloalkyl having 3 to 10 carbon atoms. Specific examples include cyclopropyl, cyclobutyl, cyclopentyl, cyclohexyl, cycloheptyl, and cyclooctyl. The cycloalkyl is preferably cycloalkyl having 3 to 7 carbon atoms, more preferably cycloalkyl having 5 to 7 carbon atoms, and particularly preferably cyclohexyl. The cycloalkyl may contain 1 to 5 substituents, and preferably 1 to 3 substituents, such as halogen atoms (e.g., fluorine, chlorine, and bromine), alkyl (alkyl having 1 to 6 carbon atoms), aryl (e.g., phenyl and naphthyl), and carboxyl.

In the ketone compound represented by formula (10) or the acetal compound represented by formula (11), the aryl of the aryl that may be substituted or unsubstituted and represented by $R^2$ may be, for example, monocyclic, dicyclic, or more than dicyclic aryl. Specific examples include phenyl, naphthyl, anthryl, and phenanthryl. Of these, substituted or unsubstituted phenyl is preferable. The aryl may contain 1 to 5 substituents, and preferably 1 to 3 substituents, such as halogen atoms (e.g., fluorine, chlorine, and bromine), alkyl (alkyl having 1 to 6 carbon atoms), and carboxyl.

In formula (10) or (11), two R groups may be bonded together to form alkylene, and the alkylene may be substituted or unsubstituted. When two $R^2$ groups are bonded together to form alkylene, the alkylene is, for example, —$(CH_2)_q$— wherein q is an integer of 1 to 6, —(CH=CH)$_r$— wherein r represents 1, 2 or 3, or —CH=CH—$(CH_2)_s$— wherein s represents 1, 2 or 3.

The alkylene may be substituted or unsubstituted, and examples of the substituents include alkyl (e.g., alkyl having 1 to 6 carbon atoms), aryl (e.g., phenyl and naphthyl), oxo (=O), and halogen atoms (e.g., fluorine, chlorine, bromine, and iodine). A divalent hydrocarbon group may contain 1 to 5 substituents selected from the group consisting of these substituents.

In the acetal compound represented by formula (11), the alkyl represented by $R^4$ is, for example, linear or branched alkyl having 1 to 10 carbon atoms. Specific examples include methyl, ethyl, n-propyl, isopropyl, n-butyl, isobutyl, s-butyl, t-butyl, n-pentyl, n-hexyl, n-heptyl, n-octyl, and n-nonyl. The alkyl is preferably alkyl having 1 to 6 carbon atoms, more preferably alkyl having 1 to 4 carbon atoms, and particularly preferably methyl, ethyl, and isopropyl. The alkyl may contain 1 to 5 substituents, and preferably 1 to 3 substituents, such as halogen atoms (e.g., fluorine, chlorine, and bromine), aryl (e.g., phenyl and naphthyl), and carboxyl.

Specific examples of the ketone compound for use in step (A) include linear aliphatic ketone compounds having 3 to 20 carbon atoms, such as acetone, 2-butanone (methyl ethyl ketone), 2-pentanone, 3-pentanone, 4-methyl-2-pentanone, methyl isopropyl ketone, methyl isobutyl ketone, 2-hexanone, 3-hexanone, 2-heptanone, 3-heptanone, 2-octanone, 3-octanone, 2-nonanone, 2-decanone, 4-decanone, 2-undecanone, and 6-undecanone; alicyclic ketone compounds having 6 to 20 carbon atoms, such as 2-methylcyclohexanone, 3-methylcyclohexanone, 3-methyl cyclopentanone, and 4-acetyl-1-methylcyclohexene; aromatic ketone compounds having 6 to 20 carbon atoms, such as acetophenone, 1-(4-chlorophenyl)-1-ethanone, 1-(2-chlorophenyl)-1-ethanone, 1-(4-fluorophenyl)-1-ethanone, 1-(2-fluorophenyl)-1-ethanone, 1-(4-methylphenyl)-1-ethanone, 1-(2-methylphenyl)-1-ethanone, 1-(4-nitrophenyl)-1-ethanone, 1-(4-tert-butylphenyl)-1-ethanone, 1-(4-methoxyphenyl)-1-ethanone, 1-(4-allyloxycarbonyl phenyl)-1-ethanone, 1-phenyl-2-propanone, methyl 4-oxo-4-phenylbutanoate, ethyl 4-oxo-4-phenylbutanoate, 1-phenyl-2-butanone, 4-phenyl-2-butanone, 2-phenylcyclopentanone, 2-phenylcycloheptanone, 9-acetylanthracene, 2-acetylbiphenyl, 4-acetylbiphenyl, 2-acetylnaphthalene, 2-acetylphenanthrene, 3-acetylphenanthrene, and 9-acetylphenanthrene; and aralkyl ketone compounds, such as 2-acetyl-5-norbornene.

Of these compounds, acetone, 2-pentanone, 3-pentanone, methyl ethyl ketone, methyl isopropyl ketone, methyl isobutyl ketone, cyclobutanone, cyclopentanone, and cyclohexanone are preferable. Acetone, methyl ethyl ketone, and methyl isobutyl ketone are particularly preferable.

Specific examples of the acetal compound for use in the present invention include 2,2-dimethoxypropane, 2,2-diethoxypropane, 2,2-dipropoxypropane, 2,2-dibutoxypropane, 1,1-dimethoxycyclohexane, 1,1-dimethylcyclopentane, benzophenone dimethyl acetal, 2,2-dimethyl-1,3-dioxolane, 4,4-dimethoxyheptane, 5,5-dimethoxynonane, 4,4-diethoxyheptane, and 5,5-diethoxynonane. Particularly preferable are 2,2-dimethoxypropane, 2,2-dipropoxypropane, 2,2-dibutoxypropane, and benzophenone dimethyl acetal.

The acid for use in step (A) includes known inorganic acids and organic acids. Examples of the inorganic acids include hydrochloric acid and sulfuric acid. Examples of the organic acids include sulfonic acid compounds, such as methanesulfonic acid, trifluoromethanesulfonic acid, benzenesulfonic acid, p-toluenesulfonic acid, and pyridinium p-toluenesulfonate; and carboxylic acid compounds, such as acetic acid. In particular, as the acid, hydrochloric acid, sulfuric acid, p-toluenesulfonic acid, pyridinium p-toluenesulfonate, and acetic acid are preferable. If acetic acid is used, acetic acid can also be used as a solvent.

The amount of the acid for use can be suitably selected from a wide range. For example, the amount of the acid is typically 0.01 to 500 moles, preferably 0.01 to 2 moles, and more preferably 0.01 to 1 mole, per mole of 2-hydroxymethyl-1,3-propanediol represented by formula (2).

Step (A) is performed in the presence or absence of a solvent. When a solvent is used, the solvent is not particularly limited, as long as the solvent does not adversely affect the reaction. Examples of the solvent for use include alcohol solvents (e.g., methanol and ethanol), ether solvents (e.g., diethyl ether, diisopropyl ether, tetrahydrofuran (THF), and 1,4-dioxane), aromatic hydrocarbon solvents (e.g., benzene, toluene, and xylene), aliphatic or alicyclic hydrocarbon solvents (e.g., n-pentane, n-hexane, cyclohexane, and petroleum ether), ester solvents (e.g., ethyl acetate), and halogenated hydrocarbon solvents (e.g., methylene chloride, chloroform, and 1,2-dichloroethylene). These solvents may be used singly or in a combination of two or more. Of these solvents, methanol, THF, 1,4-dioxane, and toluene are preferable, and THF is particularly preferable.

The amount of the solvent for use can be suitably selected from a wide range. For example, the amount of the solvent is typically 0 to 20 liters, and preferably 0 to 5 liters, per mole of the compound represented by formula (2).

Step (A) can be performed in an inert gas atmosphere, such as nitrogen or argon.

The reaction pressure is not particularly limited, and the reaction can be performed under ordinary pressure or increased pressure.

The reaction temperature is typically 0 to 100° C., preferably 10 to 80° C., and more preferably 20 to 80° C.

The reaction time is typically 0.1 to 100 hours, preferably 0.5 to 50 hours, and more preferably 1 to 10 hours.

After completion of the reaction, from the obtained reaction mixture, an excess amount of the reagent (e.g., the ketone compound), the unreacted starting material compound, and other components are removed by a typical separation technique, such as liquid separation, distillation, and column purification to isolate the target cyclic acetal compound represented by formula (3). Alternatively, after completion of the reaction, only concentration may be performed, and the mixture obtained after reaction may be used as it is in step (B) without performing purification and isolation steps (Telescoping synthesis).

3-2. Step (B): Sulfonylation Step

Step (B) is illustrated in the following reaction scheme-5:

Reaction Scheme-5

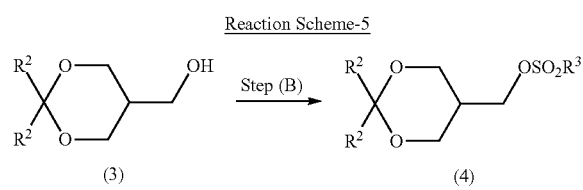

wherein $R^2$ and $R^3$ are as defined above.

Step (B) is a step of reacting the compound represented by formula (3) with a sulfonyl halide compound to obtain the compound represented by formula (4) (sulfonylation step).

For example, step (B) allows the alcohol compound represented by formula (3) to react with a sulfonyl halide compound in an organic solvent in the presence of a base to obtain the sulfonate compound represented by formula (4). For example, to perform the reaction using mesyl chloride as the sulfonyl compound, the method disclosed in Non-patent Literature 2 can be referred to.

Examples of the sulfonyl halide compound for use in step (B) include alkyl sulfonyl halide, such as methyl sulfonyl chloride, methyl sulfonyl bromide, and methyl sulfonyl iodide; and aryl sulfonyl halide, such as phenyl sulfonyl chloride and tosyl chloride.

The amount of the sulfonyl halide compound for use can be suitably selected from a wide range. For example, the amount of the sulfonyl halide compound is typically 1 to 500 moles, preferably 1 to 10 moles, and more preferably 1 to 2 moles, per mole of the methanol compound represented by formula (3).

Step (B) is performed in the presence or absence of a solvent. When a solvent is used, the solvent is not particularly limited, as long as the solvent does not adversely affect the reaction. Examples of the solvent for use include alcohol solvents (e.g., methanol and ethanol), ether solvents (e.g., diethyl ether, diisopropyl ether, tetrahydrofuran (THF), and 1,4-dioxane), aromatic hydrocarbon solvents (e.g., benzene, toluene, and xylene), aliphatic or alicyclic hydrocarbon solvents (e.g., n-pentane, n-hexane, cyclohexane, and petroleum ether), ester solvents (e.g., ethyl acetate), halogenated hydrocarbon solvents (e.g., methylene chloride (MDC, DCM), chloroform, and 1,2-dichloroethylene). These solvents may be used singly or in a combination of two or more. Of these solvents, THF, 1,4-dioxane, toluene, and methylene chloride are preferable, and methylene chloride is particularly preferable.

The amount of the solvent for use can be suitably selected from a wide range. For example, the amount of the solvent is typically 0 to 20 liters, and preferably 1 to 5 liters, per mole of the compound represented by formula (2).

Step (B) can be performed in an inert gas atmosphere, such as nitrogen or argon.

The reaction pressure is not particularly limited, and the reaction can be performed under ordinary pressure or increased pressure.

The reaction temperature is typically −40 to 100° C., preferably −30 to 80° C., and more preferably −20 to 20° C.

The reaction time is typically 0.1 to 100 hours, preferably 0.5 to 50 hours, and more preferably 1 to 4 hours.

After completion of the reaction, from the obtained reaction mixture, an excess amount of the reagent (e.g., the sulfonyl halide compound), the unreacted starting material compound, and other components are removed by a typical separation technique, such as liquid separation, concentration, and column purification to isolate the target cyclic acetal compound represented by formula (4). Alternatively, after completion of the reaction, only liquid separation and concentration may be performed, and the mixture obtained after reaction may be used as it is in step (C) without performing purification and isolation steps (Telescoping synthesis).

3-3. Step (C): Halogenation Step

Step (C) is illustrated in the following reaction scheme-6:

Reaction Scheme-6

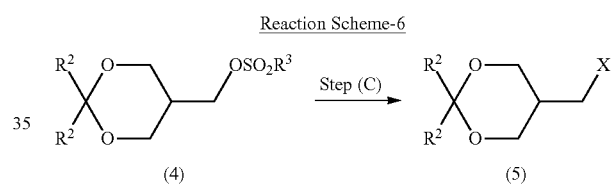

wherein $R^2$, $R^3$, and X are as defined above.

Specifically, step (C) is a step of reacting the compound represented by formula (4) with an alkali metal halide and/or an alkaline-earth metal halide in the presence of a base to obtain the compound represented by formula (5) (halogenation step).

The alkali metal halide for use in step (C) is not particularly limited. Examples include lithium halides (e.g., lithium fluoride, lithium chloride, lithium bromide, and lithium iodide), sodium halides (e.g., sodium fluoride, sodium chloride, sodium bromide, and sodium iodide), potassium halides (e.g., potassium fluoride, potassium chloride, potassium bromide, and potassium iodide), and cesium halides (e.g., cesium fluoride, cesium chloride, cesium bromide, and cesium iodide). Of these, sodium iodide is preferable. These alkali metal halides may be used singly or in a combination of two or more.

The alkaline-earth metal halide for use in step (C) is not particularly limited. Examples include magnesium halides (e.g., magnesium fluoride, magnesium chloride, magnesium bromide, and magnesium iodide), calcium halides (e.g., calcium fluoride, calcium chloride, calcium bromide, and calcium iodide), strontium halides (e.g., strontium fluoride, strontium chloride, strontium bromide, and strontium iodide), and barium halides (e.g., barium fluoride, barium chloride, barium bromide, and barium iodide). These alkaline-earth metal halides may be used singly or in a combination of two or more.

The amount of the alkali metal halide and/or alkaline-earth metal halide for use is typically 1 mole or more, preferably 1 to 10 moles, and more preferably 1 to 3 moles, per mole of the compound represented by formula (4).

Examples of the base for use in step (C) include organic bases and inorganic bases.

Examples of the organic bases include organic amines containing 1 to 3, preferably 3 alkyl groups having 1 to 4 carbon atoms, such as trimethylamine, triethylamine, tributylamine, and diisopropylethylamine. In particular, triethylamine is preferable.

Specific examples of the inorganic bases include carbonates of alkali metals or alkaline-earth metals, such as sodium hydrogen carbonate, sodium carbonate, potassium hydrogen carbonate, potassium carbonate, and calcium carbonate. In particular, sodium hydrogen carbonate is preferable.

The amount of the base for use may be the catalytic amount. For example, the amount of the base is typically 0.01 moles or more, preferably 0.01 to 1 mole, and more preferably 0.05 to 0.5 moles, per mole of the sulfonate compound represented by formula (4).

In step (C), adding a catalytic amount of a base prevents decomposition to thereby produce the halogen compound represented by formula (5) at a high yield.

Step (C) is performed in the presence or absence of a solvent. When a solvent is used, the solvent is not particularly limited, as long as the solvent does not adversely affect the reaction. Examples of the solvent for use include ketone solvents (e.g., acetone, methyl ethyl ketone, and methyl isobutyl ketone), alcohol solvents (e.g., methanol and ethanol), ether solvents (e.g., diethyl ether, diisopropyl ether, tetrahydrofuran (THF), and 1,4-dioxane), aromatic hydrocarbon solvents (e.g., benzene, toluene, and xylene), aliphatic or alicyclic hydrocarbon solvents (e.g., n-pentane, n-hexane, cyclohexane, and petroleum ether), ester solvents (e.g., ethyl acetate), and halogenated hydrocarbon solvents (e.g., methylene chloride, chloroform, and 1,2-dichloroethylene). These solvents may be used singly or in a combination of two or more. Of these solvents, acetone, methyl ethyl ketone, and methyl isobutyl ketone are particularly preferable.

The amount of the solvent for use can be suitably selected from a wide range. For example, the amount of the solvent is typically 0 to 20 liters, and preferably 1 to 5 liters, per mole of the compound represented by formula (4).

Step (C) can be performed in an inert gas atmosphere, such as nitrogen or argon.

The reaction pressure is not particularly limited, and the reaction can be performed under ordinary pressure or increased pressure.

The reaction temperature is typically 0 to 120° C., preferably 10 to 100° C., and more preferably 55 to 80° C.

The reaction time is typically 0.1 to 100 hours, preferably 0.5 to 50 hours, and more preferably 1 to 18 hours.

This reaction is a novel reaction that uses a base in halogenation.

After completion of the reaction, from the obtained reaction mixture, an excess amount of the reagent (e.g., the alkali metal halide, alkaline-earth metal, and base), the unreacted starting material compound, and other components are removed by a typical separation technique, such as liquid separation, concentration, and column purification to isolate the target compound represented by formula (5). Alternatively, after completion of the reaction, the mixture obtained after reaction may be used as it is in step (D) without performing purification and isolation steps (Telescoping synthesis).

3-4. Step (B'): Another Halogenation Step

Step (B') is illustrated in the following reaction scheme-7:

Reaction Scheme-7

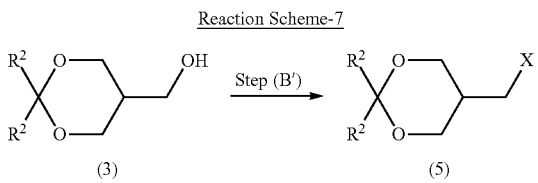

(3)  (5)

wherein R and X are as defined above.

Specifically, step (B') is a step of reacting the cyclic acetal compound represented by formula (3) with a halogenating agent.

The halogenating agent for use in step (B') is not particularly limited. Examples of the halogenating agent for chlorination include chlorine, thionyl chloride, phosphorus trichloride, phosphorus pentachloride, triphenylphosphine-carbon tetrachloride, and triphenylphosphine-N-chlorosuccinimide. Examples of the halogenating agent for bromination include bromine, hydrobromic acid, phosphorus tribromide, triphenylphosphine-bromine, triphenylphosphine-N-bromosuccinimide, triphenylphosphine-carbon tetrabromide, and thionyl bromide. Examples of the halogenating agent for iodination include iodine, triphenylphosphine-iodine, and triphenylphosphine-N-iodosuccinimide. Of these, triphenylphosphine-iodine and triphenylphosphine-carbon tetrabromide are preferable.

The amount of the halogenating agent for use is typically 1 to 500 moles, preferably 1 to 10 moles, and more preferably 1 to 2 moles, per mole of the alcohol compound represented by formula (3).

The reaction of step (B') can be performed in the presence of imidazole to scavenge the acid generated in the reaction.

The amount of imidazole for use is typically 1 to 500 moles, preferably 1 to 10 moles, and more preferably 1 to 2 moles, per mole of the cyclic acetal compound represented by formula (3).

Step (B') is performed in the presence or absence of a solvent. When a solvent is used, the solvent is not particularly limited, as long as the solvent does not adversely affect the reaction. Examples of the solvent for use include ketone solvents (e.g., acetone, methyl ethyl ketone, and methyl isobutyl ketone), alcohol solvents (e.g., methanol and ethanol), ether solvents (e.g., diethyl ether, diisopropyl ether, cyclopentyl methyl ether (CPME), tetrahydrofuran (THF), and 1,4-dioxane), aromatic hydrocarbon solvents (e.g., benzene, toluene, and xylene), aliphatic or alicyclic hydrocarbon solvents (e.g., n-pentane, n-hexane, cyclohexane, and petroleum ether), ester solvents (e.g., ethyl acetate), and halogenated hydrocarbon solvents (e.g., methylene chloride, chloroform, and 1,2-dichloroethylene). These solvents may be used singly or in a combination of two or more. Of these solvents, acetone, methyl ethyl ketone, and methyl isobutyl ketone are particularly preferable.

The amount of the solvent for use can be suitably selected from a wide range. For example, the amount of the solvent is typically 0 to 20 liters, and preferably 1 to 5 liters, per mole of the compound represented by formula (4).

Step (B') can be performed in an inert gas atmosphere, such as nitrogen or argon.

The reaction pressure is not particularly limited, and the reaction can be performed under ordinary pressure or increased pressure.

The reaction temperature is typically 0 to 100° C., preferably 0 to 40° C., and more preferably 0 to 20° C.

The reaction time is typically 0.1 to 100 hours, preferably 0.5 to 50 hours, and more preferably 1 to 5 hours.

After completion of the reaction, from the obtained reaction mixture, an excess amount of the reagent (e.g., the halogenating agent), the unreacted starting material compound, and other components are removed by a typical separation technique, such as liquid separation, concentration, and column purification to isolate the target compound represented by formula (5). Alternatively, after completion of the reaction, the mixture obtained after reaction may be used as it is in step (D) without performing purification and isolation steps (Telescoping synthesis).

3-5. Step (D): Phosphonate Diesterification Step

Step (D) is illustrated in the following reaction scheme-8:

Reaction Scheme-8

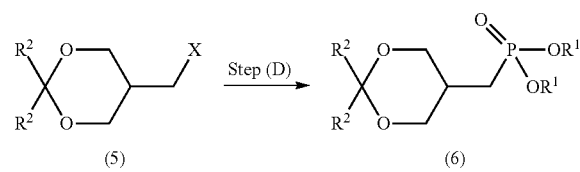

(5) (6)

wherein $R^1$, $R^2$, and X are as defined above.

Specifically, step (D) is a step of reacting the compound represented by formula (5) with a phosphorous acid diester in the presence of a base to obtain the compound represented by formula (6) (phosphonate diesterification step).

Examples of the phosphorous acid diester for use in step (D) include a compound represented by the following formula (12):

(12)

wherein $R^1$ is as defined above.

In the phosphorous acid diester represented by formula (12), alkyl, arylalkyl, or aryl represented by $R^1$ is the same as alkyl, arylalkyl, or aryl represented by $R^1$ in the cyclic phosphonic acid ester represented by formula (9).

Specific examples of phosphorous acid diester include dialkyl phosphite, such as dimethyl phosphite, diethyl phosphite, dipropyl phosphite, dibutyl phosphite, diisopropyl phosphite, and methylethyl phosphite; diarylalkyl phosphite, such as dibenzyl phosphite, and di(phenylethyl) phosphite; and diaryl phosphite, such as diphenyl phosphite, and ditolyl phosphite. Preferable are dimethyl phosphite, diethyl phosphite, dibenzyl phosphite, and diphenyl phosphite.

The amount of the phosphorous acid diester for use is not particularly limited. For example, the amount is preferably 1 to 10 equivalents, and particularly preferably 2 to 2.5 equivalents, per equivalent of the halogen compound represented by formula (5).

The solvent for use in step (D) is not particularly limited, as long as the solvent is an organic solvent. For example, an aprotic polar solvent can be used. Examples of the aprotic polar solvent include amide solvents, such as N,N-dimethylformamide (DMF), N,N-dimethylacetamide (DMAc), N-methylpyrrolidone (NMP), and 1,3-dimethyl-2-imidazolidinone; dimethyl sulfoxide (DMSO), hexamethylphosphoric triamide (HMPA), acetonitrile (AN), acetone, and THF. DMF, DMAc, and acetonitrile are particularly preferable. These solvents may be used singly or in a combination of two or more.

The amount of the solvent for use can be suitably selected from a wide range. For example, the amount of the solvent is typically 0 to 20 liters, and preferably 1 to 5 liters, per mole of the compound represented by formula (5).

Examples of the base for use in step (D) include organic bases and inorganic bases.

Examples of the organic bases include organic amines containing 1 to 3, preferably 3 alkyl groups having 1 to 4 carbon atoms, such as trimethylamine, triethylamine, tributylamine, and diisopropylethylamine. Triethylamine is particularly preferable.

Specific examples of the inorganic bases include carbonates of alkali metals or alkaline-earth metals, such as sodium hydrogen carbonate, sodium carbonate, potassium hydrogen carbonate, potassium carbonate, rubidium carbonate, calcium carbonate, and cesium carbonate. Cesium carbonate and rubidium carbonate are particularly preferable.

The amount of the base for use is not particularly limited. The amount is preferably 1 to 10 equivalents, and particularly preferably 2 to 2.5 equivalents, per equivalent of the compound represented by formula (5).

Step (D) can be performed in an inert gas atmosphere, such as nitrogen or argon.

The reaction pressure is not particularly limited, and the reaction can be performed under ordinary pressure or increased pressure.

The reaction temperature is typically 0 to 120° C., preferably 20 to 80° C., and more preferably 40 to 50° C.

The reaction time is typically 0.1 to 100 hours, preferably 0.5 to 50 hours, and more preferably 5 to 8 hours.

After completion of the reaction, from the obtained reaction mixture, an excess amount of the reagent (e.g., the phosphorous acid diester and base), the unreacted starting material compound, and other components are removed by a typical separation technique, such as concentration, filtration, and column purification to isolate the target compound represented by formula (6). Alternatively, after completion of the reaction, only concentration and filtration may be performed, and the mixture obtained after reaction may be used as it is in step (E) without performing purification and isolation steps (Telescoping synthesis).

3-6. Step (E): Ring-Opening Step

Step (E) is illustrated in the following reaction scheme-9:

Reaction Scheme-9

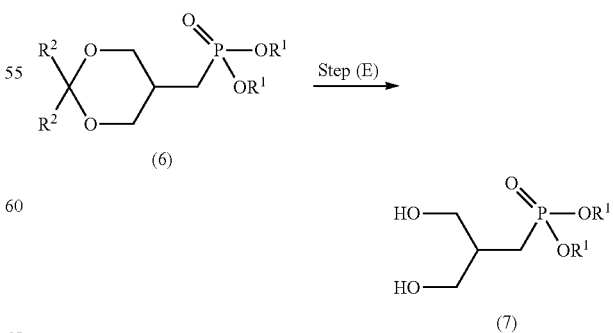

wherein $R^1$ and R are as defined above.

Specifically, step (E) is a step of allowing an acid to act on the compound represented by formula (6) to obtain the compound represented by formula (7) (ring-opening step).

Any known organic acids or inorganic acids can be used as the acid. Examples of the organic acids include sulfonic acids, such as p-toluenesulfonic acid (p-TsOH), pyridinium p-toluenesulfonate (PPTS), and camphorsulfonic acid (CSA); and lower fatty acids having 1 to 4 carbon atoms, such as formic acid, acetic acid, propionic acid, butyric acid, and trifluoroacetic acid (TFA). p-TsOH and CSA are particularly preferable.

Specific examples of the inorganic acids include hydrochloric acid, sulfuric acid, and nitric acid. Hydrochloric acid is particularly preferable.

The amount of the acid for use is not particularly limited. The amount is preferably 0.01 to 0.2 moles, and particularly preferably 0.01 to 0.1 moles, per mole of the compound represented by formula (6).

Step (E) is performed in the presence or absence of a solvent. When a solvent is used, the solvent is not particularly limited, as long as the solvent does not adversely affect the reaction. Examples of the solvent for use include water, alcohol solvents (e.g., lower alcohols having 1 to 4 carbon atoms, such as methanol, ethanol, n-propanol, isopropanol, and n-butanol), ether solvents (e.g., diethyl ether, diisopropyl ether, tetrahydrofuran (THF), and 1,4-dioxane), aromatic hydrocarbon solvents (e.g., benzene, toluene, and xylene), aliphatic or alicyclic hydrocarbon solvents (e.g., n-pentane, n-hexane, cyclohexane, and petroleum ether), ester solvents (e.g., ethyl acetate), halogenated hydrocarbon solvents (e.g., methylene chloride, chloroform, and 1,2-dichloroethylene). These solvents may be used singly or in a combination of two or more. Of these solvents, methanol, THF, 1,4-dioxane, and toluene are preferable, and methanol is particularly preferable.

The amount of the solvent for use can be suitably selected from a wide range. For example, the amount of the solvent is typically 0 to 20 liters, and preferably 1 to 5 liters, per mole of the compound represented by formula (6).

Step (E) can be performed in an inert gas atmosphere, such as nitrogen or argon.

The reaction pressure is not particularly limited, and the reaction can be performed under ordinary pressure or increased pressure.

The reaction temperature is typically 0 to 120° C., preferably 0 to 80° C., and more preferably 0 to 20° C.

The reaction time is typically 0.1 to 100 hours, preferably 0.5 to 50 hours, and more preferably 3 to 12 hours.

After completion of the reaction, from the obtained reaction mixture, an excess amount of the reagent (e.g., the acid), the unreacted starting material compound, and other components are removed by a typical separation technique, such as concentration and column purification to isolate the target compound represented by formula (7). Alternatively, after completion of the reaction, only concentration may be performed, and the mixture obtained after reaction may be used as it is in step (F) without performing purification and isolation steps (Telescoping synthesis).

3-7. Step (F): Cyclization Step

Step (F) is illustrated in the following reaction scheme-10:

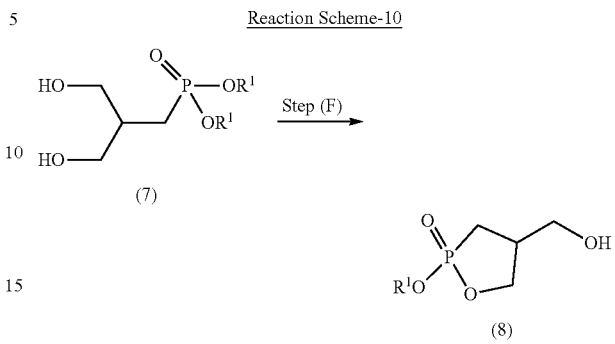

Reaction Scheme-10 wherein $R^1$ is as defined above.

Specifically, step (F) is a step of allowing a base to act on the compound represented by formula (7) to obtain the compound of formula (8) (cyclization step).

Any known organic bases or inorganic bases can be used as the base for use in step (F). Examples of the organic bases include tertiary organic amines, such as diazabicycloundecene (DBU), diazabicyclononene (DBN), trimethylamine, triethylamine (TEA), tributylamine, and diisopropylethylamine (DIPEA); and metal alkoxides, such as sodium methoxide (NaOMe), sodium ethoxide (NaOEt), potassium t-butoxide (t-BuOK), and sodium t-butoxide (t-BuONa).

Examples of the inorganic bases include alkali metal carbonates, such as cesium carbonate ($Cs_2CO_3$), and rubidium carbonate ($Rb_2CO_3$); and alkali metal hydrides, such as sodium hydride (NaH).

The base is preferably DBU, DBN, TEA, DIPEA, NaOMe, NaOEt, t-BuOK, t-BuONa, $Cs_2CO_3$, and NaH, and more preferably DBU and DBN.

The amount of the base for use is not particularly limited. For example, the amount of the base is preferably 0.1 to 2 moles, and particularly preferably 0.1 to 1 mole, per mole of the compound represented by formula (7).

Step (F) is performed in the presence or absence of a solvent. When a solvent is used, the solvent is not particularly limited, as long as the solvent does not adversely affect the reaction. Examples of the solvent for use include water, alcohol solvents (e.g., lower alcohols having 1 to 4 carbon atoms, such as methanol, ethanol, n-propanol, isopropanol, and n-butanol); ether solvents (e.g., diethyl ether, diisopropyl ether (IPA), tetrahydrofuran (THF), and 1,4-dioxane); aromatic hydrocarbon solvents (e.g., benzene, toluene, and xylene); aliphatic or alicyclic hydrocarbon solvents (e.g., n-pentane, n-hexane, cyclohexane, and petroleum ether); ester solvents (e.g., ethyl acetate); halogenated hydrocarbon solvents (e.g., methylene chloride, chloroform, and 1,2-dichloroethylene); amide solvents (e.g., N,N-dimethylformamide (DMF), N,N-dimethylacetamide (DMAc), N-methylpyrrolidone (NMP), and 1,3-dimethyl-2-imidazolidinone); dimethyl sulfoxide (DMSO); hexamethylphosphoric triamide (HMPA); acetonitrile (AN); and acetone. These solvents may be used singly or in a combination of two or more. Of these solvents, DMF, DMAc, AN, acetone, methanol, IPA, and butanol are preferable, and DMF and DMAc are particularly preferable.

The amount of the solvent for use can be suitably selected from a wide range. For example, the amount of the solvent is typically 0 to 20 liters, and preferably 1 to 5 liters, per mole of the compound represented by formula (7).

In the reaction of step (F), a quenching agent may be used to terminate the reaction. A known quenching agent, including, for example, an organic acid, can be used as the quenching agent. Examples of the organic acid include sulfonic acid, such as p-TsOH and CSA, and fatty acids having 1 to 4 carbon atoms, such as formic acid, acetic acid, propionic acid, butyric acid, and trifluoroacetic acid. p-TsOH and CSA are particularly preferable.

The amount of the quenching agent for use is preferably equimolar to the amount of the organic base added for the reaction.

Step (F) can be performed in an inert gas atmosphere, such as nitrogen or argon.

The reaction pressure is not particularly limited, and the reaction can be performed under ordinary pressure or increased pressure.

The reaction temperature is typically 0 to 60° C., preferably 0 to 40° C., and more preferably 15 to 25° C.

The reaction time is typically 0.1 to 100 hours, preferably 0.5 to 50 hours, and more preferably 2 to 7 hours.

After completion of the reaction, from the obtained reaction mixture, an excess amount of the reagent (e.g., the base), the unreacted starting material compound, and other components are removed by a typical separation technique, such as concentration and column purification to isolate the target compound represented by formula (8). Alternatively, after completion of the reaction, only concentration may be performed, and the mixture obtained after reaction may be used as it is in step (G) without performing purification and isolation steps (Telescoping synthesis).

3-8. Step (G): Esterification Step

Step (G) is illustrated in the following reaction scheme-11:

Reaction Scheme-11 wherein $R^1$ is as defined above.

Specifically, step (G) is a step of reacting the cyclic phosphonic acid compound represented by formula (8) with an oleic acid compound to obtain the compound of formula (9) (esterification step). A known esterification reaction can be suitably applied.

Examples of the oleic acid compound include oleic acid and oleic acid derivatives, such as oleic acid halides, oleic anhydride, and oleic acid esters. These oleic acid compounds may be used singly or in a combination of two or more.

Examples of the halides of the oleic acid halides for use in step (G) include a chlorine atom, a bromine atom and an iodine atom. The halide is particularly preferably a chlorine atom.

Examples of the oleic acid esters for use in step (G) include methyl ester and ethyl ester.

The amount of the oleic acid compound for use is not particularly limited. For example, the amount of the oleic acid compound is preferably 1 to 2 moles, and particularly preferably 1 to 1.5 moles, per mole of the compound represented by formula (8).

Examples of step (G) include:

a reaction of cyclic phosphonic acid compound (8) with an oleic acid in the presence of a condensation agent (step G-1);

a reaction of cyclic phosphonic acid compound (8) with an oleic acid halide in the presence of a base (step G-2);

a reaction of cyclic phosphonic acid compound (8) with an oleic anhydride (step G-3); and a reaction of cyclic phosphonic acid compound (8) with an oleic acid ester (step G-4).

Any known condensation agent can be used in step G-1 without limitation. Examples of the condensation agent include dicyclohexyl carbodiimide (DCC), diisopropyl carbodiimide (DIC), and 1-ethyl-3-(3-dimethylaminopropyl) carbodiimide hydrochloride (EDC).

Examples of the base for use in step G-2 include organic bases, such as triethylamine, pyridine, N,N-diethylaniline, 4-dimethylaminopyridine, and diisopropylethylamine.

Examples of step (G-1) include the following step G-1A to step G-1F:

Step G-1A: a method comprising reacting cyclic phosphonic acid compound (8) with an oleic acid in the presence of the condensation agent;

Step G-1B: a method comprising reacting cyclic phosphonic acid compound (8) with an oleic acid in the presence of 2-chloro-1-methylpyridinium iodide (CMPI);

Step G-1C: a method comprising reacting cyclic phosphonic acid compound (8) with an oleic acid in the presence of (benzotriazol-1-yl-oxy)tripyrrolidinophosphonium hexafluorophosphate (pyBOP);

Step G-1D: a method comprising reacting cyclic phosphonic acid compound (8) with an oleic acid in the presence of O-(7-azabenzotriazol-1-yl)-N,N,N,N-tetramethyluronium hexafluorophosphate (HATU);

Step G-1E: a method comprising reacting cyclic phosphonic acid compound (8) with an oleic acid in the presence of O-(benzotriazol-1-yl)-N,N,N,N-tetramethyluronium hexafluorophosphate (HBTU); and Step G-1F: a method comprising reacting cyclic phosphonic acid compound (8) with an oleic acid in the presence of (1-cyano-2-ethoxy-2-oxoethylidenaminooxy)dimethylamino morpholino carbenium hexafluorophosphate (COMU).

Examples of step (G-2) include the following step G-2A and step G-2B:

Step G-2A: a method comprising reacting cyclic phosphonic acid compound (8) with an oleic acid halide in the presence of triethylamine; and Step G-2B: a method comprising producing an oleic acid halide from an oleic acid and reacting the oleic acid halide with cyclic phosphonic acid compound (8) in the presence of triethylamine.

Examples of step G-3 include the following step G-3A and step G-3B:

Step G-3A: a method comprising reacting cyclic phosphonic acid compound (8) with an oleic anhydride; and Step G-3B: a method comprising reacting an oleic acid with tosyl chloride to generate a mixed acid anhydride in the reaction system and reacting the acid anhydride with cyclic phosphonic acid compound (8).

The condensation agent or base is used in any amount within the range of typically 0.25 moles to an excess amount, and preferably 0.5 to 2 moles, per mole of cyclic phosphonic acid compound (8). The condensation agent or base is suitably selected according to the type of oleic acid compound or its derivative.

Step (G) can be performed in an inert gas atmosphere, such as nitrogen or argon.

The reaction pressure is not particularly limited, and the reaction can be performed under ordinary pressure or increased pressure.

The reaction temperature is typically 0 to 120° C., preferably 0 to 30° C., and more preferably 15 to 25° C.

The reaction time is typically 0.1 to 100 hours, preferably 0.5 to 50 hours, and more preferably 2 to 17 hours.

After completion of the reaction, from the obtained reaction mixture, an excess amount of the reagent (e.g., the oleic acid compound), the unreacted starting material compound, and other components are removed by a typical separation technique, such as liquid separation, concentration, and column purification to isolate the target compound represented by formula (9). Alternatively, after completion of the reaction, only liquid separation and concentration may be performed, and the mixture obtained after reaction may be used as it is in step (H) without performing purification and isolation steps (Telescoping synthesis). The present invention is described in further detail with reference to Synthesis Examples, Examples, and Comparative Examples. However, the present invention is not limited to the following Examples.

Step (A)

Synthesis Example A1: (Step A: $R^2$=n-propyl)

Synthesis of 2,2-di-n-propyl-5-(hydroxymethyl)-1,3-dioxane (3b)

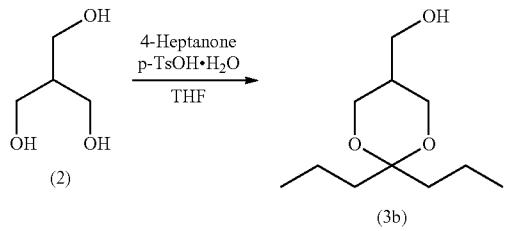

2-Hydroxymethyl-1,3-propanediol (2) (3.0 g) was dissolved in 30 mL of tetrahydrofuran, and 4.74 mL of 4-heptanone and 53.8 mg of p-toluenesulfonic acid monohydrate were added thereto, followed by heating under reflux for 3.5 hours using a Dean-Stark trap. During the reaction, distilled tetrahydrofuran was discarded, and new tetrahydrofuran was added to the reaction mixture. Thereafter, 0.39 mL of triethylamine was added to the reaction mixture to stop the reaction, and tetrahydrofuran was distilled off under reduced pressure. Then, 30 mL of ethyl acetate and 30 mL of water were added to the residue, and the layers were separated. After the organic layer was extracted, the water layer was further extracted twice with 30 mL of ethyl acetate. The combined organic layers were washed with 30 mL of saturated brine, dried over magnesium sulfate, and filtered, followed by distilling-off of ethyl acetate under reduced pressure. The resulting residue was purified with silica gel chromatography (n-hexane:ethyl acetate=1:1) to obtain 2.34 g of acetal compound (3b) (yield: 41%).

$^1$H-NMR (500 MHz, CDCl$_3$):

δ: 0.93 (m, 6H), 1.35 (m, 4H), 1.63 (m, 3H), 1.72 (m, 2H), 1.79 (m, 1H), 3.76 (m, 4H), 4.01 (dd, J=11.9, 4.0 Hz, 2H)

Synthesis Example A2 (Step A: $R^2$=n-Butyl)

Synthesis of 2,2-dibutyl-5-(hydroxymethyl)-1,3-dioxane (3c)

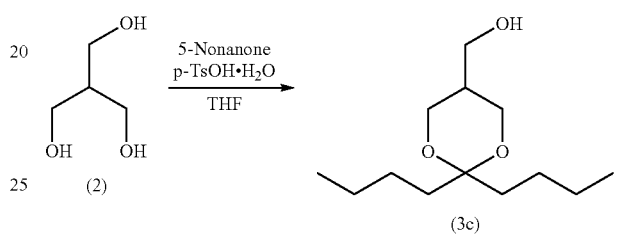

2-Hydroxymethyl-1,3-propanediol (2) (1.0 g) was dissolved in 9.5 mL of tetrahydrofuran, and 1.96 mL of 5-nonanone and 17.9 mg of p-toluenesulfonic acid monohydrate were added thereto, followed by heating under reflux for 17 hours. Thereafter, 0.13 mL of triethylamine was added to the reaction mixture to stop the reaction, and tetrahydrofuran was distilled off under reduced pressure. Then, 10 mL of ethyl acetate and 10 mL of water were added to the residue, and the layers were separated. After the organic layer was extracted, the aqueous layer was further extracted twice with 10 mL of ethyl acetate. The combined organic layers were washed with 10 mL of saturated brine, dried over magnesium sulfate, and filtered, followed by distilling-off of ethyl acetate under reduced pressure. The resulting residue was purified with silica gel chromatography (n-hexane:ethyl acetate=1:1) to obtain 156 mg of acetal compound (3c) (yield: 7%).

$^1$H-NMR (500 MHz, CDCl$_3$):

δ: 0.92 (m, 6H), 1.31 (m, 8H), 1.50 (t, J=5.1 Hz, 1H), 1.65 (m, 2H), 1.74 (m, 2H), 1.80 (m, 1H), 3.76 (m, 4H), 4.01 (dd, J=12.1, 4.1 Hz, 2H)

Synthesis Example A3 (Step A: $R^2$=Phenyl)

Synthesis of 2,2-diphenyl-5-(hydroxymethyl)-1,3-dioxane (3d)

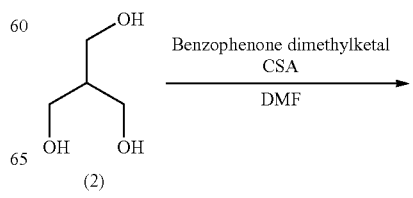

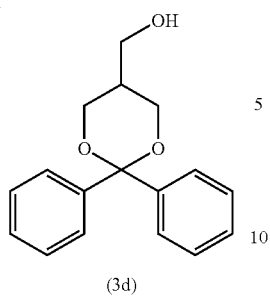

(3d)

2-Hydroxymethyl-1,3-propanediol (2) (1.0 g) was dissolved in 48 mL of DMF, and 2.58 g of benzophenone dimethyl acetal and 656 mg of CSA were added thereto, followed by stirring at 40° C. under reduced pressure for 22.5 hours. DMF in the reaction mixture was distilled off under reduced pressure, 10 mL of ethyl acetate and 10 mL of water were added to the residue, and the layers were separated. After the organic layer was extracted, the aqueous layer was further extracted twice with 10 mL of ethyl acetate. The combined organic layers were washed with 10 mL of saturated brine, dried over magnesium sulfate, and filtered, followed by distilling-off of ethyl acetate under reduced pressure. The resulting residue was purified with silica gel chromatography (n-hexane:ethyl acetate=1:1) to obtain 647 mg of acetal compound (3d) (yield: 25%).

$^1$H-NMR (500 MHz, CDCl$_3$)

δ: 1.94 (m, 1H), 3.81 (dd, J=7.0, 5.2 Hz, 2H), 3.91 (dd, J=11.8, 5.5 Hz, 2H), 4.14 (dd, J=11.8, 3.8 Hz, 2H), 7.25 (m, 2H), 7.34 (m, 4H), 7.51 (m, 4H)

Step (B)

Synthesis Example B1 (Step B: R$^2$=Methyl)

Synthesis of 2,2-dimethyl-5-methanesulfonyloxymethyl-1,3-dioxane (4a)

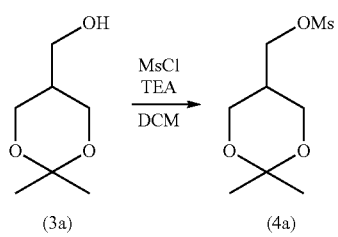

2,2-Dimethyl-5-(hydroxymethyl)-1,3-dioxane (3a) (5.00 g) was dissolved in 67 mL of CH$_2$Cl$_2$, and 5.42 mL of triethylamine was added thereto, followed by cooling to −20° C. Further, 2.56 mL of mesyl chloride (MsCl) was added, and the resulting mixture was stirred at −20° C. for 1 hour. Thereafter, 50 mL of water was added to the reaction mixture to stop the reaction, and extraction was performed twice with 40 mL of CH$_2$Cl$_2$. After the separated organic layers were washed with water, CH$_2$Cl$_2$ was distilled off under reduced pressure, and the resulting residue was purified with silica gel chromatography (n-hexane:ethyl acetate=1:1) to obtain 6.22 g of compound (4a) (yield: 92%).

$^1$H-NMR (500 MHz, CDCl$_3$):

δ: 1.39 (s, 3H), 1.46 (s, 3H), 2.00 (m, 1H), 3.04 (s, 3H), 3.78 (dd, 2H, J=12, 3 Hz), 4.08 (dd, 2H, J=11.5, 2.5 Hz), 4.42 (d, 2H, J=7 Hz)

Synthesis Example B2 (Step B: R$^2$=n-Propyl)

Synthesis of 2,2-di-n-propyl-5-methanesulfonyloxymethyl-1,3-dioxane (4b)

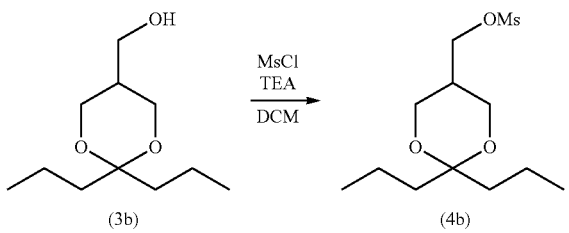

The compound (3b) obtained in Synthesis Example A1 (1.0 g) was dissolved in 20 mL of CH$_2$Cl$_2$, and 1.03 mL of triethylamine was further added thereto, followed by cooling to −20° C. Thereafter, 0.459 mL of MsCl was added to the reaction solution and stirred at −20° C. for 1 hour. Then, 20 mL of water was added to the resulting reaction mixture to stop the reaction, and extraction was performed twice with 20 mL of CH$_2$Cl$_2$, followed by washing with 20 mL of saturated brine. After the resulting product was dried over magnesium sulfate and filtered, CH$_2$Cl$_2$ was distilled off under reduced pressure, and the resulting residue was purified with silica gel chromatography (n-hexane:ethyl acetate=3:1) to obtain 1.27 g of compound (4b) (yield: 92%).

$^1$H-NMR (500 MHz, CDCl$_3$)

δ: 0.93 (m, 6H), 1.36 (m, 4H), 1.58 (m, 1H), 1.76 (m, 2H), 1.95 (m, 1H), 3.04 (s, 3H), 3.74 (dd, J=12.4, 3.3 Hz, 2H), 4.08 (dd, J=15.6, 3.3 Hz, 2H), 4.43 (d, J=7.5 Hz, 2H)

Synthesis Example B3 (Step B: R$^2$=n-Butyl)

Synthesis of 2,2-di-n-butyl-5-methanesulfonyloxymethyl-1,3-dioxane (4c)

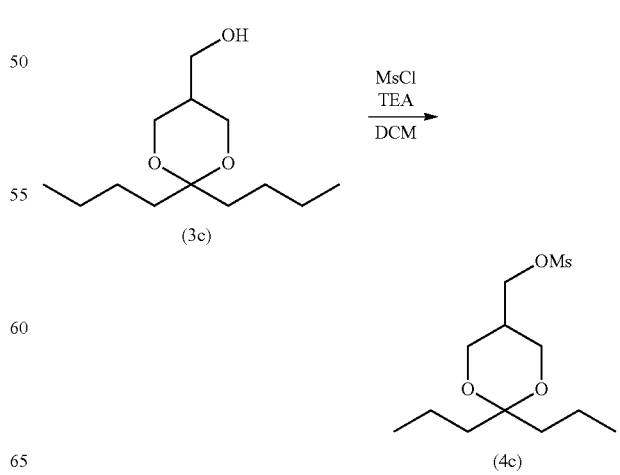

The compound (3c) obtained in Synthesis Example A2 (156 mg) was dissolved in 2.7 mL of $CH_2Cl_2$, and 0.14 mL of triethylamine was further added thereto, followed by cooling to −20° C. Thereafter, 0.062 mL of MsCl was added thereto, and the mixture was stirred at −20° C. for 1 hour. Then, 1.8 mL of water was added to the resulting reaction mixture to stop the reaction, extraction was performed twice with 1.8 mL of $CH_2Cl_2$, and the organic layers were washed with 1.8 mL of saturated brine. After the resulting product was dried over magnesium sulfate and filtered, $CH_2Cl_2$ was distilled off under reduced pressure, and the resulting residue was purified with silica gel chromatography (n-hexane:ethyl acetate=3:1) to obtain 169 mg of compound (4c) (yield: 81%).

$^1$H-NMR (500 MHz, $CDCl_3$)

δ: 0.92 (m, 6H), 1.30 (m, 8H), 1.61 (m, 2H), 1.78 (m, 2H), 1.96 (m, 1H), 3.04 (s, 3H), 3.74 (dd, J=12.6, 3.6 Hz, 2H), 4.08 (dd, J=12.5, 3.5 Hz, 2H), 4.43 (d, J=7.4 Hz, 2H)

Synthesis Example B4 (Step B: $R^2$=Phenyl)

Synthesis of 2,2-diphenyl-5-methanesulfonyloxymethyl-1,3-dioxane (4d)

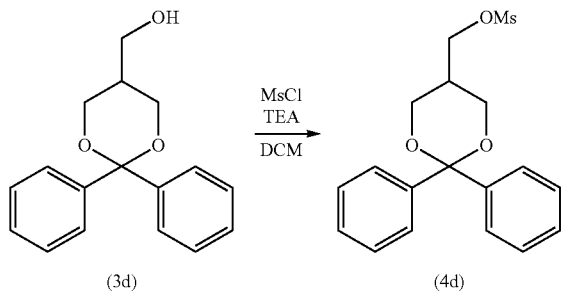

The compound (3d) obtained in Synthesis Example A3 (640 mg) was dissolved in 9.6 mL of $CH_2Cl_2$, and 493 μL of triethylamine was further added thereto, followed by cooling to −20° C. Thereafter, 220 μL of MsCl was added and stirred at −20° C. for 1 hour. Then, 6.4 mL of water was added to the resulting reaction mixture to stop the reaction, extraction was performed twice with 6.4 mL of $CH_2Cl_2$, and the organic layers were washed with 6.4 mL of saturated brine. After the resulting product was dried over magnesium sulfate and filtered, $CH_2Cl_2$ was distilled off under reduced pressure, and the resulting residue was purified with silica gel chromatography (n-hexane:ethyl acetate=3:1) to obtain 729 mg of compound (4d) (yield: 88%).

$^1$H-NMR (500 MHz, $CDCl_3$)

δ: 2.06 (m, 1H), 3.03 (s, 3H), 3.95 (dd, J=12.2, 3.7 Hz, 2H), 4.18 (dd, J=12.2, 3.4 Hz, 2H), 4.51 (d, J=7.5 Hz, 2H), 7.25 (m, 1H), 7.30 (m, 3H), 7.39 (m, 2H), 7.49 (m, 4H)

Step (C)

Synthesis Example C1-1 (Step C: $R^2$=Methyl, Base=TEA, and Solvent=Methyl Ethyl Ketone)

Synthesis of 2,2-dimethyl-5-iodomethyl-1,3-dioxane (5a)

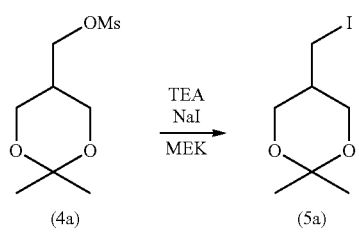

The compound (4a) obtained in Synthesis Example B1 (400.0 mg) was dissolved in 6 mL of methyl ethyl ketone, and 12 μL of triethylamine and 401.1 mg of sodium iodide were added thereto, followed by heating under reflux for 1.5 hours. Thereafter, methyl ethyl ketone in the reaction mixture was distilled off under reduced pressure. Then, 10 mL of $CH_2Cl_2$ and 10 mL of water were added thereto, and the layers were separated. The water layer was extracted twice with 10 mL of $CH_2Cl_2$, and the organic layers were washed by adding 5 mL of 5% sodium thiosulfate and 5 mL of 1% sodium hydrogen carbonate water. The organic layers were further washed with 10 mL of water, and $CH_2Cl_2$ was distilled off under reduced pressure. The resulting residue was purified with silica gel chromatography (n-hexane:ethyl acetate=5:1) to obtain 394.1 g of compound (5a) (yield: 86%).

$^1$H-NMR (500 MHz, $CDCl_3$)

δ: 1.41 (s, 3H), 1.43 (s, 3H), 1.95 (m, 1H), 3.23 (d, J=7 Hz, 2H), 3.73 (dd, J=12, 6.5 Hz, 2H), 4.01 (dd, J=11.5, 4 Hz, 2H)

Synthesis Example C1-2 (Step C: $R^2$=n-Propyl)

Synthesis of 2,2-di-n-propyl-5-iodomethyl-1,3-dioxane (5b)

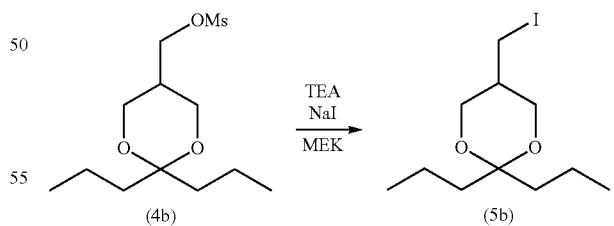

The compound (4b) obtained in Synthesis Example B2 (1.20 g) was dissolved in 14.3 mL of methyl ethyl ketone, and 30 μL of triethylamine and 966 mg of sodium iodide were further added thereto, followed by heating under reflux for 2 hours. Methyl ethyl ketone in the reaction solution was distilled off under reduced pressure, 15 mL of $CH_2Cl_2$ and 15 mL of water were added, and the layers were separated. The water layer was extracted twice with 15 mL of $CH_2Cl_2$, and the organic layers were washed with 7.5 mL of 5% sodium thiosulfate and 7.5 mL of 1% sodium hydrogen carbonate water. The organic layers were further washed with 15 mL of saturated brine. After the resulting product was dried over magnesium sulfate and filtered, CH$_2$Cl$_2$ was distilled off under reduced pressure, and the resulting residue was purified with silica gel chromatography (n-hexane:ethyl acetate=10:1) to obtain 1.16 g of compound (5b) (yield: 86%).

$^1$H-NMR (500 MHz, CDCl$_3$)

δ: 0.93 (t, J=7.3 Hz, 6H), 1.35 (m, 4H), 1.66 (m, 4H), 1.90 (m, 1H), 3.25 (d, J=7.2 Hz, 2H), 3.71 (dd, J=11.8, 6.0 Hz, 2H), 4.01 (dd, J=11.9, 3.9 Hz, 2H)

Synthesis Example C1-3 (Step C: R$^2$=n-Butyl)

Synthesis of 2,2-di-n-butyl-5-iodomethyl-1,3-dioxane (5c)

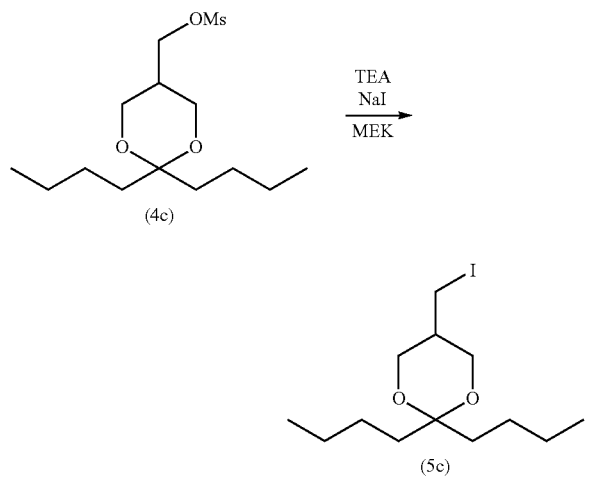

The compound (4c) obtained in Synthesis Example B3 (169 mg) was dissolved in 2.9 mL of methyl ethyl ketone, and 3.8 µL of triethylamine and 123 mg of sodium iodide were further added thereto, followed by heating under reflux for 2 hours. Subsequently, methyl ethyl ketone in the reaction solution was distilled off under reduced pressure, 3 mL of CH$_2$Cl$_2$ and 3 mL of water were added thereto, and the layers were separated. Then, the water layer was extracted twice with 3 mL of CH$_2$Cl$_2$, and the organic layers were washed with 1.5 mL of 5% sodium thiosulfate and 1.5 mL of 1% sodium hydrogen carbonate water. The organic layers were further washed with 3 mL of saturated brine. After the resulting product was dried over magnesium sulfate and filtered, CH$_2$Cl$_2$ was distilled off under reduced pressure. The resulting residue was purified with silica gel chromatography (n-hexane:ethyl acetate=10:1) to obtain 139 mg of compound (5c) (yield: 75%).

$^1$H-NMR (500 MHz, CDCl$_3$)

δ: 0.92 (m, 6H), 1.30 (m, 8H), 1.68 (m, 4H), 1.91 (m, 1H), 3.25 (d, J=7.2 Hz, 2H), 3.71 (dd, J=12.0, 6.2 Hz, 2H), 4.00 (dd, J=11.9, 4.0 Hz, 2H)

Synthesis Example C1-4 (Step C: R$^2$=Phenyl)

Synthesis of 2,2-diphenyl-5-iodomethyl-1,3-dioxane (5d)

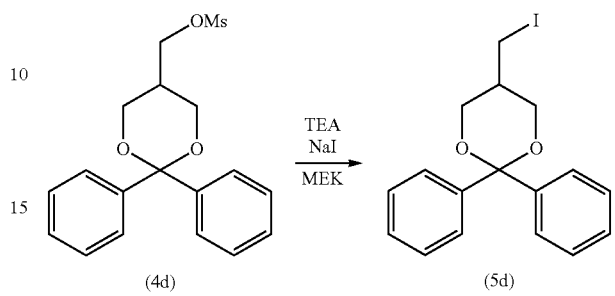

The compound (4d) obtained in Synthesis Example B4 (729 mg) was dissolved in 10.9 mL of methyl ethyl ketone, and 14.5 µL of triethylamine and 470 mg of sodium iodide were further added thereto, followed by heating under reflux for 2 hours. Methyl ethyl ketone in the reaction solution was distilled off under reduced pressure, and 5 mL of CH$_2$Cl$_2$ and 5 mL of water were added thereto, and the layers were separated. The water layer was extracted twice with 3 mL of CH$_2$Cl$_2$, and the organic layers were washed with 2.5 mL of 5% sodium thiosulfate and 2.5 mL of 1% sodium hydrogen carbonate water. The organic layers were further washed with 5 mL of saturated brine. After the resulting product was dried over magnesium sulfate and filtered, CH$_2$Cl$_2$ was distilled off under reduced pressure. The resulting residue was purified with silica gel chromatography (n-hexane:ethyl acetate=10:1) to obtain 726 mg of compound (5d) (yield: 91%).

$^1$H-NMR (500 MHz, CDCl$_3$)

δ: 2.10 (m, 1H), 3.25 (d, J=7.5 Hz, 2H), 3.84 (dd, J=11.7, 6.3 Hz, 2H), 4.16 (dd, J=11.7, 3.8 Hz, 2H), 7.26 (m, 2H), 7.34 (m, 4H), 7.50 (m, 4H)

Synthesis Example C2-1 (Step C: Solvent=Acetone+Methyl Isobutyl Ketone)

Synthesis of 2,2-dimethyl-5-iodomethyl-1,3-dioxane (5a)

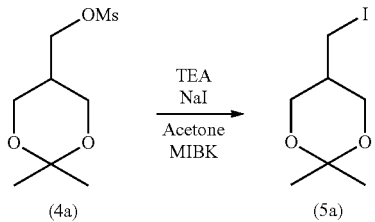

The compound (4a) obtained in Synthesis Example B1 (300 mg) was dissolved in 3 mL of acetone and 3 mL of methyl isobutyl ketone in an argon atmosphere, and 9.3 µL of triethylamine and 301 mg of sodium iodide were further added thereto, followed by heating under reflux for 2 hours. Acetone and methyl isobutyl ketone in the reaction solution were distilled off under reduced pressure, 6 mL of CH$_2$Cl$_2$ and 6 mL of water were added thereto, and the layers were separated. The water layer was extracted twice with 6 mL of CH$_2$Cl$_2$, the organic layers were washed with 3 mL of 5% sodium thiosulfate and 3 mL of 1% sodium hydrogen carbonate water. After the organic layers were further washed with 6 mL of saturated brine and dried over magnesium sulfate, CH$_2$Cl$_2$ was distilled off under reduced pressure. The resulting residue was purified with silica gel chromatography (n-hexane:ethyl acetate=10:1) to obtain 266 mg of compound (5a) (yield: 78%).

Synthesis Example C2-2 (Step C: Solvent=Acetone)

Synthesis of 2,2-dimethyl-5-iodomethyl-1,3-dioxane (5a)

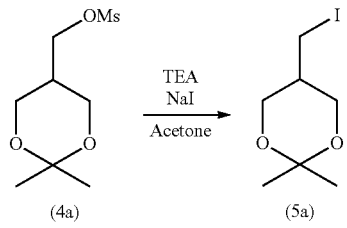

The compound (4a) obtained in Synthesis Example B1 (300 mg) was dissolved in 6 mL of acetone in an argon atmosphere. Then, 9.3 μL of triethylamine and 301 mg of sodium iodide were further added thereto, and the mixture was heated under reflux for 2 hours. Acetone in the reaction solution was distilled off under reduced pressure, 6 mL of CH$_2$Cl$_2$ and 6 mL of water were added thereto, and the layers were separated. The water layer was extracted twice with 6 mL of CH$_2$Cl$_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, CH$_2$Cl$_2$ was distilled off under reduced pressure. The resulting residue was purified with silica gel chromatography (n-hexane:ethyl acetate=10:1) to obtain 204 mg of compound (5a) (yield: 59%).

Synthesis Example C2-3 (Step C: Solvent=Methyl Isobutyl Ketone)

Synthesis of 2,2-dimethyl-5-iodomethyl-1,3-dioxane (5a)

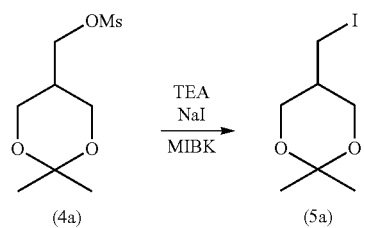

The compound (4a) obtained in Synthesis Example B1 (300 mg) was dissolved in 6 mL of methyl isobutyl ketone in an argon atmosphere, and 9.3 μL of triethylamine and 301 mg of sodium iodide were added thereto, followed by heating under reflux for 2 hours. Methyl isobutyl ketone in the reaction solution was distilled off under reduced pressure, 6 mL of CH$_2$Cl$_2$ and 6 mL of water were added thereto, and the layers were separated. The water layer was extracted twice with 6 mL of CH$_2$Cl$_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, CH$_2$Cl$_2$ was distilled off under reduced pressure. The resulting residue was purified with silica gel chromatography (n-hexane:ethyl acetate=10:1) to obtain 190 mg of compound (5a) (yield: 55%).

Synthesis Example C3-1 (Step C: Alkali Metal Halide=Sodium Bromide)

Synthesis of 2,2-dimethyl-5-bromomethyl-1,3-dioxane (5a-1)

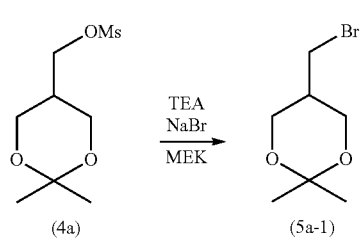

The compound (4a) obtained in Synthesis Example B1 (300 mg) was dissolved in 6 mL of methyl ethyl ketone in an argon atmosphere, and 9.3 μL of triethylamine and 207 mg of sodium bromide were further added thereto, followed by heating under reflux for 23 hours. Methyl ethyl ketone in the reaction solution was distilled off under reduced pressure, 6 mL of CH$_2$Cl$_2$ and 6 mL of water were added thereto, and the layers were separated. The water layer was extracted twice with 6 mL of CH$_2$Cl$_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, CH$_2$Cl$_2$ was distilled off under reduced pressure. The resulting residue was purified with silica gel chromatography (n-hexane:ethyl acetate=10:1) to obtain 127 mg of compound (5a-1) (yield: 45%).

$^1$H-NMR (500 MHz, CDCl$_3$)

δ: 1.41 (s, 3H), 1.44 (s, 3H), 2.02 (m, 1H), 3.51 (d, J=7.1 Hz, 2H), 3.80 (dd, J=12, 5.7 Hz, 2H), 4.05 (dd, J=12, 4 Hz, 2H)

Synthesis Example C4-1 (Step C: Base=Diisopropylethyleneamine)

Synthesis of 2,2-dimethyl-5-iodomethyl-1,3-dioxane (5a)

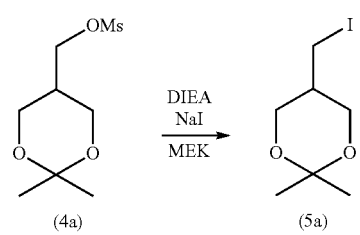

The compound (4a) obtained in Synthesis Example B1 (300 mg) was dissolved in 6 mL of methyl ethyl ketone in an argon atmosphere, and 12 μL of diisopropylethyleneamine and 301 mg of sodium iodide were further added thereto, followed by heating under reflux for 2 hours. Methyl ethyl ketone in the reaction solution was distilled off under reduced pressure, 6 mL of $CH_2Cl_2$ and 6 mL of water were added thereto, and the layers were separated. The water layer was extracted twice with 6 mL of $CH_2Cl_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, $CH_2Cl_2$ was distilled off under reduced pressure. The resulting residue was purified with silica gel chromatography (n-hexane:ethyl acetate=10:1) to obtain 262 mg of compound (5a) (yield: 78%).

Synthesis Example C4-2 (Step C: Base=Sodium Hydrogen Carbonate, Solvent=Methyl Ethyl Ketone)

Synthesis of 2,2-dimethyl-5-iodomethyl-1,3-dioxane (5a)

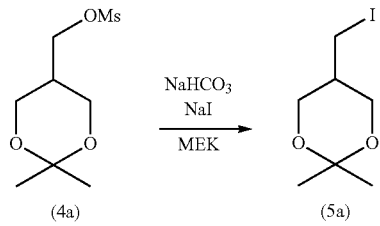

The compound (4a) obtained in Synthesis Example B1 (300 mg) was dissolved in 6 mL of methyl ethyl ketone in an argon atmosphere, and 5.6 mg of sodium hydrogen carbonate and 301 mg of sodium iodide were further added thereto, followed by heating under reflux for 2 hours. Methyl ethyl ketone in the reaction solution was distilled off under reduced pressure, 6 mL of $CH_2Cl_2$ and 6 mL of water were added thereto, and the layers were separated. The water layer was extracted twice with 6 mL of $CH_2Cl_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, $CH_2Cl_2$ was distilled off under reduced pressure. The resulting residue was purified with silica gel chromatography (n-hexane:ethyl acetate=10:1) to obtain 234 mg of compound (5a) (yield: 68%).

Synthesis Example C4-3 (Step C: Base=$NaHCO_3$, Solvent=Acetone)

Synthesis of 2,2-dimethyl-5-iodomethyl-1,3-dioxane (5a)

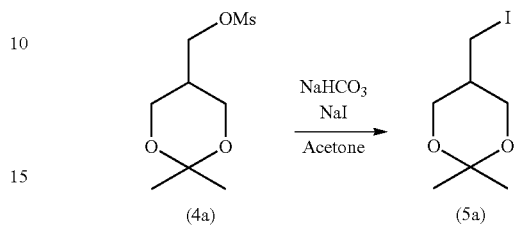

The compound (4a) obtained in Synthesis Example B1 (15.0 g) was dissolved in 225 mL of acetone, and 5.62 g of sodium hydrogen carbonate and 20.05 g of sodium iodide were added thereto, followed by heating under reflux for 19 hours. After a white solid was filtered and washed with acetone, acetone was distilled off under reduced pressure, and 150 mL of $CH_2Cl_2$ was added thereto. The organic layer was washed by adding 50 mL of 5% sodium thiosulfate and 50 mL of 1% sodium hydrogen carbonate water, and the layers were separated. Extraction was performed with 50 mL of $CH_2Cl_2$, the organic layer was washed with 5% brine, and $CH_2Cl$ was distilled off under reduced pressure. The resulting residue was purified with silica gel chromatography (n-hexane:ethyl acetate=5:1) to obtain 14.00 g of compound (5a) (yield: 82%).

Synthesis Example C4-4 (Step C: Base=Potassium Hydrogen Carbonate)

Synthesis of 2,2-dimethyl-5-iodomethyl-1,3-dioxane (5a)

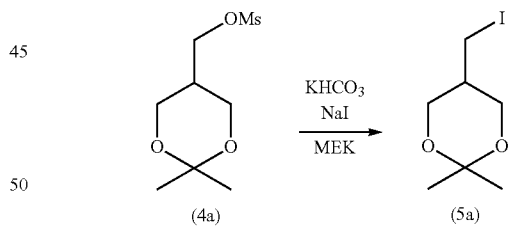

The compound (4a) obtained in Synthesis Example B1 (300 mg) was dissolved in 6 mL of methyl ethyl ketone in an argon atmosphere, and 6.7 mg of potassium hydrogen carbonate and 301 mg of sodium iodide were further added thereto, followed by heating under reflux for 2 hours. Methyl ethyl ketone in the reaction solution was distilled off under reduced pressure, 6 mL of $CH_2Cl_2$ and 6 mL of water were added thereto, and the layers were separated. The water layer was extracted twice with 6 mL of $CH_2Cl_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, $CH_2Cl_2$ was distilled off under reduced pressure. The resulting residue was purified with silica gel chromatography (n-hexane:ethyl acetate=10:1) to obtain 106 mg of compound (5a) (yield: 31%).

Synthesis Example C4-5 (Step C: Base=Potassium Carbonate)

Synthesis of 2,2-dimethyl-5-iodomethyl-1,3-dioxane (5a)

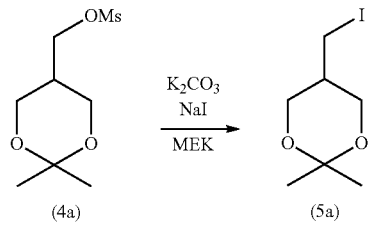

The compound (4a) obtained in Synthesis Example B1 (300 mg) was dissolved in 6 mL of methyl ethyl ketone in an argon atmosphere, and potassium carbonate and 301 mg of sodium iodide were further added thereto, followed by heating under reflux for 2 hours. Methyl ethyl ketone in the reaction solution was distilled off under reduced pressure, 6 mL of $CH_2Cl_2$ and 6 mL of water were added thereto, and the layers were separated. The water layer was extracted twice with 6 mL of $CH_2Cl_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, $CH_2Cl_2$ was distilled off under reduced pressure. The resulting residue was purified with silica gel chromatography (n-hexane:ethyl acetate=10:1) to obtain 209 mg of compound (5a) (yield: 61%).

Synthesis Example C4-6 (Step C: Base=Sodium Carbonate)

Synthesis of 2,2-dimethyl-5-iodomethyl-1,3-dioxane (5a)

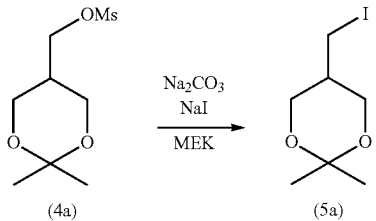

The compound (4a) obtained in Synthesis Example B1 (300 mg) was dissolved in 6 mL of methyl ethyl ketone in an argon atmosphere, and sodium carbonate and 301 mg of sodium iodide were further added thereto, followed by heating under reflux for 2 hours. Methyl ethyl ketone in the reaction solution was distilled off under reduced pressure, 6 mL of $CH_2Cl_2$ and 6 mL of water were added thereto, and the layers were separated. The water layer was extracted twice with 6 mL of $CH_2Cl_2$, and the organic layers were washed with 3 mL of 5% sodium thiosulfate and 3 mL of 1% sodium hydrogen carbonate water. After the organic layers were further washed with 6 mL of saturated brine and dried over magnesium sulfate, $CH_2Cl_2$ was distilled off under reduced pressure. The resulting residue was purified with silica gel chromatography (n-hexane:ethyl acetate=10:1) to obtain 270 mg of compound (5a) (yield: 79%).

Step (B')

Synthesis Example B1 (Step B': Solvent=Dichloromethane)

Synthesis of 2,2-dimethyl-5-iodomethyl-1,3-dioxane (5a)

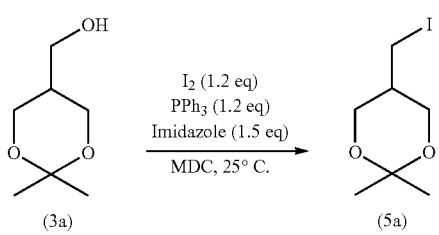

2,2-Dimethyl-5-(hydroxymethyl)-1,3-dioxane (3a) (1.00 g) was dissolved in 22.8 mL of dichloromethane (MDC), and 700.0 mg of imidazole and 2.08 g of iodine were added thereto, followed by cooling to 0° C. Subsequently, 2.15 g of triphenylphosphine was added, and the mixture was stirred at 25° C. for 2 hours. The reaction was then quenched with 20 mL of water, and the resulting product was extracted twice with 10 mL of dichloromethane and washed with 20 mL of water. Dichloromethane was distilled off from the organic phases under reduced pressure, and the resulting residue was purified with silica gel chromatography (n-hexane:ethyl acetate=5:1) to obtain 1.38 g of 2,2-dimethyl-5-iodomethyl-1,3-dioxane (5a) (yield: 79%).

Synthesis Example B2 (Step B': Solvent=THF)

Synthesis of 2,2-dimethyl-5-iodomethyl-1,3-dioxane (5a)

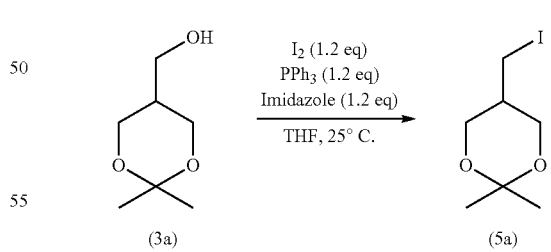

2,2-Dimethyl-5-(hydroxymethyl)-1,3-dioxane (3a) (500.0 mg) was dissolved in 3.4 mL of tetrahydrofuran, and cooled to 0° C. Thereafter, 1.08 g of triphenylphosphine, 279.5 mg of imidazole, and 1.04 g of iodine were added thereto, and the mixture was stirred at 25° C. for 2.5 hours. The resulting product was then washed with 10 mL of 5% aqueous sodium thiosulfate solution, extracted with 20 mL of ethyl acetate, and washed with 5% brine. After the organic phase was dried over magnesium sulfate and filtered, ethyl acetate was distilled off under reduced pressure. The resulting residue was purified with silica gel chromatography (n-hexane:ethyl acetate=5:1) to obtain 639.0 mg of 2,2-dimethyl-5-iodomethyl-1,3-dioxane (5a) (yield: 73%).

Synthesis Example B3 (Step B': Solvent=CPME)

Synthesis of 2,2-dimethyl-5-bromomethyl-1,3-dioxane (5a)

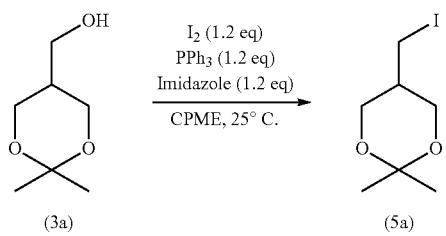

2,2-Dimethyl-5-(hydroxymethyl)-1,3-dioxane (3a) (500.0 mg) was dissolved in 6.8 mL of tetrahydrofuran, followed by cooling to 0° C. Thereafter, 1.08 g of triphenylphosphine, 279.5 mg of imidazole, and 1.04 g of iodine were added thereto, and the mixture was stirred at 25° C. for 2 hours. After triphenylphosphine oxide was removed, and the resulting product was washed with 10 mL of CPME, the organic phase was washed with 10 mL of 5% aqueous sodium thiosulfate solution, extracted 3 times with 10 mL of CPME, and washed with 5% brine. CPME was distilled off under reduced pressure, and the resulting residue was purified with silica gel chromatography (n-hexane:ethyl acetate=5:1) to obtain 621.1 mg of 2,2-dimethyl-5-bromomethyl-1,3-dioxane (5a) (yield: 71%).

Synthesis Example B4 (Step B': Solvent=Dichloromethane)

Synthesis of 2,2-dimethyl-5-bromomethyl-1,3-dioxane (5b)

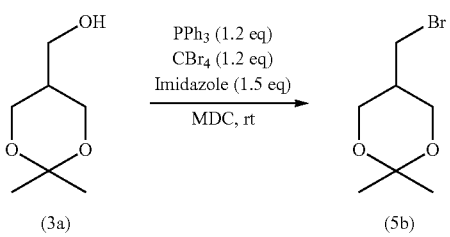

2,2-Dimethyl-5-(hydroxymethyl)-1,3-dioxane (3a) (1.00 g) was dissolved in 22.8 mL of dichloromethane (MDC), and 700.0 mg of imidazole and 2.72 g of carbon tetrabromide were added thereto. After ice-cooling, 2.15 g of triphenylphosphine was further added, and the mixture was stirred at room temperature for 4 hours. Dichloromethane was distilled off under reduced pressure, and the resulting product was purified with silica gel chromatography (n-hexane:ethyl acetate=5:1) to quantitatively obtain 1.60 g of 2,2-dimethyl-5-bromomethyl-1,3-dioxane (5b).

Step (D)

Synthesis Example D1-1 (Step D: $R^2$=Methyl)

Synthesis of (2,2-dimethyl-[1,3]dioxan-5-yl methyl)-phosphonic Acid Dimethyl Ester (6a)

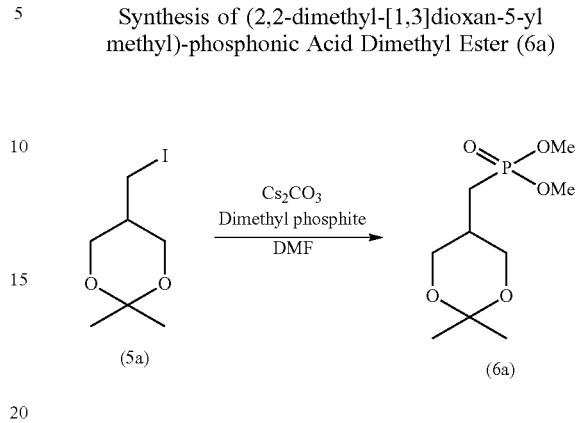

The iodine compound (5a) obtained in Synthesis Example C1-1 (300.0 mg) was dissolved in 2.34 mL of DMF. Then, 763.4 mg of cesium carbonate and 215 μL of dimethyl phosphite were further added thereto, followed by stirring at 40° C. for 5 hours. DMF in the reaction solution was distilled off under reduced pressure, and 5 mL of toluene was added to the obtained residue. A white solid was then filtered. After the white solid was further washed with 5 mL of toluene, the obtained filtrate was concentrated under reduced pressure, and the residue was purified with silica gel chromatography (chloroform:methanol=10:1) to obtain 255.6 mg of phosphonic acid dimethyl compound (6a) (yield: 92%).

$^1$H-NMR (500 MHz, CDCl$_3$)
δ: 1.42 (s, 6H), 1.82 (dd, J=18.5, 6.5 Hz, 2H), 2.15 (m, 1H), 3.66 (dd, J=11.5, 7 Hz, 2H), 3.75 (d, J=10.5 Hz, 6H), 4.01 (d, J=12, 3.5 Hz, 2H)

Synthesis Example D1-2 (Step D: $R^2$=n-Propyl)

Synthesis of (2,2-di-n-propyl-[1,3]dioxan-5-yl methyl)-phosphonic Acid Dimethyl Ester (6b)

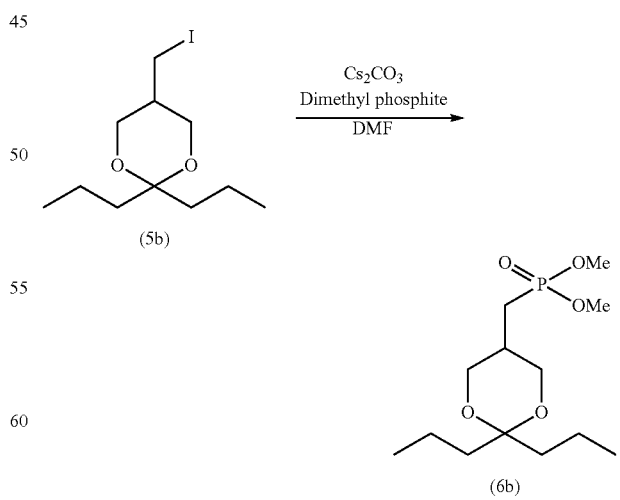

The iodine compound (5b) obtained in Synthesis Example C1-2 (1.06 g) was dissolved in 6.8 mL of DMF. Then, 2.21 g of cesium carbonate and 621 μL of dimethyl phosphite were further added thereto, followed by stirring at 40° C. for 3 hours. DMF in the reaction solution was distilled off under reduced pressure, and 5 mL of toluene was added to the obtained residue. A white solid was then filtered. After the white solid was further washed with 2.5 mL of toluene, the resulting filtrate was concentrated under reduced pressure, and the residue was purified with silica gel chromatography (chloroform:methanol=20:1) to obtain 767 mg of phosphonic acid dimethyl compound (6b) (yield: 79%).

$^1$H-NMR (500 MHz, CDCl$_3$)

δ: 0.91 (t, J=7.4 Hz, 6H), 1.36 (m, 4H), 1.66 (m, 4H), 1.84 (dd, J=18.7, 6.9 Hz, 2H), 2.09 (m, 1H), 3.63 (dd, J=11.7, 6.6 Hz, 2H), 3.75 (d, J=10.9 Hz, 6H), 3.99 (dd, J=11.7, 3.8 Hz, 2H)

Synthesis Example D1-3 (Step D: R$^2$=Butyl)

Synthesis of (2,2-dibutyl-[1,3]dioxan-5-yl methyl)-phosphonic Acid Dimethyl Ester (6c)

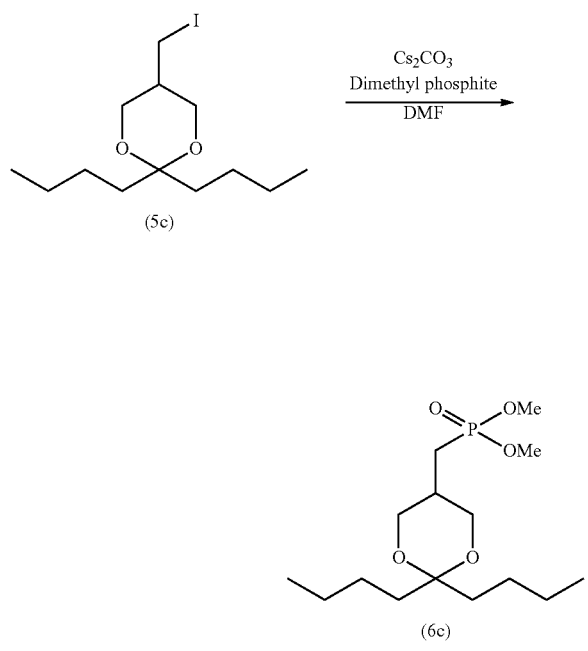

The iodine compound (5c) obtained in Synthesis Example C1-3 (139 mg) was dissolved in 1.2 mL of DMF. Then, 266 mg of cesium carbonate and 75 μL of dimethyl phosphite were further added thereto, followed by stirring at 50° C. for 3 hours. DMF in the reaction solution was distilled off under reduced pressure, and 1 mL of toluene was added to the obtained residue. A white solid was then filtered. After the white solid was further washed with 1 mL of toluene, the resulting filtrate was concentrated under reduced pressure, and the residue was purified with silica gel chromatography (chloroform:methanol=10:1) to obtain 80.5 mg of phosphonic acid dimethyl compound (6c) (yield: 61%).

$^1$H-NMR (500 MHz, CDCl$_3$)

δ: 0.91 (m, 6H), 1.30 (m, 8H), 1.68 (m, 4H), 1.83 (dd, J=18.7, 6.9 Hz, 2H), 2.10 (m, 1H), 3.63 (dd. J=11.8, 6.7 Hz, 2H), 3.75 (d, J=10.9 Hz, 6H), 3.99 (dd, J=11.7, 3.9 Hz, 2H)

Synthesis Example D1-4 (Step D: R$^2$=Phenyl)

Synthesis of (2,2-diphenyl-[1,3]dioxan-5-yl methyl)-phosphonic Acid Dimethyl Ester (6d)

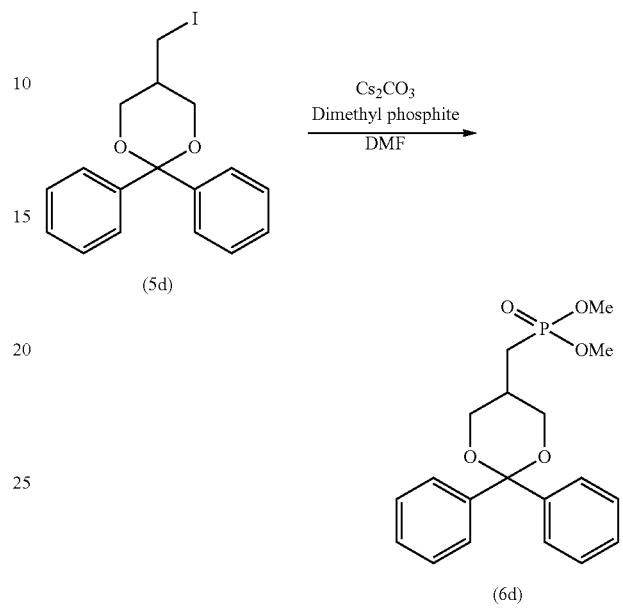

The iodine compound (5d) obtained in Synthesis Example C1-4 (726 mg) was dissolved in 5.7 mL of DMF. Then, 1.24 g of cesium carbonate and 350 μL of dimethyl phosphite were further added, followed by stirring at 50° C. for 3 hours. DMF in the reaction solution was distilled off under reduced pressure, and 4.2 mL of toluene was added to the obtained residue. A white solid was then filtered. After the white solid was further washed with 2.1 mL of toluene, the resulting filtrate was concentrated under reduced pressure, and the residue was purified with silica gel chromatography (chloroform:methanol=10:1) to obtain 621 mg of phosphonic acid dimethyl compound (6d) (yield: 90%).

$^1$H-NMR (500 MHz, CDCl$_3$)

δ: 1.80 (dd, J=18.8, 7.0 Hz, 2H), 2.30 (m, 1H), 3.74 (d, J=10.9 Hz, 6H), 3.77 (dd, J=11.5, 7.2 Hz, 2H), 4.15 (dd, J=11.5, 3.8 Hz, 2H), 7.26 (m, 2H), 7.33 (m, 4H), 7.50 (m, 4H)

Synthesis Example D2-1 (Step D: R$^2$=Methyl, Solvent=DMF)

Synthesis of (2,2-dimethyl-[1,3]dioxan-5-yl methyl)-phosphonic Acid Dimethyl Ester (6a)

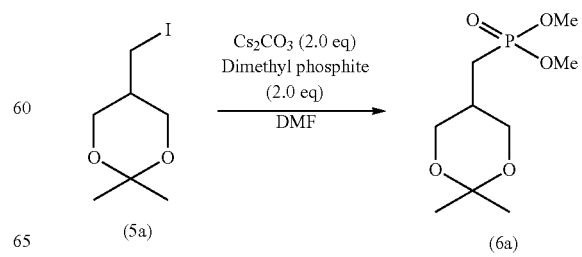

The iodine compound (5a) obtained in Synthesis Example C1-1 (500.0 mg) was dissolved in 3.9 mL of DMF. Then, 1.27 g of cesium carbonate and 360 µL of dimethyl phosphite were further added, followed by stirring at 50° C. for 3 hours. DMF in the reaction solution was distilled off under reduced pressure, and 10 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 406.0 mg of phosphonic acid dimethyl compound (6a) (yield: 87%).

Synthesis Example D2-2 (Step D: R$^2$=Methyl, Solvent=DMAc)

Synthesis of (2,2-dimethyl-[1,3]dioxan-5-yl methyl)-phosphonic Acid Dimethyl Ester (6a)

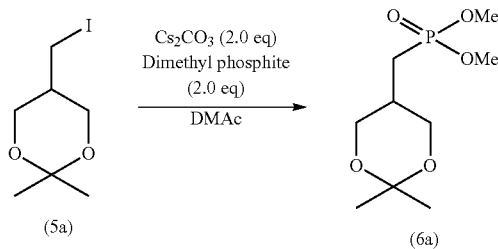

The iodine compound (5a) obtained in Synthesis Example C1-1 (500.0 mg) was dissolved in 3.9 mL of DMAc. Then, 1.27 g of cesium carbonate and 360 µL of dimethyl phosphite were further added, followed by stirring at 50° C. for 3 hours. DMAc in the reaction solution was distilled off under reduced pressure, and 10 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 438.7 mg of phosphonic acid dimethyl compound (6a) (yield: 94%).

Synthesis Example D2-3 (Step D: R$^2$=Methyl, Solvent=Acetonitrile)

Synthesis of (2,2-dimethyl-[1,3]dioxan-5-yl methyl)-phosphonic Acid Dimethyl Ester (6a)

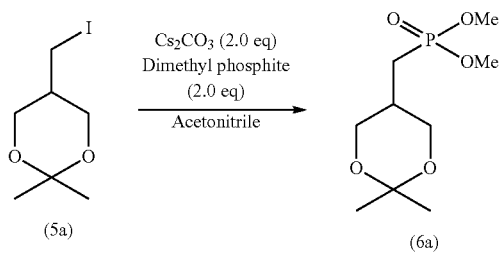

The iodine compound (5a) obtained in Synthesis Example C1-1 (500.0 mg) was dissolved in 3.9 mL of acetonitrile. Then, 1.27 g of cesium carbonate and 360 µL of dimethyl phosphite were further added, followed by stirring at 50° C. for 24 hours. Acetonitrile in the reaction solution was distilled off under reduced pressure, and 20 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 408.8 mg of phosphonic acid dimethyl compound (6a) (yield: 88%).

Synthesis Example D2-4 (Step D: R$^2$=Methyl, Solvent=DMF/AN (1/1))

Synthesis of (2,2-dimethyl-[1,3]dioxan-5-yl methyl)-phosphonic Acid Dimethyl Ester (6a)

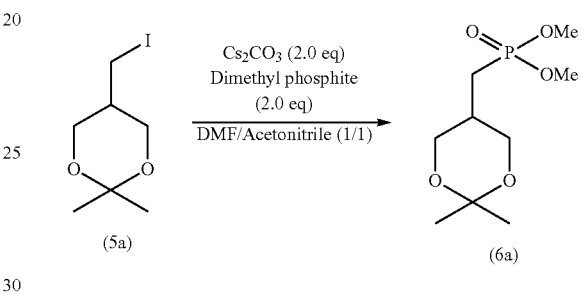

The iodine compound (5a) obtained in Synthesis Example C1-1 (500.0 mg) was dissolved in 2.0 mL of DMF and 2.0 mL of acetonitrile. Then, 1.27 g of cesium carbonate and 360 µL of dimethyl phosphite were further added, followed by stirring at 50° C. for 18 hours. The solvent in the reaction solution was distilled off under reduced pressure, and 20 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 404.1 mg of phosphonic acid dimethyl compound (6a) (yield: 87%).

Synthesis Example D3-1 (Step D: R$^2$=Methyl, Base=Cesium Carbonate)

Synthesis of (2,2-dimethyl-[1,3]dioxan-5-yl methyl)-phosphonic Acid Dimethyl Ester (6a)

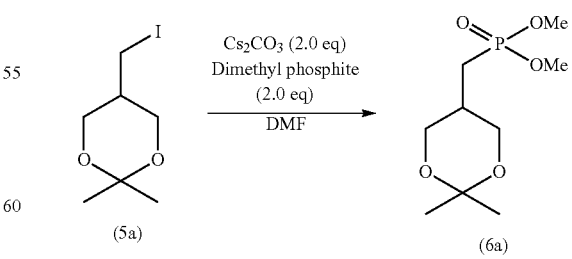

The iodine compound (5a) obtained in Synthesis Example C1-1 (500.0 mg) was dissolved in 3.9 mL of DMF. Then, 1.27 g of cesium carbonate and 360 µL of dimethyl phosphite were further added, followed by stirring at 50° C. for 3 hours. DMF in the reaction solution was distilled off under reduced pressure, and 10 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 406.0 mg of phosphonic acid dimethyl compound (6a) (yield: 87%).

Synthesis Example D3-2 (Step D: $R^2$=Methyl, Base=Potassium Carbonate)

Synthesis of (2,2-dimethyl-[1,3]dioxan-5-yl methyl)-phosphonic Acid Dimethyl Ester (6a)

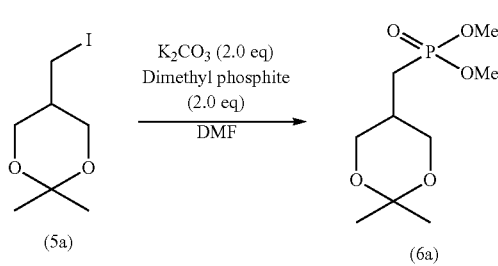

The iodine compound (5a) obtained in Synthesis Example C1-1 (500.0 mg) was dissolved in 3.9 mL of DMF. Then, 540 mg of potassium carbonate and 360 µL of dimethyl phosphite were further added, followed by stirring at 50° C. for 24 hours. DMF in the reaction solution was distilled off under reduced pressure, and 10 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 139.6 mg of phosphonic acid dimethyl compound (6a) (yield: 30%).

Synthesis Example D3-3 (Step D: $R^2$=Methyl, Base=Rubidium Carbonate)

Synthesis of (2,2-dimethyl-[1,3]dioxan-5-yl methyl)-phosphonic Acid Dimethyl Ester (6a)

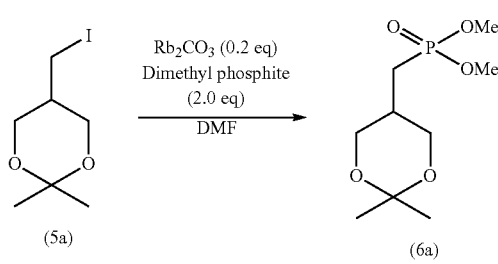

The iodine compound (5a) obtained in Synthesis Example C1-1 (500.0 mg) was dissolved in 3.9 mL of DMF. Then, 902.1 mg of rubidium carbonate and 360 µL of dimethyl phosphite were further added, followed by stirring at 50° C. for 24 hours. DMF in the reaction solution was distilled off under reduced pressure, and 10 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 280.7 mg of phosphonic acid dimethyl compound (6a) (yield: 60%).

Synthesis Example D3-4 (Step D: $R^2$=Methyl, Base=Sodium Carbonate)

Synthesis of (2,2-dimethyl-[1,3]dioxan-5-yl methyl)-phosphonic Acid Dimethyl Ester (6a)

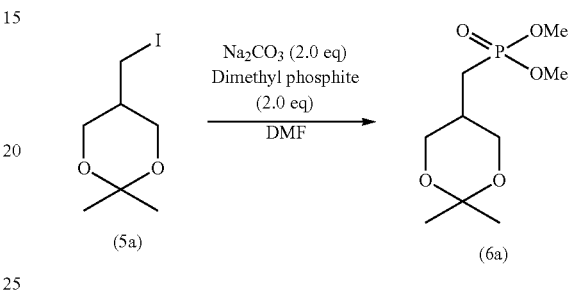

The iodine compound (5a) obtained in Synthesis Example C1-1 (500.0 mg) was dissolved in 3.9 mL of DMF. Then, 414.0 mg of sodium carbonate and 360 µL of dimethyl phosphite were further added, followed by stirring at 50° C. for 24 hours. DMF in the reaction solution was distilled off under reduced pressure, and 10 mL of toluene was added to the obtained residue. A white solid was then filtered. After the white solid was further washed with 10 mL of toluene, the resulting filtrate was concentrated under reduced pressure, the residue was diluted with toluene to a total volume of 5 mL, and the yield was quantitatively determined in the liquid. The yield was 1.2%.

Synthesis Example D3-5 (Step D: $R^2$=Methyl, Base=Potassium Hydrogen Carbonate)

Synthesis of (2,2-dimethyl-[1,3]dioxan-5-yl methyl)-phosphonic Acid Dimethyl Ester (6a)

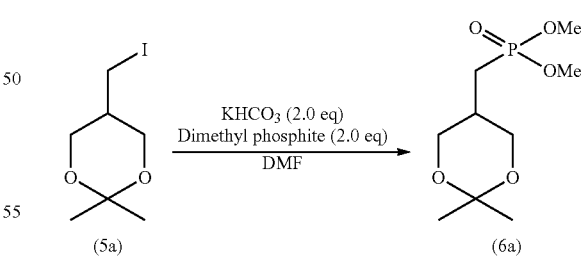

The iodine compound (5a) obtained in Synthesis Example C1-1 (500.0 mg) was dissolved in 3.9 mL of DMF. Then, 391.1 mg of potassium hydrogen carbonate and 360 µL of dimethyl phosphite were further added, followed by stirring at 50° C. for 24 hours. DMF in the reaction solution was distilled off under reduced pressure, and 10 mL of toluene was added to the obtained residue. A white solid was then filtered. After the white solid was further washed with 10 mL of toluene, the resulting filtrate was concentrated under reduced pressure, the residue was toluene to a total volume of 5 mL, and the yield was quantitatively determined in the liquid. The yield was 3.5%.

Synthesis Example D4-1 (Step D: X=Bromine)

Synthesis of (2,2-dimethyl-[1,3]dioxan-5-yl methyl)-phosphonic Acid Dimethyl Ester (6a)

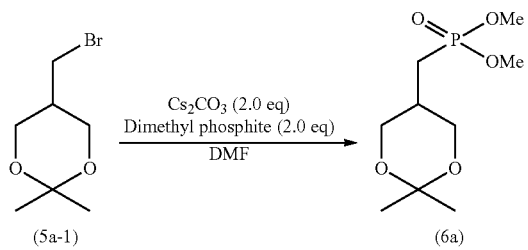

The bromine compound (5a-1) obtained in Synthesis Example C3-1 (93.7 mg) was dissolved in 0.9 mL of DMF. Then, 292 mg of cesium carbonate and 82.1 μL of dimethyl phosphite were further added, followed by stirring at 50° C. for 4 hours. DMF in the reaction solution was distilled off under reduced pressure, and 5 mL of toluene was added to the obtained residue. A white solid was then filtered. After the white solid was further washed with 10 mL of toluene, the resulting filtrate was concentrated under reduced pressure, and the residue was purified with silica gel chromatography (chloroform:methanol=10:1) to obtain 89.3 mg of phosphonic acid dimethyl compound (6a) (yield: 84%).

Synthesis Example D5-1 (Step D: $R^1$=Ethyl)

Synthesis of (2,2-dimethyl-[1,3]dioxan-5-yl methyl)-phosphonic Acid Diethyl Ester (6a-1)

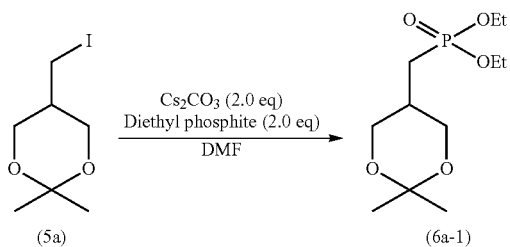

The iodine compound (5a) obtained in Synthesis Example C1-1 (2.00 g) was dissolved in 15.6 mL of DMF. Then, 5.09 g of cesium carbonate and 2.01 mL of diethyl phosphite were further added, followed by stirring at 50° C. for 3 hours. DMF in the reaction solution was distilled off under reduced pressure, and 20 mL of toluene was added to the obtained residue. A white solid was then filtered. After the white solid was further washed with 30 mL of toluene, the resulting filtrate was concentrated under reduced pressure, and the residue was purified with silica gel chromatography (chloroform:methanol=10:1) to quantitatively obtain 2.24 g of phosphonic acid diethyl compound (6a-1).

$^1$H-NMR (500 MHz, CDCl$_3$)

δ: 1.33 (t, J=7 Hz, 6H), 1.42 (s, 3H), 1.42 (s, 3H), 1.76 (dd, J=19, 7 Hz, 2H), 2.18 (m, 1H), 3.66 (dd, J=11.5, 7.5 Hz, 2H), 4.00 (dd, J=11.5, 4 Hz, 2H), 4.10 (m, 4H)

Synthesis Example D5-2 (Step D: $R^1$=n-Butyl)

Synthesis of (2,2-dimethyl-[1,3]dioxan-5-yl methyl)-phosphonic Acid Diethyl Ester (6a-2)

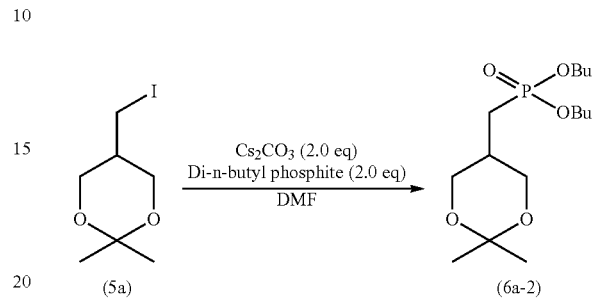

The iodine compound (5a) obtained in Synthesis Example C1-1 (2.00 g) was dissolved in 15.6 mL of DMF. Then, 5.09 g of cesium carbonate and 3.05 mL of dibutyl phosphite were further added, followed by stirring at 50° C. for 3 hours. DMF in the reaction solution was distilled off under reduced pressure, and 20 mL of toluene was added to the obtained residue. A white solid was then filtered. After the white solid was further washed with 20 mL of toluene, the resulting filtrate was concentrated under reduced pressure, and the residue was purified with silica gel chromatography (chloroform:methanol=10:1) to quantitatively obtain 2.74 g of phosphonic acid dibutyl compound (6a-2).

$^1$H-NMR (500 MHz, CDCl$_3$)

δ: 0.94 (t, J=7.5 Hz, 6H), 1.40 (tq, J=7.5, 7.5 Hz, 4H), 1.42 (s, 6H), 1.65 (tt, J=8, 8 Hz, 4H), 1.75 (dd, J=19, 7 Hz, 2H), 2.17 (m, 1H), 3.66 (dd, J=11.5, 7.5 Hz, 2H), 4.03 (m, 6H)

Synthesis Example D5-3 (Step D: $R^2$=Ethyl)

Synthesis of (2,2-dimethyl-[1,3]dioxan-5-yl methyl)-phosphonic Acid Diethyl Ester (6a-3)

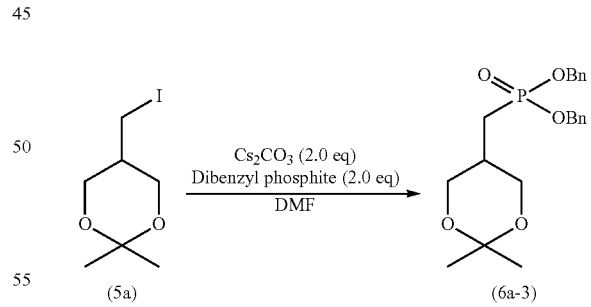

The iodine compound (5a) obtained in Synthesis Example C1-1 (1.00 g) was dissolved in 7.8 mL of DMF. Then, 2.54 g of cesium carbonate and 1.74 mL of dibenzyl phosphite were further added, followed by stirring at 50° C. for 3 hours. DMF in the reaction solution was distilled off under reduced pressure, and 10 mL of toluene was added to the obtained residue. A white solid was then filtered. After the white solid was further washed with 20 mL of toluene, the resulting filtrate was concentrated under reduced pressure, and the resulting residue was purified with silica gel chromatography (n-hexane:ethyl acetate=1:2) to quantitatively obtain 1.58 g of phosphonic acid dibenzyl compound (6a-3).

¹H-NMR (500 MHz, CDCl₃)

δ: 1.38 (s, 3H), 1.39 (s, 3H), 1.77 (dd, J=19, 7 Hz, 2H), 2.11 (m, 1H), 3.58 (dd, J=11.5, 7 Hz, 2H), 3.93 (dd, 12, 4 Hz, 2H), 5.00 (m, 4H), 7.34 (m, 10H)

Step (E)

Synthesis Example E1-1 (Step E: $R^2$=Methyl)

Synthesis of (2,3-dihydroxypropyl)-phosphonic Acid Dimethyl Ester (7a)

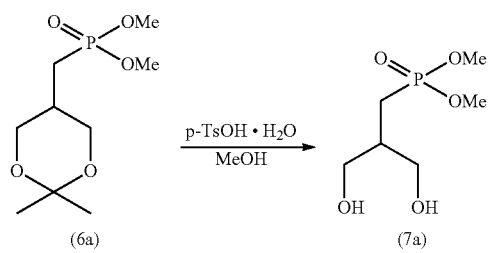

The phosphonic acid dimethyl compound (6a) obtained in Synthesis Example D1-1 (5.00 g) was dissolved in 125 mL of methanol, and 798.5 mg of p-toluenesulfonic acid monohydrate was further added thereto, followed by stirring at 20° C. for 3 hours. The reaction was stopped with 640 μL of triethylamine, and methanol in the reaction solution was distilled off under reduced pressure. The resulting residue was purified with silica gel chromatography (chloroform:methanol=10:1) to obtain 3.82 g of diol compound (7a) (yield: 92%).

¹H-NMR (500 MHz, CDCl₃)

δ: 1.93 (dd, J=18.5, 7 Hz, 2H), 2.13 (m, 1H), 2.87 (dd, J=6, 6 Hz, 2H), 3.77 (m, 10H)

Synthesis Example E1-2 (Step E: $R^2$=n-Propyl)

Synthesis of 2-(dimethylphosphono)methyl-1,3-propanediol (7a)

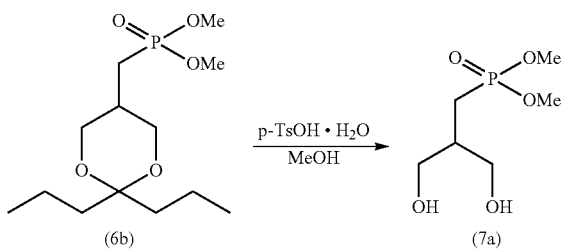 [SMILES: "MeOH" ; CCCC1(CCC)OCC(CP(=O)(OC)OC)CO1 ; COP(=O)(CC(CO)CO)OC]

The phosphonic acid dimethyl compound (6b) obtained in Synthesis Example D1-2 (687 mg) was dissolved in 4.7 mL of methanol, and 22.0 mg of p-toluenesulfonic acid monohydrate was further added thereto, followed by stirring at 20° C. for 3 hours. Then, methanol in the reaction solution was distilled off under reduced pressure. The resulting residue was purified with silica gel chromatography (chloroform:methanol=5:1) to obtain 361 mg of diol compound (7a) (yield: 78%).

Synthesis Example E1-3 (Step E: $R^2$=Butyl)

Synthesis of 2-(dimethylphosphono)methyl-1,3-propanediol (7a)

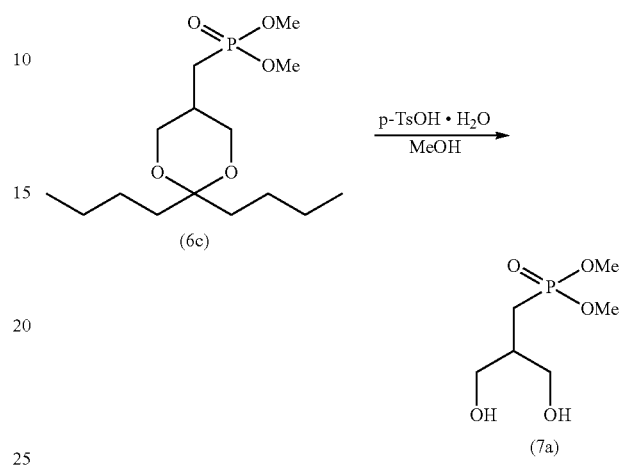

The phosphonic acid dimethyl compound (6c) obtained in Synthesis Example D1-3 (80.5 mg) was dissolved in 0.75 mL of methanol, and 2.4 mg of p-toluenesulfonic acid monohydrate was further added thereto, followed by stirring at 20° C. for 3 hours. Then, methanol in the reaction solution was distilled off under reduced pressure. The resulting residue was purified with silica gel chromatography (chloroform:methanol=10:1) to obtain 37.5 mg of diol compound (7a) (yield: 76%).

Synthesis Example E1-4 (Step E: $R^2$=Phenyl)

Synthesis of 2-(dimethylphosphono)methyl-1,3-propanediol (7a)

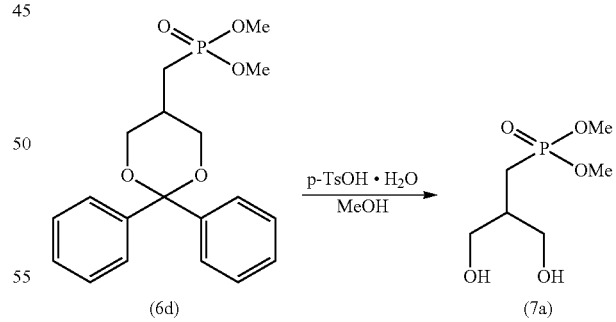

The phosphonic acid dimethyl compound (6d) obtained in Synthesis Example D1-4 (621 mg) was dissolved in 5.1 mL of methanol, and 16.3 mg of p-toluenesulfonic acid monohydrate was further added thereto, followed by stirring at 0° C. for 15 hours and at 20° C. for 1 hour. Then, methanol in the reaction solution was distilled off under reduced pressure. The resulting residue was purified with silica gel chromatography (chloroform:methanol=10:1) to obtain 226 mg of diol compound (7a) (yield: 67%).

Synthesis Example E2-1 (Step E: $R^2$=Ethyl)

Synthesis of 2-(diethylphosphono)methyl-1,3-propanediol (7a-1)

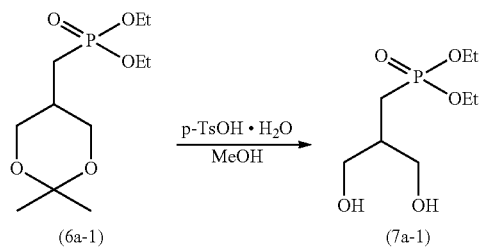 [SMILES: "MeOH" ; CCOP(=O)(CC1COC(C)(C)OC1)OCC ; CCOP(=O)(CC(CO)CO)OCC]

The phosphonic acid diethyl compound (6a-1) obtained in Synthesis Example D5-1 (2.00 g) was dissolved in 15 mL of methanol, and 428.6 mg of p-toluenesulfonic acid monohydrate was further added thereto, followed by stirring at 20° C. for 3 hours, and then at 0° C. overnight. Methanol in the reaction solution was distilled off under reduced pressure, and the resulting residue was purified with silica gel chromatography (chloroform:methanol=5:1) to obtain 1.69 g of diol compound (7a-1) (yield: 99%).

$^1$H-NMR (500 MHz, CDCl$_3$)

δ: 1.34 (t, J=7 Hz, 6H), 1.91 (dd, J=18.5, 7 Hz, 2H), 2.14 (m, 1H), 3.20 (br, hydroxyl group), 3.77 (d, J=5 Hz, 4H), 4.12 (m, 4H)

Synthesis Example E2-2 (Step E: $R^2$=n-Butyl)

Synthesis of 2-(dibutylphosphono)methyl-1,3-propanediol (7a-2)

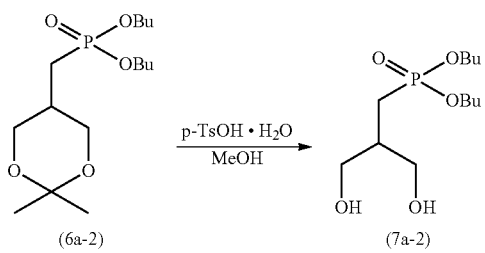

The phosphonic acid dibutyl compound (6a-2) obtained in Synthesis Example D5-2 (2.50 g) was dissolved in 15.5 mL of methanol, and 442.5 mg of p-toluenesulfonic acid monohydrate was further added thereto, followed by stirring at 20° C. for 8 hours. Methanol in the reaction solution was distilled off under reduced pressure. The resulting residue was purified with silica gel chromatography (chloroform:methanol=15:1) to obtain 2.13 g of diol compound (7a-2) (yield: 97%).

$^1$H-NMR (500 MHz, CDCl$_3$)

δ: 0.94 (t, J=7.5 Hz, 6H), 1.41 (tq, J=7.5, 7.5 Hz, 4H), 1.66 (tt, J=8, 8 Hz, 4H), 1.90 (dd, J=19, 7 Hz, 2H), 2.12 (m, 1H), 3.76 (m, 4H), 4.04 (m, 4H)

Synthesis Example E2-3 (Step E: $R^2$=Benzyl)

Synthesis of 2-(dibenzylphosphono)methyl-1,3-propanediol (7a-3)

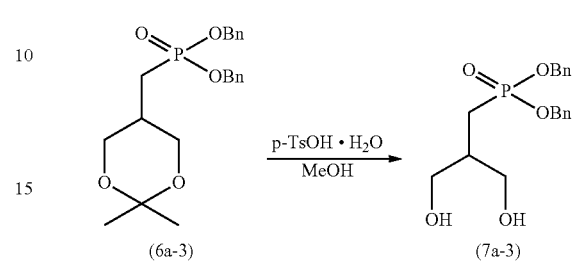

The phosphonic acid dibenzyl compound (6a-3) obtained in Synthesis Example D5-3 (1.58 g) was dissolved in 8.1 mL of methanol, and 230.9 mg of p-toluenesulfonic acid monohydrate was further added thereto, followed by stirring at 20° C. for 3 hours, and then at 0° C. overnight. Methanol in the reaction solution was distilled off under reduced pressure. The resulting residue was purified with silica gel chromatography (chloroform:methanol=10:1) to obtain 1.2/g of diol compound (7a-3) (yield: 89%).

$^1$H-NMR (500 MHz, CDCl$_3$)

δ: 1.92 (dd, J=19, 7 Hz, 2H), 2.05 (m, 1H), 3.70 (m, 4H), 5.01 (m, 4H), 7.34 (m, 10H)

Step (F)

Synthesis Example F1-1 (Step F: Base=DBU, Solvent=DMF)

Synthesis of (2-methoxy-2-oxo-2λ$^5$-[1,2]oxaphosphoran-4-yl)methanol (8a)

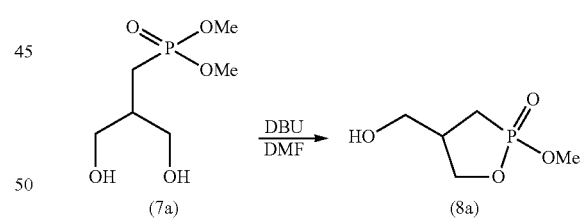

The diol compound (7a) obtained in Synthesis Example E1-1 (200.0 mg) was dissolved in 4 mL of DMF, and 45.3 μL of DBU was further added thereto, followed by stirring at 20° C. for 3 hours. Then, 57.6 mg of p-toluenesulfonic acid monohydrate was added to the reaction mixture to stop the reaction, and DMF in the reaction solution was distilled off under reduced pressure. The resulting residue was purified with silica gel chromatography (chloroform:methanol=9:1) to obtain 147.1 mg of cyclic phosphonic acid compound (8a) (yield: 88%).

$^1$H-NMR (500 MHz, CDCl$_3$)

δ: 1.73-2.07 (m, 3H), 2.35 (dd, J=5, 5 Hz, 1H), 2.68-2.88 (m, 1H), 3.65-3.73 (m, 2H), 3.79 (dd, J=11, 3.5 Hz, 3H), 3.89-4.37 (m, 2H)

Synthesis Example F1-2 (Step F: Base=DBU, Solvent=DMAc)

Synthesis of (2-methoxy-2-oxo-2λ$^5$-[1,2]oxaphosphoran-4-yl)methanol (8a)

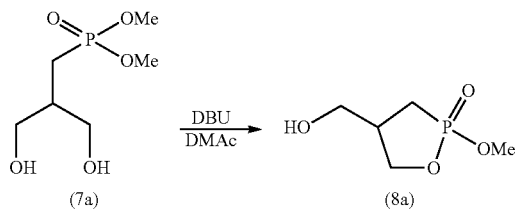

The diol compound (7a) obtained in Synthesis Example E1-1 (500 mg) was dissolved in 10.2 mL of dimethylformacetamide, and 113 μL of DBU was further added thereto, followed by stirring at 20° C. for 3 hours. The reaction was stopped with 144 mg of p-toluenesulfonic acid monohydrate, and dimethylformacetamide in the reaction solution was distilled off under reduced pressure. The resulting residue was purified with silica gel chromatography (chloroform:methanol=5:1) to obtain 212 mg of cyclic phosphonic acid compound (8a) (yield: 51%).

Synthesis Example F1-3 (Step F: Base=DBU, Solvent=Acetonitrile (AN))

Synthesis of (2-methoxy-2-oxo-2λ$^5$-[1,2]oxaphosphoran-4-yl)methanol (8a)

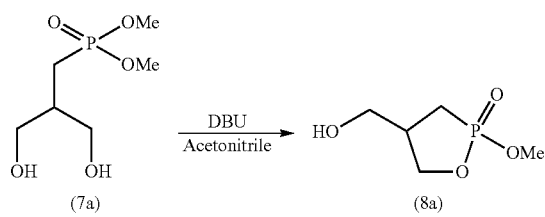 [SMILES: COP(=O)(CC(CO)CO)OC ; "DBU" ; "Acetonitrile" ; COP1(=O)CC(CO)CO1]

The diol compound (7a) obtained in Synthesis Example E1-1 (500 mg) was dissolved in 10.2 mL of acetonitrile, and 113 μL of DBU was further added thereto, followed by stirring at 20° C. for 3 hours. The reaction was stopped with 144 mg of p-toluenesulfonic acid monohydrate, and acetonitrile in the reaction solution was distilled off under reduced pressure. The resulting residue was purified with silica gel chromatography (chloroform:methanol=10:1) to obtain 235 mg of cyclic phosphonic acid compound (8a) (yield: 56%).

Synthesis Example F1-4 (Step F: Base=DBU, Solvent=Acetone)

Synthesis of (2-methoxy-2-oxo-2λ$^5$-[1,2]oxaphosphoran-4-yl)methanol (8a)

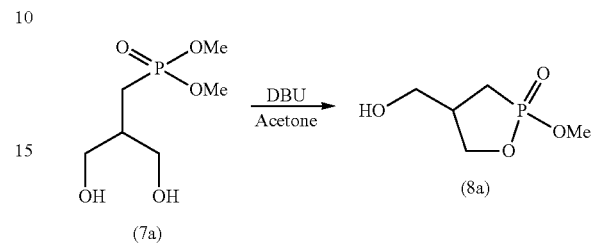

The diol compound (7a) obtained in Synthesis Example E1-1 (500 mg) was dissolved in 10.2 mL of acetone, and 113 μL of DBU was further added thereto, followed by stirring at 20° C. for 3 hours. The reaction was stopped with 144 mg of p-toluenesulfonic acid monohydrate, and acetone in the reaction solution was distilled off under reduced pressure. The resulting residue was purified with silica gel chromatography (chloroform:methanol=10:1) to obtain 224 mg of cyclic phosphonic acid compound (8a) (yield: 54%).

Synthesis Example F1-4 (Step F: Base=DBU, Solvent=Methanol)

Synthesis of (2-methoxy-2-oxo-2λ$^5$-[1,2]oxaphosphoran-4-yl)methanol (8a)

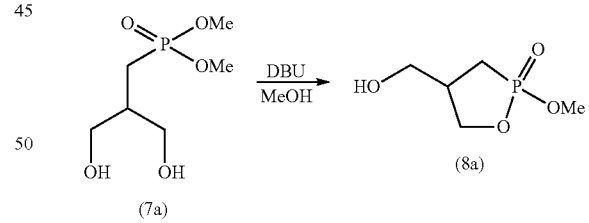

The diol compound (7a) obtained in Synthesis Example E1-1 (500 mg) was dissolved in 10.2 mL of methanol, and 113 μL of DBU was further added thereto, followed by stirring at 20° C. for 3 hours. The reaction was stopped with 144 mg of p-toluenesulfonic acid monohydrate, and methanol in the reaction solution was distilled off under reduced pressure. The resulting residue was purified with silica gel chromatography (chloroform:methanol=10:1) to obtain 86.8 mg of cyclic phosphonic acid compound (8a) (yield: 21%).

Synthesis Example F1-5 (Step F: Base=DBU, Solvent=Isopropanol)

Synthesis of (2-methoxy-2-oxo-2λ⁵-[1,2]oxaphosphoran-4-yl)methanol (8a)

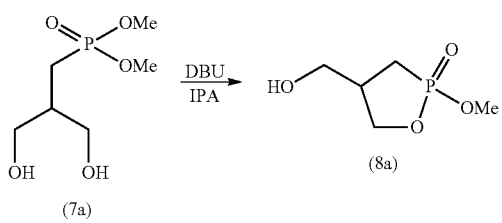

The diol compound (7a) obtained in Synthesis Example E1-1 (500 mg) was dissolved in 10.2 mL of isopropanol, and 113 μL of DBU was further added thereto, followed by stirring at 20° C. for 3 hours. The reaction was stopped with 144 mg of p-toluenesulfonic acid monohydrate, and isopropanol in the reaction solution was distilled off under reduced pressure. The resulting residue was purified with silica gel chromatography (chloroform:methanol=10:1) to obtain 75 mg of cyclic phosphonic acid compound (8a) (yield: 18%).

Synthesis Example F1-6 (Step F: Base=DBU, Solvent=Butanol)

Synthesis of (2-methoxy-2-oxo-2λ⁵-[1,2]oxaphosphoran-4-yl)methanol (8a)

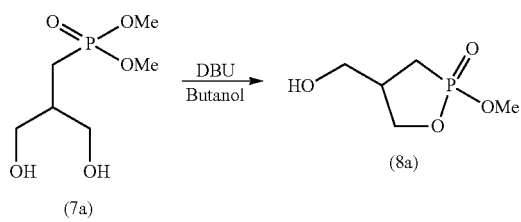

The diol compound (7a) obtained in Synthesis Example E1-1 (500 mg) was dissolved in 10.2 mL of butanol, and 113 μL of DBU was further added thereto, followed by stirring at 20° C. for 3 hours. The reaction was stopped with 144 mg of p-toluenesulfonic acid monohydrate, and butanol in the reaction solution was distilled off under reduced pressure. The resulting residue was purified with silica gel chromatography (chloroform:methanol=10:1) to obtain 121 mg of cyclic phosphonic acid compound (5a) (yield: 29%).

Synthesis Example F1-7 (Step F: Base=DBU, Solvent=DMF/acetonitrile)

Synthesis of (2-methoxy-2-oxo-2λ⁵-[1,2]oxaphosphoran-4-yl) methanol (8a)

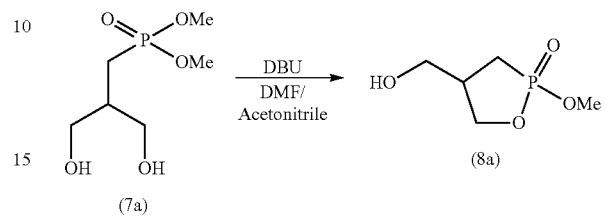

The diol compound (7a) obtained in Synthesis Example E1-1 (500 mg) was dissolved in 5.1 mL of DMF and 5.1 mL of acetonitrile. Then, 113 μL of DBU was further added thereto, followed by stirring at 20° C. for 3 hours. The reaction was stopped with 144 mg of p-toluenesulfonic acid monohydrate, and DMF and acetonitrile in the reaction solution were distilled off under reduced pressure. The resulting residue was purified with silica gel chromatography (chloroform:methanol=10:1) to obtain 170 mg of cyclic phosphonic acid compound (5a) (yield: 41%).

Synthesis Example F2-1 (Step F: Base=DBU (0.3 Eq.), Solvent=DMF)

Synthesis of (2-methoxy-2-oxo-2λ⁵-[1,2]oxaphosphoran-4-yl) methanol (8a)

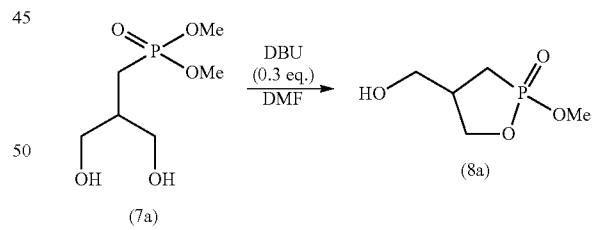

The diol compound (7a) obtained in Synthesis Example E1-1 (500.0 mg) was dissolved in 10 mL of DMF, and 113 μL of DBU was further added thereto, followed by stirring at 20° C. for 3 hours. The reaction was stopped with 144 mg of p-toluenesulfonic acid monohydrate, and DMF was distilled off under reduced pressure. The resulting residue was purified with silica gel chromatography (chloroform:methanol=15:1) to obtain 304.7 mg of cyclic phosphonic acid compound (8a) (yield: 73%).

Synthesis Example F2-2 (Step F: Base=DBN (0.3 Eq.), Solvent=DMF)

Synthesis of (2-methoxy-2-oxo-2λ⁵-[1,2]oxaphosphoran-4-yl)methanol (8a)

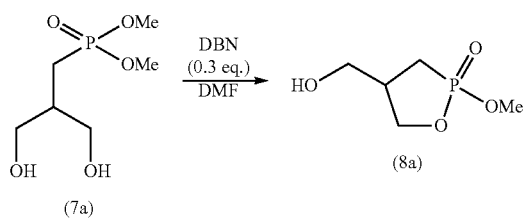

The diol compound (7a) obtained in Synthesis Example E1-1 (500.0 mg) was dissolved in 10 mL of DMF, and 90 μL of DBN was further added thereto, followed by stirring at 20° C. for 4 hours. The reaction was stopped with 144 mg of p-toluenesulfonic acid monohydrate, and DMF in the reaction solution was distilled off under reduced pressure. The resulting residue was purified with silica gel chromatography (chloroform:methanol=15:1) to obtain 307.2 mg of cyclic phosphonic acid compound (8a) (yield: 73%).

Synthesis Example F2-3 (Step F: Base=TEA (0.3 Eq.), Solvent=DMF)

Synthesis of (2-methoxy-2-oxo-2λ⁵-[1,2]oxaphosphoran-4-yl)methanol (8a)

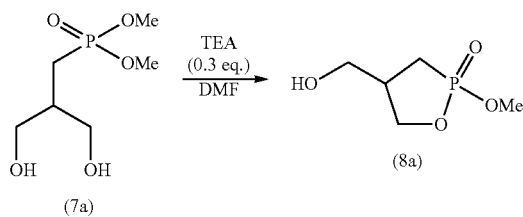

The diol compound (7a) obtained in Synthesis Example E1-1 (500.0 mg) was dissolved in 10 mL of DMF, and 105 μL of TEA was further added thereto. Then, the resulting mixture was heated to increase the temperature from 20° C. to a reflux temperature, followed by stirring for 2.5 hours. The reaction was stopped with 144 mg of p-toluenesulfonic acid monohydrate, and DMF in the reaction solution was distilled off under reduced pressure. The resulting residue was purified with silica gel chromatography (chloroform:methanol=15:1) to obtain 216.2 mg of cyclic phosphonic acid compound (8a) (yield: 52%).

Synthesis Example F2-4 (Step F: Base=DIPEA (0.3 Eq.), Solvent=DMF)

Synthesis of (2-methoxy-2-oxo-2λ⁵-[1,2]oxaphosphoran-4-yl)methanol (8a)

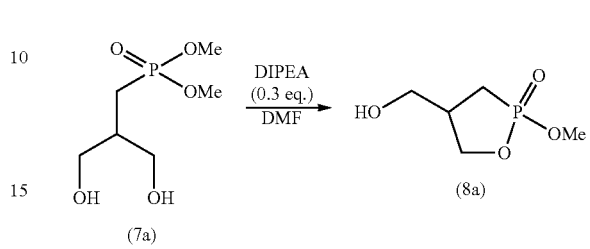

The diol compound (7a) obtained in Synthesis Example E1-1 (500.0 mg) was dissolved in 10 mL of DMF, and 132 μL of DIPEA was further added thereto. Then, the resulting mixture was heated to increase the temperature from 20° C. to a reflux temperature, followed by stirring for 2.5 hours. The reaction was stopped with 144 mg of p-toluenesulfonic acid monohydrate, and DMF in the reaction solution was distilled off under reduced pressure. The resulting residue was purified with silica gel chromatography (chloroform:methanol=15:1) to obtain 226.1 mg of cyclic phosphonic acid compound (8a) (yield: 54%).

Synthesis Example F2-5 (Step F: Base=NaOMe (0.3 Eq.), Solvent=DMF)

Synthesis of (2-methoxy-2-oxo-2λ⁵-[1,2]oxaphosphoran-4-yl) methanol (8a)

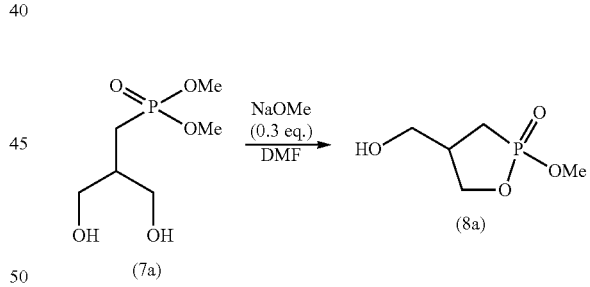

The diol compound (7a) obtained in Synthesis Example E1-1 (500.0 mg) was dissolved in 10 mL of DMF, and 40.9 mg of sodium methoxide was further added thereto, followed by stirring at 20° C. for 3 hours. The reaction was stopped with 144 mg of p-toluenesulfonic acid monohydrate, and DMF in the reaction solution was distilled off under reduced pressure. Then, 10 mL of chloroform was added to the residue. A white salt was filtered, and the white solid was washed with 10 mL of chloroform, and the filtrate was concentrated. The resulting residue was purified with silica gel chromatography (chloroform:methanol=15:1) to obtain 258.1 mg of cyclic phosphonic acid compound (8a) (yield: 62%).

Synthesis Example F2-6 (Step F: Base=NaOEt (0.3 Eq.), Solvent=DMF)

Synthesis of (2-methoxy-2-oxo-2$\lambda^5$-[1,2]oxaphosphoran-4-yl)methanol (8a)

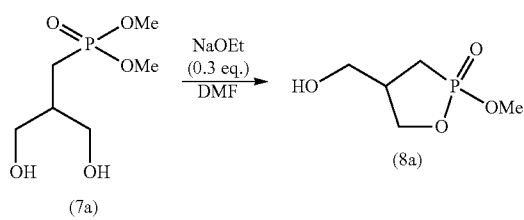

The diol compound (7a) obtained in Synthesis Example E1-1 (770.7 mg) was dissolved in 15.4 mL of DMF, and 79.4 mg of sodium ethoxide was further added thereto, followed by stirring at 20° C. for 3 hours. The reaction was stopped with 221.9 mg of p-toluenesulfonic acid monohydrate, and DMF in the reaction solution was distilled off under reduced pressure. Then, 20 mL of chloroform was added to the residue. A white salt was filtered, the white solid was washed with 20 mL of chloroform, and the filtrate was concentrated. The resulting residue was purified with silica gel chromatography (chloroform:methanol=15:1) to obtain 349.0 mg of cyclic phosphonic acid compound (8a) (yield: 54%).

Synthesis Example F2-7 (Step F: Base=t-BuOK (0.3 Eq.), Solvent=DMF)

Synthesis of (2-methoxy-2-oxo-2$\lambda^5$-[1,2]oxaphosphoran-4-yl)methanol (8a)

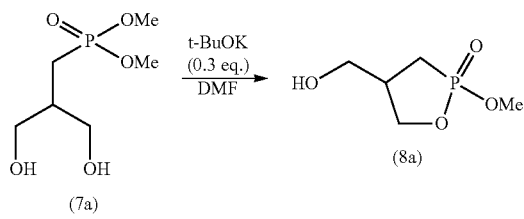

The diol compound (7a) obtained in Synthesis Example E1-1 (500.0 mg) was dissolved in 10 mL of DMF, and 84.9 mg of potassium tert-butoxide was further added thereto, followed by stirring at 20° C. for 3 hours. The reaction was stopped with 144 mg of p-toluenesulfonic acid monohydrate, and DMF in the reaction solution was distilled off under reduced pressure. Then, 10 mL of chloroform was added to the residue. A white salt was filtered, the white solid was washed with 10 mL of chloroform, and the filtrate was concentrated. The resulting residue was purified with silica gel chromatography (chloroform:methanol=15:1) to obtain 193.8 mg of cyclic phosphonic acid compound (8a) (yield: 46%).

Synthesis Example F2-8 (Step F: Base=t-BuONa (0.3 Eq.), Solvent=DMF)

Synthesis of (2-methoxy-2-oxo-2-[1,2]oxaphosphoran-4-yl)methanol (8a)

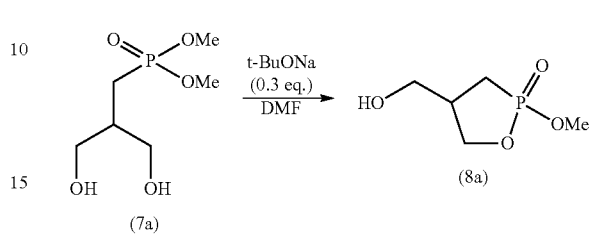

The diol compound (7a) obtained in Synthesis Example E1-1 (500.0 mg) was dissolved in 10 mL of DMF, and 72.7 mg of sodium tert-butoxide was further added thereto, followed by stirring at 20° C. for 3 hours. The reaction was stopped with 144 mg of p-toluenesulfonic acid monohydrate, and the precipitated white solid was filtered. After the white solid was washed with 5 mL of DMF, DMF was distilled off from the filtrate under reduced pressure. Then, 10 mL of chloroform was added to the residue. A white salt was filtered. After washing with 10 mL of chloroform, the filtrate was concentrated. The resulting residue was purified with silica gel chromatography (chloroform:methanol=15:1) to obtain 200.6 mg of cyclic phosphonic acid compound (8a) (yield: 48%).

Synthesis Example F2-9 (Step F: Base=CsCO$_3$ (0.3 Eq.), Solvent=DMF)

Synthesis of (2-methoxy-2-oxo-2$\lambda^5$-[1,2]oxaphosphoran-4-yl)methanol (8a)

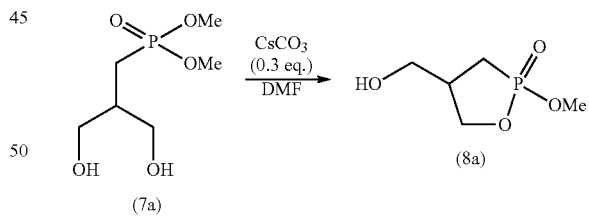

The diol compound (7a) obtained in Synthesis Example E1-1 (500.0 mg) was dissolved in 10 mL of DMF, and 246.6 mg of cesium carbonate was further added thereto, followed by stirring at 20° C. for 3 hours. The reaction was stopped with 144 mg of p-toluenesulfonic acid monohydrate, and DMF in the reaction solution was distilled off under reduced pressure. Then, 10 mL of chloroform was added to the residue. A white salt was filtered. After the white solid was washed with 10 mL of chloroform, the filtrate was concentrated. The resulting residue was purified with silica gel chromatography (chloroform:methanol=15:1) to obtain 35.1 mg of cyclic phosphonic acid compound (8a) (yield: 8%).

Synthesis Example F2-10 (Step F: Base=NaH (0.3 Eq.), Solvent=DMF)

Synthesis of (2-methoxy-2-oxo-2λ⁵-[1,2]oxaphosphoran-4-yl)methanol (8a)

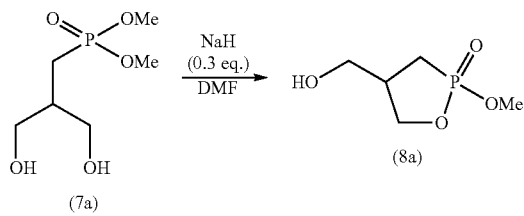

The diol compound (7a) obtained in Synthesis Example E1-1 (500.0 mg) was dissolved in 10 mL of DMF, and 30.3 mg of sodium hydride was further added thereto, followed by stirring at 20° C. for 3 hours. The reaction was stopped with 144 mg of p-toluenesulfonic acid monohydrate, and DMF in the reaction solution was distilled off under reduced pressure. Then, 10 mL of chloroform was added to the residue. A white salt was filtered. After the white solid was washed with 10 mL of chloroform, the filtrate was concentrated. The resulting residue was purified with silica gel chromatography (chloroform:methanol=15:1) to obtain 190.2 mg of cyclic phosphonic acid compound (8a) (yield: 45%).

Synthesis Example F3-1 (Step F: Quenching Agent=CSA)

Synthesis of (2-methoxy-2-oxo-2λ⁵-[1,2]oxaphosphoran-4-yl)methanol (8a)

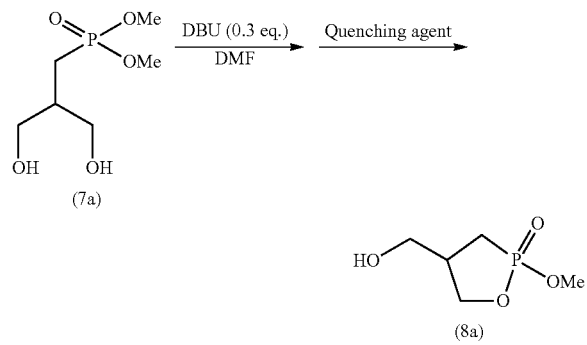

The diol compound (7a) obtained in Synthesis Example E1-1 (500.0 mg) was dissolved in 10 mL of DMF, and 113 μL of DBU was further added thereto, followed by stirring at 20° C. for 3 hours. The reaction was stopped with 175.9 mg of camphorsulfonic acid (CSA), and DMF in the reaction solution was distilled off under reduced pressure. The resulting residue was purified with silica gel chromatography (chloroform:methanol=15:1) to quantitatively obtain 554.2 mg of cyclic phosphonic acid compound (8a).

Synthesis Example F3-2 (Step F: Quenching Agent=Formic Acid)

The diol compound (7a) obtained in Synthesis Example E1-1 (500.0 mg) was dissolved in 10 mL of DMF, and 113 μL of DBU was further added thereto, followed by stirring at 20° C. for 3 hours. The reaction was stopped with 30 μL of formic acid, and DMF in the reaction solution was distilled off under reduced pressure. The resulting residue was purified with silica gel chromatography (chloroform:methanol=15:1) to obtain 305.6 mg of cyclic phosphonic acid compound (8a) (yield: 73%).

Synthesis Example F3-3 (Step F: Quenching Agent=Acetic Acid)

The diol compound (7a) obtained in Synthesis Example E1-1 (500.0 mg) was dissolved in 10 mL of DMF, and 113 μL of DBU was further added thereto, followed by stirring at 20° C. for 3 hours. The reaction was stopped with 43 μL of acetic acid, and DMF in the reaction solution was distilled off under reduced pressure. The resulting residue was purified with silica gel chromatography (chloroform:methanol=15:1) to obtain 289.6 mg of cyclic phosphonic acid compound (8a) (yield: 69%).

Synthesis Example F3-4 (Step F: Quenching Agent=Propionic Acid)

The diol compound (7a) obtained in Synthesis Example E1-1 (500.0 mg) was dissolved in 10 mL of DMF, and 113 μL of DBU was further added thereto, followed by stirring at 20° C. for 3 hours. The reaction was stopped with 57 μL of propionic acid, and DMF in the reaction solution was distilled off under reduced pressure. The resulting residue was purified with silica gel chromatography (chloroform:methanol=15:1) to obtain 303.0 mg of cyclic phosphonic acid compound (8a) (yield: 72%).

Synthesis Example F3-5 (Step F: Quenching Agent=Butyric Acid)

The diol compound (7a) obtained in Synthesis Example E1-1 (500.0 mg) was dissolved in 10 mL of DMF, and 113 μL of DBU was further added thereto, followed by stirring at 20° C. for 3 hours. The reaction was stopped with 69 μL of butyric acid, and DMF in the reaction solution was distilled off under reduced pressure. The resulting residue was purified with silica gel chromatography (chloroform:methanol=15:1) to obtain 303.3 mg of cyclic phosphonic acid compound (8a) (yield: 72%).

Synthesis Example F3-6 (Step F: Quenching Agent=Trifluoroacetic Acid)

The diol compound (7a) obtained in Synthesis Example E1-1 (500.0 mg) was dissolved in 10 mL of DMF, and 113 UL of DBU was further added thereto, followed by stirring at 20° C. for 3 hours. The reaction was stopped with 58 μL of trifluoroacetic acid, and DMF in the reaction solution was distilled off under reduced pressure. The resulting residue was purified with silica gel chromatography (chloroform:methanol=15:1) to obtain 288.4 mg of cyclic phosphonic acid compound (8a) (yield: 69%).

Synthesis Example F4-1 (Step F: Base=DBU, Solvent=Acetonitrile (AN))

Synthesis of (2-ethoxy-2-oxo-2$\lambda^5$-[1,2]oxaphosphoran-4-yl)methanol (8a-1)

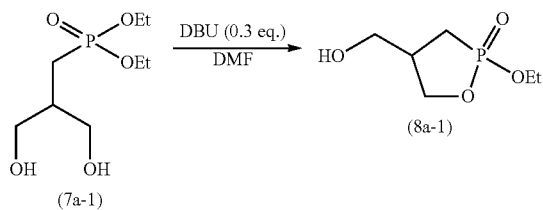

The diol compound (7a-1) obtained in Synthesis Example E2-1 (1.50 g) was dissolved in 26.5 mL of DMF, and 297 UL of DBU was further added thereto, followed by stirring at 20° C. for 3 hours. Further, 200 µL of DBU was added to this solution, and the resulting mixture was stirred at 20° C. for 2 hours. Subsequently, the reaction was stopped with 630.7 mg of p-toluenesulfonic acid monohydrate, and DMF in the reaction solution was distilled off under reduced pressure. The resulting residue was purified with silica gel chromatography (chloroform:methanol=15:1), the obtained fraction was dissolved again in 25.1 mL of DMF, and 282 µL of DBU was added thereto, followed by stirring at 20° C. for 4 hours. Further, 282 µL of DBU was added to this solution, and the resulting mixture was stirred at 20° C. for 3 hours. Additionally, 282 µL of DBU was added thereto, and the resulting mixture was stirred at 20° C. for 3 hours. The reaction was then stopped with 1.08 g of p-toluenesulfonic acid monohydrate, and DMF in the reaction solution was distilled off under reduced pressure. The resulting residue was purified with silica gel chromatography (chloroform:methanol=15:1) to obtain 781.6 mg of cyclic phosphonic acid compound (8a-1) (yield: 69%).

$^1$H-NMR (500 MHz, CDCl$_3$)

δ: 1.35 (t, J=7 Hz, 3H), 1.75 (m, 1H), 1.85 (br, Hydroxyl group), 2.00 (m, 1H), 2.15 (br, Hydroxyl group), 2.78 (m, 1H), 3.70 (m, 2H), 3.89-4.36 (m, 4H)

Synthesis Example F4-2 (Step F: Base=DBU, Solvent=Acetonitrile (AN))

Synthesis of (2-ethoxy-2-oxo-2$\lambda^5$-[1,2]oxaphosphoran-4-yl)methanol (8a-1)

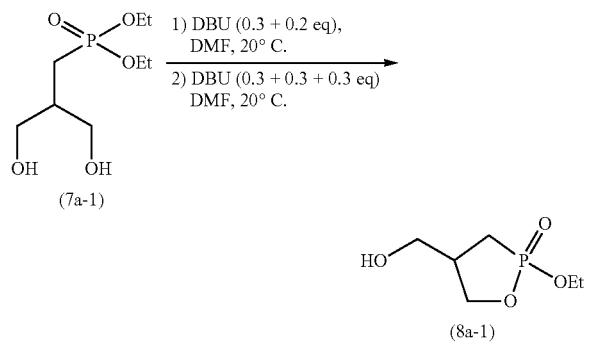

The diol compound (7a-1) obtained in Synthesis Example E2-1 (1.50 g) was dissolved in 26.5 mL of DMF, and 297 µL of DBU was further added thereto, followed by stirring at 20° C. for 3 hours. Further, 200 µL of DBU was added to this solution, and the resulting mixture was stirred at 20° C. for 2 hours. Subsequently, the reaction was stopped with 630.7 mg of p-toluenesulfonic acid monohydrate, and DMF in the reaction solution was distilled off under reduced pressure. The resulting residue was purified with silica gel chromatography (chloroform:methanol=15:1), the obtained fraction was dissolved again in 25.1 mL of DMF, and 282 µL of DBU was added thereto, followed by stirring at 20° C. for 4 hours. Further, 282 µL of DBU was added to this solution, and the resulting mixture was stirred at 20° C. for 3 hours. Additionally, 282 µL of DBU was added thereto, and the resulting mixture was stirred at 20° C. for 3 hours. The reaction was then stopped with 1.08 g of p-toluenesulfonic acid monohydrate, and DMF in the reaction solution was distilled off under reduced pressure. The resulting residue was purified with silica gel chromatography (chloroform:methanol=15:1) to obtain 781.6 mg of cyclic phosphonic acid compound (8a-1) (yield: 69%).

Synthesis Example F4-3 (Step F: R$^2$=n-Bu)

Synthesis of (2-butoxy-2-oxo-2$\lambda^5$-[1,2]oxaphosphoran-4-yl)methanol (8a-2)

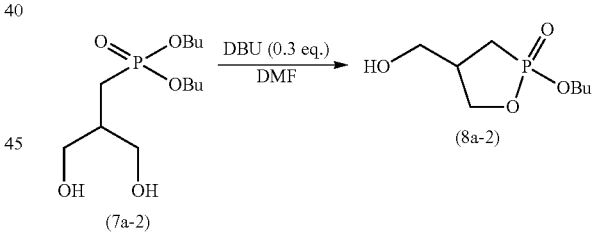

The diol compound (7a-2) obtained in Synthesis Example E2-2 (1.72 g) was dissolved in 24.4 mL of DMF, and 911 µL of DBU was further added thereto, followed by stirring at 60° C. for 5 hours. The reaction was then stopped with 1.16 g of p-toluenesulfonic acid monohydrate, and DMF in the reaction solution was distilled off under reduced pressure. The resulting residue was purified with silica gel chromatography (chloroform:methanol=10:1) to obtain 1.03 g of cyclic phosphonic acid compound (8a-2) (yield: 81%).

$^1$H-NMR (500 MHz, CDCl$_3$)

δ: 0.94 (t, J=7.5 Hz, 6H), 1.40 (tq, J=7.5, 7.5 Hz, 4H), 1.64-1.79 (m, 3H), 2.00 (m, 1H), 2.36 (br, Hydroxyl group), 2.69-2.89 (m, 1H), 3.70 (m, 2H), 3.89-4.36 (m, 2H), 4.10 (m, 2H)

Synthesis Example F4-4 (Step F: $R^1$=Benzyl)

Synthesis of (2-benzyloxy-2-oxo-2$\lambda^5$-[1,2]oxaphosphoran-4-yl)methanol (8a-3)

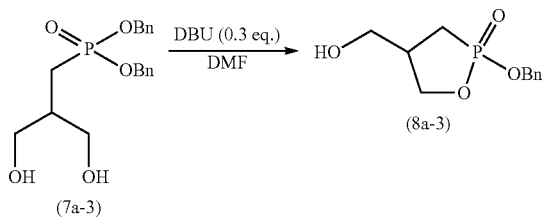

The diol compound (7a-3) obtained in Synthesis Example E2-3 (350.4 mg) was dissolved in 4 mL of DMF, and 45 μL of DBU was further added thereto, followed by stirring at 20° C. for 3 hours. Subsequently, the reaction was stopped with 57.1 mg of p-toluenesulfonic acid monohydrate, and DMF in the reaction solution was distilled off under reduced pressure. The resulting residue was purified with silica gel chromatography (chloroform:methanol=5:1) to obtain 188.5 mg of cyclic phosphonic acid compound (8a-3) (yield: 78%).

$^1$H-NMR (500 MHz, CDCl$_3$)

δ: 1.65-2.06 (m, 2H), 2.66-2.80 (m, 1H), 3.61-3.67 (m, 2H), 3.88-4.36 (m, 2H), 5.12 (m, 2H), 7.33-7.41 (m, 5H)

Step (G)

Synthesis Example G1-1 (Step G: Solvent=Dichloromethane)

Synthesis of 9-octadecenoic acid (9Z)-(2-methoxy-2-oxo-2$\lambda^5$-[1,2]oxaphosphoran-4-yl)methyl Ester (9a)

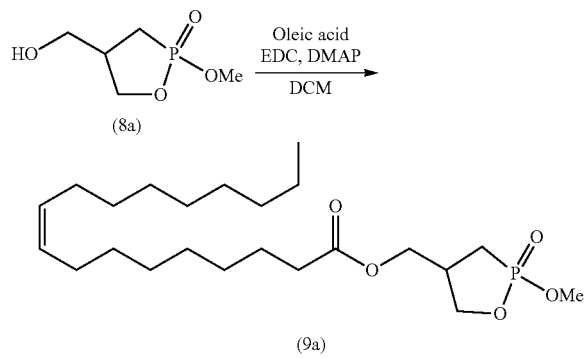

The cyclic phosphonic acid compound (8a) obtained in Synthesis Example F1-1 (300.0 mg) was dissolved in 6.0 mL of dichloromethane. Then, 510.1 mg of oleic acid and 66.2 mg of DMAP were further added thereto, followed by cooling to 0° C. Subsequently, 415.4 mg of EDC was added to this solution, and the resulting mixture was stirred at room temperature for 2.5 hours. The reaction was stopped with 10 mL of 1N hydrochloric acid, and after the layers were separated, extraction was performed with 10 mL of dichloromethane, and again with 5 mL of dichloromethane, followed by washing of the organic phases with 10 mL of 1% brine. Thereafter, dichloromethane was distilled off under reduced pressure, and purification was performed by silica gel chromatography (only ethyl acetate) to obtain 649.8 mg of phosphonic acid ester compound (9a) (yield: 84%).

$^1$H-NMR (500 MHz, CDCl$_3$):

δ: 0.88 (t, J=6.5 Hz, 3H), 1.27-1.30 (m, 20H), 1.60-1.76 (m, 3H) 2.01-2.12 (m, 5H), 2.32 (t, J=7.5 Hz, 2H), 2.83-2.97 (m, 1H), 3.78-4.34 (m, 7H), 5.31-5.38 (m, 2H)

Synthesis Example G1-2 (Step G: Solvent=Toluene)

Synthesis of 9-octadecenoic acid (9Z)-(2-methoxy-2-oxo-2$\lambda^5$-[1,2]oxaphosphoran-4-yl) methyl Ester (9a)

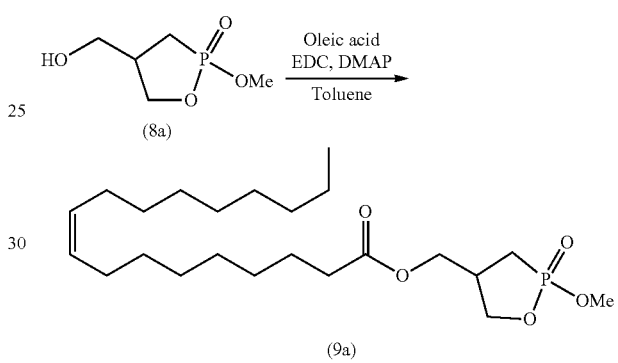

The cyclic phosphonic acid compound (8a) obtained in Synthesis Example F1-1 (300.0 mg) was dissolved in 6.0 mL of toluene. Then, 510.1 mg of oleic acid and 66.2 mg of DMAP were further added thereto, followed by cooling to 0° C. Subsequently, 415.4 mg of EDC was added to this solution, and the resulting mixture was stirred at room temperature for 4 hours. The reaction was stopped with 10 mL of 1N hydrochloric acid, and 2 mL of methanol was added thereto. After the layers were separated, extraction was performed 3 times with 10 mL of toluene, followed by washing of the organic phases with 10 mL of 1% brine. Thereafter, toluene was distilled off under reduced pressure, and purification was performed by silica gel chromatography (only ethyl acetate) to obtain 369.1 mg of phosphonic acid ester compound (9a) (yield: 47%).

Synthesis Example G1-3 (Step G: Solvent=THF)

Synthesis of 9-octadecenoic acid (9Z)-(2-methoxy-2-oxo-2$\lambda^5$-[1,2]oxaphosphoran-4-yl)methyl Ester (9a)

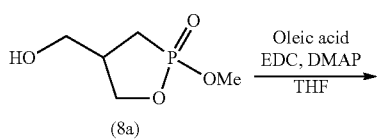

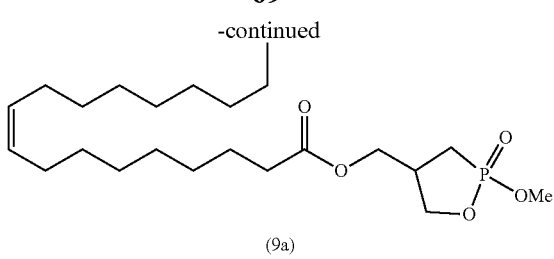

(9a)

The cyclic phosphonic acid compound (8a) obtained in Synthesis Example F1-1 (300.0 mg) was dissolved in 6.0 mL of tetrahydrofuran. Then, 510.1 mg of oleic acid and 66.2 mg of DMAP were further added thereto, followed by cooling to 0° C. Subsequently, 415.4 mg of EDC was added to this solution, and the resulting mixture was stirred at room temperature for 4 hours. Then, tetrahydrofuran was distilled off under reduced pressure, and 10 mL of dichloromethane and 10 mL of 1N hydrochloric acid were added thereto. After the resulting mixture was separated into layers, extraction was performed twice with 10 mL of dichloromethane, followed by washing of the organic phases with 10 mL of 1% brine. Thereafter, dichloromethane was distilled off under reduced pressure, and purification was performed by silica gel chromatography (only ethyl acetate) to obtain 509.6 mg of phosphonic acid ester compound (9a) (yield: 66%).

Synthesis Example G1-4 (Step G: Solvent=DMF)

Synthesis of 9-octadecenoic acid (9Z)-(2-methoxy-2-oxo-2λ$^5$-[1,2]oxaphosphoran-4-yl)methyl Ester (9a)

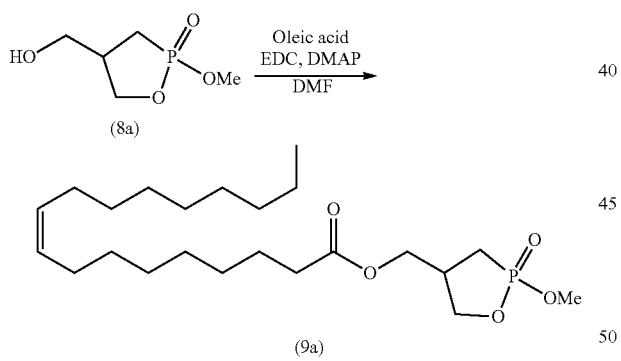

(8a)

(9a)

The cyclic phosphonic acid compound (8a) obtained in Synthesis Example F1-1 (300.0 mg) was dissolved in 6.0 mL of N,N-dimethylformamide. Then, 510.1 mg of oleic acid and 66.2 mg of DMAP were further added thereto, followed by cooling to 0° C. Subsequently, 415.4 mg of EDC was added to this solution, and the resulting mixture was stirred at room temperature for 2.5 hours. Then, N,N-dimethylformamide was distilled off under reduced pressure, and 10 mL of dichloromethane and 10 mL of 1N hydrochloric acid were added thereto. After the resulting mixture was separated into layers, extraction was performed twice with 10 mL of dichloromethane, followed by washing of the organic phases with 10 mL of 1% brine. Thereafter, dichloromethane was distilled off under reduced pressure, and purification was performed by silica gel chromatography (only ethyl acetate) to obtain 603.4 mg of phosphonic acid ester compound (9a) (yield: 78%).

Synthesis Example G1-5 (Step G: Solvent=Ethyl Acetate)

Synthesis of 9-octadecenoic acid (9Z)-(2-methoxy-2-oxo-2λ$^5$-[1,2]oxaphosphoran-4-yl)methyl Ester (9a)

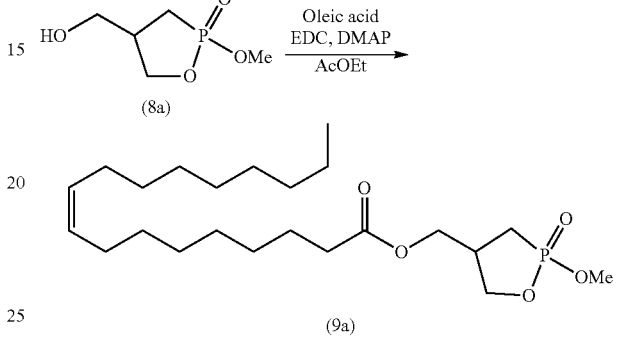

The cyclic phosphonic acid compound (8a) obtained in Synthesis Example F1-1 (300.0 mg) was dissolved in 6.0 mL of ethyl acetate. Then, 510.1 mg of oleic acid and 66.2 mg of DMAP were further added thereto, followed by cooling to 0° C. Subsequently, 415.4 mg of EDC was added to this solution, and the resulting mixture was stirred at room temperature for 24 hours. After the reaction was quenched with 10 mL of 1N hydrochloric acid, the resulting mixture was separated into layers, and extraction was performed twice with 10 mL of ethyl acetate, followed by washing of the organic phases with 10 mL of 1% brine. Thereafter, ethyl acetate was distilled off under reduced pressure, and purification was performed by silica gel chromatography (only ethyl acetate) to obtain 568.1 mg of phosphonic acid ester compound (9a) (yield: 73%).

Synthesis Example G2-1 (Step G: Condensation Agent=DCC)

Synthesis of 9-octadecenoic acid (9Z)-(2-methoxy-2-oxo-2λ$^5$-[1,2]oxaphosphoran-4-yl)methyl Ester (9a)

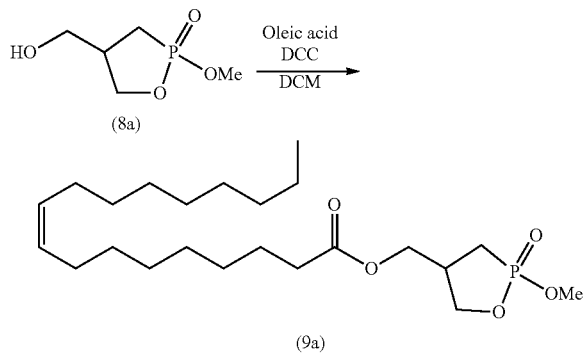

The cyclic phosphonic acid compound (8a) obtained in Synthesis Example F1-1 (300.0 mg) was dissolved in 6.0 mL of dichloromethane, and 510.1 mg of oleic acid was further added thereto. Subsequently, the solution was cooled to 0° C., and 447.2 mg of DCC was added thereto, followed by stirring at room temperature for 23 hours. The obtained white solid was separated by filtration, and washed with 3 mL of dichloromethane. Thereafter, the filtrate was concentrated under reduced pressure, and the residue was purified with silica gel chromatography (only ethyl acetate) to obtain 27.1 mg of phosphonic acid ester compound (9a) (yield: 3.5%).

Synthesis Example G2-2 (Step G: Condensation Agent=DCC, Additive=DMAP)

Synthesis of 9-octadecenoic acid (9Z)-(2-methoxy-2-oxo-2λ⁵-[1,2]oxaphosphoran-4-yl)methyl Ester (9a)

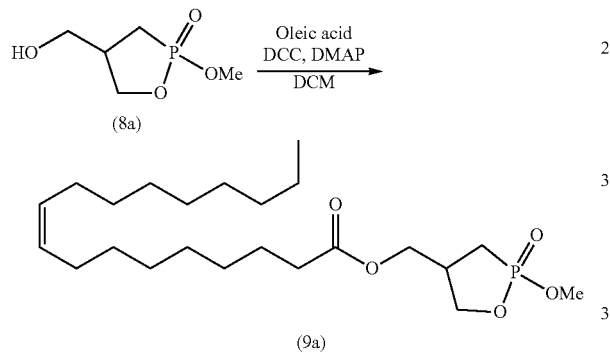

The cyclic phosphonic acid compound (8a) obtained in Synthesis Example F1-1 (300.0 mg) was dissolved in 6.0 mL of dichloromethane. Then, 510.1 mg of oleic acid and 66.2 mg of 4-DMAP were added thereto, followed by cooling to 0° C. Thereafter, 447.2 mg of DCC was added thereto, and the mixture was stirred at room temperature for 2 hours. The obtained white solid was separated by filtration, and washed with 15 mL of dichloromethane. Thereafter, the filtrate was concentrated under reduced pressure, and purification was performed by silica gel chromatography (only ethyl acetate) to obtain 458.0 mg of phosphonic acid ester compound (9a) (yield: 59%).

Synthesis Example G2-3 (Step G: Condensation Agent=DIC)

Synthesis of 9-octadecenoic acid (9Z)-(2-methoxy-2-oxo-2λ⁵-[1,2]oxaphosphoran-4-yl)methyl Ester (9a)

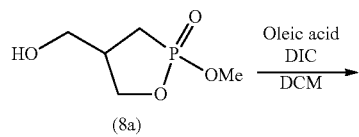

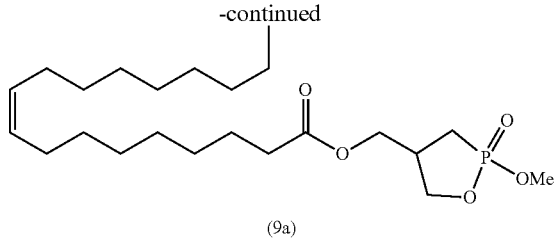

The cyclic phosphonic acid compound (8a) obtained in Synthesis Example F1-1 (300.0 mg) was dissolved in 6.0 mL of dichloromethane, and 510.1 mg of oleic acid was added thereto, followed by cooling to 0° C. Then, 339 μL of DIC was added thereto, followed by stirring at room temperature for 3 days. The obtained white solid was separated by filtration, and washed with 5 mL of dichloromethane. Thereafter, the filtrate was concentrated under reduced pressure, and purification was performed by silica gel chromatography (only ethyl acetate) to obtain 137.8 mg of phosphonic acid ester compound (9a) (yield: 18%).

Synthesis Example G2-4 (Step G: Condensation Agent=DIC, Additive=DMAP)

Synthesis of 9-octadecenoic acid (9Z)-(2-methoxy-2-oxo-2λ⁵-[1,2]oxaphosphoran-4-yl)methyl Ester (9a)

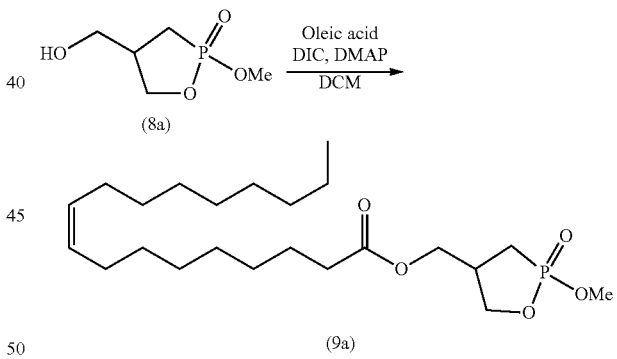

The cyclic phosphonic acid compound (5a) obtained in Synthesis Example F1-1 (300.0 mg) was dissolved in 6.0 mL of dichloromethane. Then, 510.1 mg of oleic acid and 66.2 mg of 4-DMAP were added thereto, followed by cooling to 0° C. Subsequently, 339 μL of DIC was added to this solution, followed by stirring at room temperature for 24 hours. The obtained white solid was separated by filtration, and washed with 5 mL of dichloromethane. Thereafter, the filtrate was concentrated under reduced pressure, and purification was performed by silica gel chromatography (only ethyl acetate) to obtain 569.9 mg of phosphonic acid ester compound (9a) (yield: 73%).

Synthesis Example G3-1 (Step G: Reaction Using Oleyl Chloride)

Synthesis of 9-octadecenoic acid (9Z)-(2-methoxy-2-oxo-2λ⁵-[1,2]oxaphosphoran-4-yl)methyl Ester (9a)

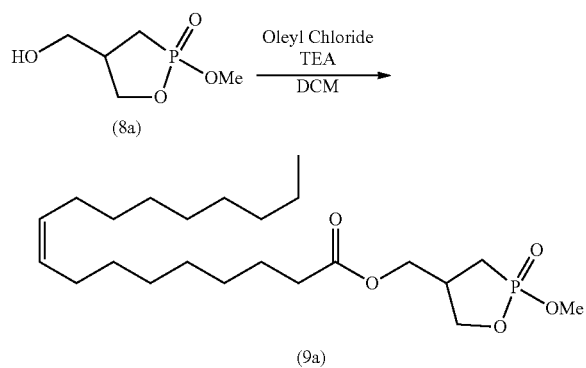

The cyclic phosphonic acid compound (8a) obtained in Synthesis Example F1-1 (300.0 mg) was dissolved in 6.0 mL of dichloromethane, and 376 μL of triethylamine was added thereto, followed by cooling to 0° C. Then, 717 UL of oleyl chloride was added thereto, followed by stirring at room temperature for 5.5 hours. After the reaction was quenched with 10 mL of water, extraction was performed twice with 10 mL of dichloromethane, followed by washing of the organic phases with 1% brine. Then, dichloromethane was distilled off under reduced pressure, and purification was performed by silica gel chromatography (only ethyl acetate) to obtain 658.4 mg of phosphonic acid ester compound (9a) (yield: 85%).

Synthesis Example G3-2 (Step G: Reaction Using Prepared Oleyl Chloride)

Synthesis of 9-octadecenoic acid (9Z)-(2-methoxy-2-oxo-2λ⁵-[1,2]oxaphosphoran-4-yl)methyl Ester (9a)

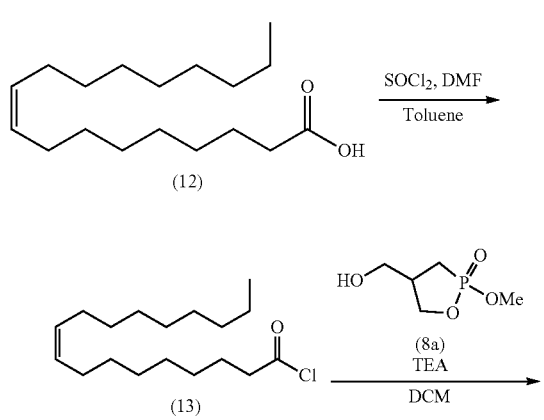

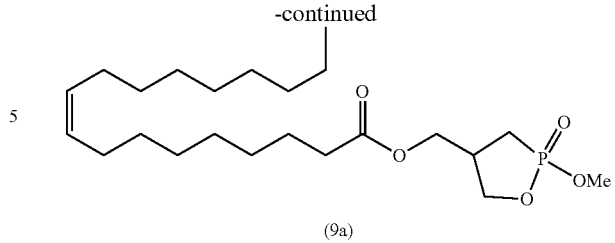

Oleic acid (510.1 mg) was dissolved in 6.0 mL of toluene, and 7 μL of N,N-dimethylformamide and 156 μL of thionyl chloride were added thereto, followed by stirring at 40° C. for 2 hours. Subsequently, toluene was distilled off under reduced pressure. Then, 5 mL of toluene was added, toluene was distilled off again under reduced pressure, and the resulting product was dissolved in 3.0 mL of dichloromethane. Separately, 300.0 mg of cyclic phosphonic acid compound (8a) was dissolved in 3.0 mL of dichloromethane, and 376 μL of triethylamine was further added thereto. After ice-cooling, the prepared oleyl chloride in dichloromethane (3.0 mL) was added thereto dropwise, followed by stirring at room temperature for 3 hours. After the reaction was quenched with 10 mL of water, extraction was performed twice with 10 mL of dichloromethane, and the organic phases were washed with 1% brine. Dichloromethane was distilled off under reduced pressure, and purification was performed by silica gel chromatography (only ethyl acetate) to obtain 571.2 mg of phosphonic acid ester compound (9a) (yield: 73%).

Synthesis Example G3-3 (Step G: Reaction Using Prepared Oleyl Chloride)

Synthesis of 9-octadecenoic acid (9Z)-(2-methoxy-2-oxo-2λ⁵-[1,2]oxaphosphoran-4-yl)methyl Ester (9a)

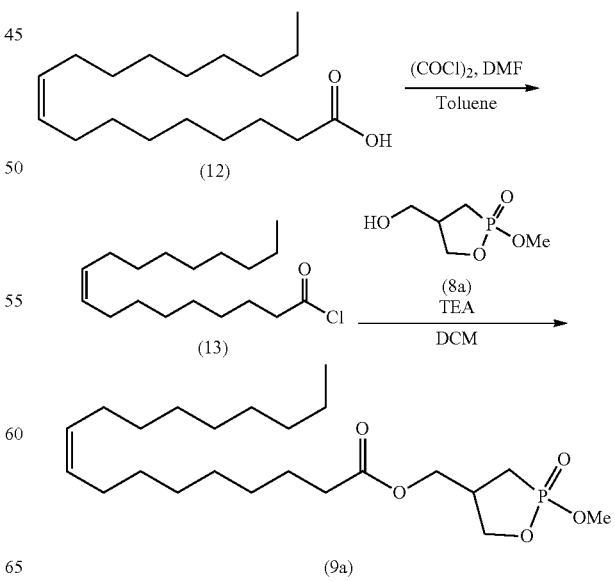

Oleic acid (510.1 mg) was dissolved in 6.0 mL of toluene, and 7 µL of N,N-dimethylformamide and 190 µL of oxalyl dichloride were added thereto. The resulting mixture was stirred at 40° C. for 3.5 hours, and toluene was distilled off under reduced pressure. Then, 5 mL of toluene was added, toluene was distilled off again under reduced pressure, and the resulting product was dissolved in 3.0 mL of dichloromethane. Separately, 300.0 mg of cyclic phosphonic acid compound (8a) was dissolved in 3.0 mL of dichloromethane, 376 µL of triethylamine was further added thereto, and after ice-cooling, the acid chloride prepared with 3.0 mL of dichloromethane was added thereto dropwise, followed by stirring at room temperature for 2 hours. After the reaction was quenched with 10 mL of water, extraction was performed twice with 10 mL of dichloromethane, and the organic phases were washed with 10 mL of water. Dichloromethane was distilled off under reduced pressure, and purification was performed by silica gel chromatography (only ethyl acetate) to obtain 515.6 mg of phosphonic acid ester compound (9a) (yield: 66%).

Synthesis Example G4-1 (Step G: Reaction Using p-Toluenesulfonyl Chloride)

Synthesis of 9-octadecenoic acid (9Z)-(2-methoxy-2-oxo-2λ$^5$-[1,2]oxaphosphoran-4-yl)methyl Ester (9a)

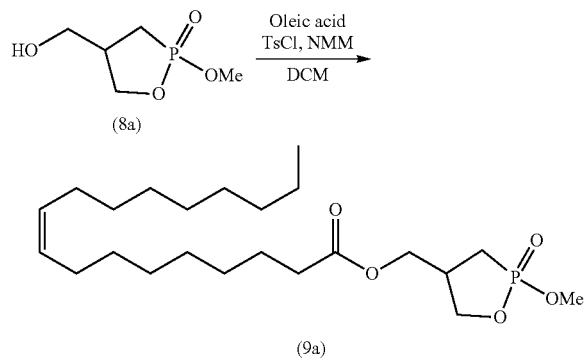

Oleic acid (510.1 mg) was dissolved in 3.0 mL of dichloromethane, and 430 µL of N-methylimidazole (NMM) was further added thereto. After cooling to 0° C., the resulting mixture was stirred at 0° C. for 1 hour. Subsequently, 3.0 mL of a solution of 300.0 mg of cyclic phosphonic acid compound (8a) in dichloromethane was added thereto dropwise, followed by stirring at 0° C. for 1.5 hours. After the reaction was quenched with 10 mL of water, extraction was performed twice with 10 mL of dichloromethane, and the organic phases were washed with 1% brine. Dichloromethane was distilled off under reduced pressure, and purification was performed by silica gel chromatography (only ethyl acetate) to obtain 603.8 mg of phosphonic acid ester compound (9a) (yield: 78%).

Synthesis Example G4-2 (Step G: Reaction Using Mukaiyama Reagent)

Synthesis of 9-octadecenoic acid (9Z)-(2-methoxy-2-oxo-2λ$^5$-[1,2]oxaphosphoran-4-yl)methyl Ester (9a)

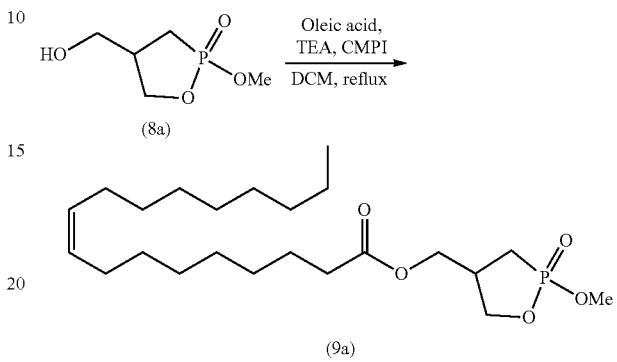

The cyclic phosphonic acid compound (8a) (421.9 mg) and oleic acid (717.4 mg) were dissolved in 8.5 mL of dichloromethane. Then, 845 µL of triethylamine and 778.7 mg of 2-chloro-1-methylpyridinium iodide (CMPI) were further added thereto, followed by heating under reflux for 3 hours. After the reaction was quenched with 10 mL of water, extraction was performed twice with 10 mL of dichloromethane. Dichloromethane was distilled off under reduced pressure, and purification was performed by silica gel chromatography (only ethyl acetate) to obtain 263.8 mg of phosphonic acid ester compound (9a) (yield: 34%).

Synthesis Example G4-3 (Step G: Reaction Using pyBop)

Synthesis of 9-octadecenoic acid (9Z)-(2-methoxy-2-oxo-2λ$^5$-[1,2]oxaphosphoran-4-yl)methyl Ester (9a)

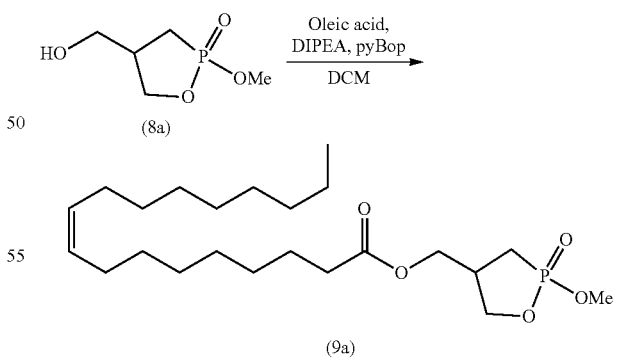

The cyclic phosphonic acid compound (8a) (200.0 mg) and oleic acid (340.1 mg) were dissolved in 4.0 mL of dichloromethane, followed by addition of 420 µL of diisopropylethylamine. After ice-cooling, 752 mg of pyBop was added thereto, and the mixture was stirred at room temperature for 6 hours. After the reaction was quenched with 5 mL of 1 N hydrochloric acid, extraction was performed twice with 10 mL and 5 mL of dichloromethane, and the organic phases were washed with 10 mL of water. Dichloromethane was distilled off under reduced pressure, and purification was performed by silica gel chromatography (only ethyl acetate) to obtain 513.8 mg of phosphonic acid ester compound (9a) (yield: 99%).

Synthesis Example G4-4 (Step G: Reaction Using HATU)

Synthesis of 9-octadecenoic acid (9Z)-(2-methoxy-2-oxo-2λ$^5$-[1,2]oxaphosphoran-4-yl)methyl Ester (9a)

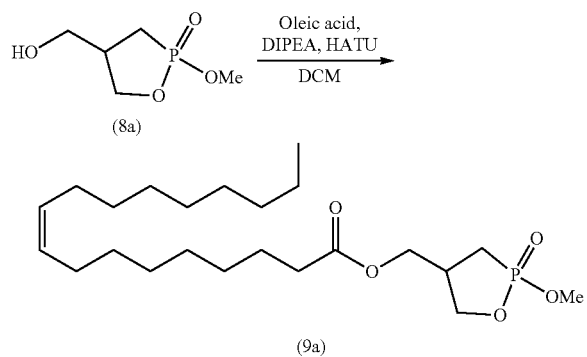

The cyclic phosphonic acid compound (8a) (300.0 mg) and oleic acid (510.1 mg) were dissolved in 6.0 mL of dichloromethane, and 630 μL of diisopropylethylamine was further added thereto. After ice-cooling, 824.0 mg of HATU was added thereto, and the mixture was stirred at room temperature for 24 hours. After the reaction was quenched with 10 mL of 1 N hydrochloric acid, extraction was performed twice with 10 mL of dichloromethane, and the organic phases were washed with 10 mL of water. Dichloromethane was distilled off under reduced pressure, and purification was performed by silica gel chromatography (only ethyl acetate) to obtain 513.2 mg of phosphonic acid ester compound (9a) (yield: 68%).

Synthesis Example G4-5 (Step G: Reaction Using HBTU)

Synthesis of 9-octadecenoic acid (9Z)-(2-methoxy-2-oxo-2λ$^5$-[1,2]oxaphosphoran-4-yl)methyl Ester (9a)

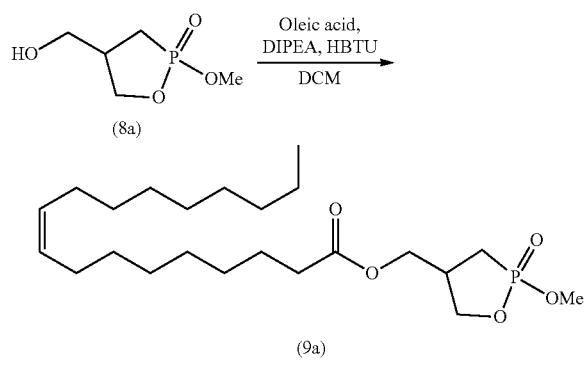

The cyclic phosphonic acid compound (5a) (300.0 mg) and oleic acid (510.1 mg) was dissolved in 6.0 mL of dichloromethane, and 630 μL of diisopropylethylamine was further added thereto. After ice-cooling, 822.0 mg of HBTU was added thereto, and the mixture was stirred at room temperature for 6.5 hours. After the reaction was quenched with 10 mL of 1N hydrochloric acid, extraction was performed twice with 10 mL of dichloromethane, and the organic phases were washed with 10 mL of water. Dichloromethane was distilled off under reduced pressure, and purification was performed by silica gel chromatography (only ethyl acetate) to obtain 612.0 mg of phosphonic acid ester compound (9a) (yield: 79%).

Synthesis Example G4-6 (Step G: Reaction Using COMU)

Synthesis of 9-octadecenoic acid (9Z)-(2-methoxy-2-oxo-2λ$^5$-[1,2]oxaphosphoran-4-yl)methyl Ester (9a)

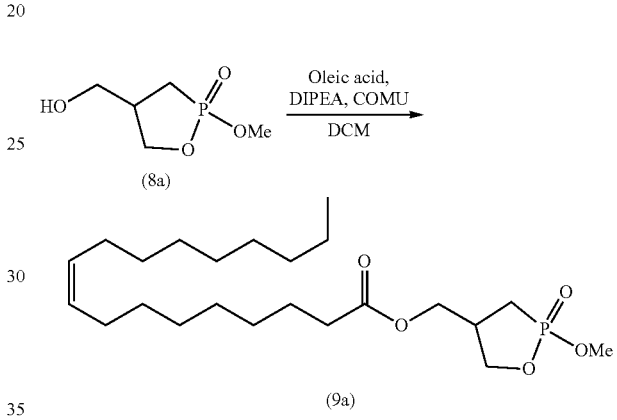

The cyclic phosphonic acid compound (8a) (300.0 mg) and oleic acid (510.1 mg) were dissolved in 6.0 mL of dichloromethane, and 630 μL of diisopropylethylamine was further added thereto. After ice-cooling, 928.1 mg of COMU was added thereto, and the mixture was stirred at room temperature for 24 hours. Subsequently, the reaction was quenched with 10 mL of 1 N hydrochloric acid, extraction was performed twice with 10 mL of dichloromethane, and the organic phases were washed with 10 mL of water. Dichloromethane was distilled off under reduced pressure, and purification was performed by silica gel chromatography (only ethyl acetate) to quantitatively obtain 778.2 mg of phosphonic acid ester compound (9a).

Synthesis Example G5 (Telescoping Method)

Synthesis of 9-octadecenoic acid (9Z)-(2-methoxy-2-oxo-2λ$^5$-[1,2]oxaphosphoran-4-yl)methyl Ester (9a)

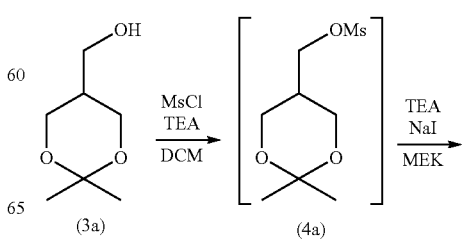

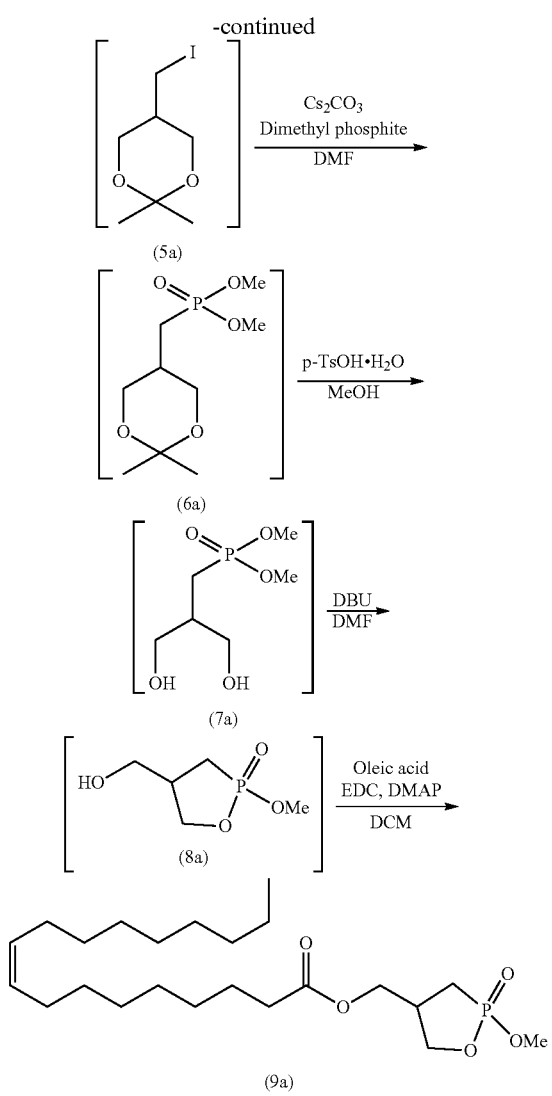

(5a)
(6a)
(7a)
(8a)
(9a)

Step B

The compound (3a) (30.0 g) was dissolved in 456 mL of $CH_2Cl_2$, and 42.7 mL of triethylamine was added thereto, followed by cooling to −20° C. Then, 19.1 mL of MsCl was added thereto, and the resulting mixture was stirred at −2° C. for 1 hour. The reaction was stopped with 250 mL of water, and the layers were separated, after which the water layer was extracted with 150 mL of $CH_2Cl_2$, and the organic layer was washed with 200 mL of water.

Step C

The organic layer was concentrated under reduced pressure, and the obtained residue was dissolved in 684 mL of methyl ethyl ketone. Then, 1.42 mL of triethylamine and 46.14 g of sodium iodide were added thereto, and the mixture was allowed to react under heating at reflux for 2.5 hours. After the reaction solution was cooled, methyl ethyl ketone was distilled off under reduced pressure, 300 mL of $CH_2Cl_2$ and 300 mL of water were added thereto, and the resulting mixture was separated into layers. After the water layer was extracted twice with 150 mL of of $CH_2Cl_2$, the organic layers were washed with 2.5% sodium thiosulfate and 300 mL of 0.5% sodium bicarbonate water. The resulting product was then separated into layers and washed with 300 mL of water, and the organic layer was concentrated under reduced pressure.

Step D

The resulting residue was dissolved in 410 mL of DMF. Then, 133.73 g of cesium carbonate and 37.64 mL of dimethyl phosphite were added thereto, and the mixture was allowed to react at 50° C. for 3 hours. DMF in the reaction solution was distilled off under reduced pressure, 300 mL of toluene was added thereto, and a white solid was filtered.

Step E

After the white solid was washed with 150 mL of toluene, the filtrate was concentrated under reduced pressure, and the resulting residue was dissolved in 410 mL of methanol. Then, 1.95 g of p-toluenesulfonic acid monohydrate was added to this solution, and the resulting mixture was stirred at 20° C. for 2 hours.

Step F

The reaction solution was concentrated under reduced pressure, and the resulting residue was dissolved in 821 mL of DMF. Then, 9.21 mL of DBU was added thereto, and the resulting mixture was stirred at 20° C. for 3 hours. Further, 11.71 g of p-toluenesulfonic acid monohydrate was added to this solution to stop the reaction, and DMF was distilled off under reduced pressure.

Step G

The resulting residue was dissolved in 684 mL of $CH_2Cl_2$. Then, 57.97 g of oleic acid, 7.52 g of DMAP, and 47.21 g of EDC were further added thereto, and the mixture was allowed to react at 20° C. for 12 hours. Subsequently, 300 mL of 1 N hydrochloric acid was added thereto, and the resulting mixture was separated into layers. The water layer was extracted twice with 300 mL of $CH_2Cl_2$, and the organic layers were washed with 300 mL of water and then concentrated. The resulting residue was purified with silica gel chromatography (eluted only with ethyl acetate) to obtain 61.99 g of compound (9a) (yield: 70%) (all steps).

Step (H)

Example 1 Production of 2ccPA Crystal (Good Solvent: Water, Poor Solvent: Acetone)

The cyclic phosphonic acid ester (9a) (1.0 g) obtained by the production method of Synthesis Example G5 was dissolved in 11.6 mL of methyl ethyl ketone. Then, 522.3 mg of sodium iodide was added thereto, and the mixture was allowed to react under heating at reflux for 14 hours. After the reaction, the reaction solution was concentrated and then dissolved at 60° C. in 5 mL of water, followed by cooling to 20° C. Thereafter, 20 mL of acetone was added to this solution dropwise, and the mixture was aged for 1 hour. The resulting crystal was filtered, washed with 30 mL of acetone, and dried under reduced pressure to obtain 651.0 mg of 2ccPA with a purity of 98.874%.

The following shows the X-ray powder diffraction spectrum of the obtained 2ccPA white crystal. The X-ray powder diffraction spectrum was obtained by copper radiation of λ=1.54059 Å through a monochromator.

| d (Interplanar spacing) | Relative intensity ($I/I_0$) |
|---|---|
| 16.1724 | 98 |
| 9.6675 | 28 |
| 4.9186 | 21 |
| 4.8335 | 23 |
| 4.5164 | 100 |
| 4.1835 | 14 |
| 3.7921 | 10 |

IR spectrum ($cm^{-1}$): 2920, 2851, 1728, 1204, 1176, 1098, 1012, 774, 744, 721
Melting point: 189° C.

Example 2 Production of 2ccPA Crystal (Good Solvent: Methanol, Poor Solvent: Acetone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13 hours. After the reaction, the reaction solution was concentrated and dissolved at 40° C. in 2.5 mL of methanol, followed by cooling to 10° C. Subsequently, 2.5 mL of acetone was added to this solution dropwise. After the temperature was increased to 20° C., 7.5 mL of acetone was added thereto dropwise, and the mixture was aged for 1 hour. Thereafter, the resulting crystal was filtered, washed with 30 mL of acetone, and dried under reduced pressure to obtain 907.6 mg of 2ccPA with a purity of 98.880%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity ($I/I_0$) |
|---|---|
| 15.9390 | 100 |
| 9.5838 | 23 |
| 4.9294 | 22 |
| 4.7972 | 18 |
| 4.4982 | 95 |
| 4.1913 | 19 |
| 3.7953 | 9 |

IR spectrum ($cm^{-1}$): 2920, 2851, 1733, 1209, 1166, 1097, 1013, 774, 738, 722
Melting point: 188° C.

Example 3 Production of 2ccPA Crystal (Good Solvent: Methanol, Poor Solvent: Methyl Ethyl Ketone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13 hours. After the reaction, the reaction solution was concentrated and dissolved at 40° C. in 2.5 mL of methanol, followed by cooling to 10° C. Subsequently, 2.5 mL of methyl ethyl ketone was added to this solution dropwise. After the temperature was increased to 20° C., 7.5 mL of methyl ethyl ketone was added thereto, and the mixture was aged for 1 hour. Thereafter, the resulting crystal was filtered, washed with 30 mL of methyl ethyl ketone, and dried under reduced pressure to obtain 862.8 mg of 2ccPA with a purity of 98.944%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity ($I/I_0$) |
|---|---|
| 15.8817 | 92 |
| 9.5631 | 22 |
| 4.9186 | 24 |
| 4.7869 | 20 |
| 4.4937 | 100 |
| 4.1835 | 19 |
| 3.7794 | 9 |

IR spectrum ($cm^{-1}$): 2920, 2851, 1727, 1205, 1175, 1099, 1024, 773, 742, 721
Melting point: 187° C.

Example 4 Production of 2ccPA Crystal (Good Solvent: Methanol, Poor Solvent: Methyl Isobutyl Ketone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 12 hours. After the reaction, the reaction solution was concentrated and dissolved at 40° C. in 2.5 mL of methanol, followed by cooling to 10° C. Subsequently, 2.5 mL of methyl isobutyl ketone was added to this solution dropwise. After the temperature was increased to 20° C., 7.5 mL of methyl isobutyl ketone was added thereto dropwise, and the mixture was aged for 1 hour. Thereafter, the resulting crystal was filtered, washed with 30 mL of methyl isobutyl ketone, and dried under reduced pressure to obtain 819.1 mg of 2ccPA with a purity of 99.300%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity ($I/I_0$) |
|---|---|
| 15.8817 | 100 |
| 9.5631 | 23 |
| 4.9294 | 10 |
| 4.7920 | 10 |
| 4.4982 | 44 |
| 4.1874 | 10 |
| 3.8017 | 5 |

IR spectrum ($cm^{-1}$): 2920, 2851, 1735, 1210, 1165, 1096, 1012, 776, 738, 722
Melting point: 189° C.

Example 5 Production of 2ccPA Crystal (Good Solvent: Methanol, Poor Solvent: Methyl Ethyl Ketone:Acetone=1:1)

The cyclic phosphonic acid ester (9a) (1.0 g) obtained by the production method of G5 was dissolved in 11.6 mL of methyl ethyl ketone. Then, 522.3 mg of sodium iodide was added thereto and allowed to react under heating at reflux for 13.5 hours. After the reaction, the reaction solution was concentrated and then dissolved at 40° C. in 2.5 mL of methanol, followed by cooling to 10° C. Thereafter, 2.5 mL of a liquid mixture of acetone and methyl ethyl ketone was added to this solution dropwise. After the temperature was increased to 20° C., 7.5 mL of a liquid mixture of acetone and methyl ethyl ketone was added thereto dropwise, and the mixture was aged for 1 hour. Thereafter, the resulting crystal was filtered, washed with 30 mL of a liquid mixture of acetone and methyl ethyl ketone, and dried under reduced pressure to obtain 853.8 mg of 2ccPA with a purity of 98.880%.

The following shows the X-ray powder diffraction spectrum of the obtained 2ccPA white crystal. This X-ray powder diffraction spectrum was obtained by copper radiation of $\lambda=1.54059$ Å through a monochromator.

| d (Interplanar spacing) | Relative intensity ($I/I_0$) |
|---|---|
| 15.8817 | 100 |
| 9.5631 | 23 |
| 4.9186 | 14 |
| 4.7869 | 13 |
| 4.4937 | 57 |
| 4.1874 | 14 |
| 3.7921 | 7 |

IR spectrum ($cm^{-1}$): 2920, 2851, 1733, 1209, 1166, 1097, 1013, 775, 738, 722

Example 6 Production of 2ccPA Crystal (Good Solvent: Ethanol, Crystallization Temperature: 10° C.)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13 hours. After the reaction, the reaction solution was concentrated and dissolved at 60° C. in 7.5 mL of ethanol. The resulting mixture was cooled to 10° C. and aged for 1 hour. Thereafter, the resulting crystal was filtered, washed with 30 mL of acetone, and dried under reduced pressure to obtain 846.6 mg of 2ccPA with a purity of 98.890%.

The following shows the X-ray powder diffraction spectrum of the obtained 2ccPA white crystal. This X-ray powder diffraction spectrum was obtained by copper radiation of $\lambda=1.54059$ Å through a monochromator.

| d (Interplanar spacing) | Relative intensity ($I/I_0$) |
|---|---|
| 15.8248 | 100 |
| 9.5425 | 24 |
| 4.9078 | 18 |
| 4.7920 | 17 |
| 4.4937 | 78 |
| 4.1796 | 15 |
| 3.7762 | 8 |

IR spectrum ($cm^{-1}$): 2920, 2851, 1728, 1207, 1167, 1097, 1013, 774, 741, 721
Melting point: 189° C.

Example 7 Production of 2ccPA Crystal (Good Solvent: Ethanol, Crystallization Temperature: 20° C.)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 16 hours. After the reaction, the reaction solution was concentrated and dissolved at 65° C. in 6 mL of ethanol. The resulting mixture was cooled to 20° C. and aged for 1 hour. Thereafter, the resulting crystal was filtered, washed with 30 mL of acetone, and dried under reduced pressure to obtain 783.3 mg of 2ccPA with a purity of 98.997%.

The following shows the X-ray powder diffraction spectrum of the obtained 2ccPA white crystal. This X-ray powder diffraction spectrum was obtained by copper radiation of $\lambda=1.54059$ Å through a monochromator.

| d (Interplanar spacing) | Relative intensity ($I/I_0$) |
|---|---|
| 16.0548 | 100 |
| 9.6046 | 24 |
| 4.9294 | 7 |
| 4.8075 | 9 |
| 4.5073 | 29 |
| 4.2070 | 7 |
| 3.7857 | 4 |

IR spectrum ($cm^{-1}$): 2920, 2851, 1728, 1211, 1175, 1096, 1013, 775, 745, 722
Melting point: 190° C.

Example 8 Production of 2ccPA Crystal (Good Solvent: Ethanol, Poor Solvent: Acetone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13 hours. After the reaction, the reaction solution was concentrated and then dissolved at 60° C. in 6 mL of ethanol, followed by cooling to 20° C. After 6 mL of acetone was added to this solution dropwise, the mixture was aged for 2 hours. Thereafter, the resulting crystal was filtered, washed with 30 mL of acetone, and dried under reduced pressure to obtain 786.4 mg of 2ccPA with a purity of 99.054%.

The following shows the X-ray powder diffraction spectrum of the obtained 2ccPA white crystal. This X-ray powder diffraction spectrum was obtained by copper radiation of $\lambda=1.54059$ Å through a monochromator.

| d (Interplanar spacing) | Relative intensity ($I/I_0$) |
|---|---|
| 15.9967 | 100 |
| 9.6046 | 24 |
| 4.9349 | 19 |
| 4.8023 | 17 |
| 4.5073 | 76 |
| 4.1913 | 13 |
| 3.8017 | 7 |

IR spectrum ($cm^{-1}$): 2920, 2851, 1727, 1212, 1172, 1096, 1024, 776, 746, 721
Melting point: 189° C.

Example 9 Production of 2ccPA Crystal (Good Solvent: Methanol:Ethanol=1:1, Poor Solvent: Acetone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13.5 hours. After the reaction, the reaction solution was concentrated, dissolved at 60° C. in 2.5 mL of a liquid mixture of methanol and ethanol, and cooled to 10° C. After 2.5 mL of acetone was added thereto dropwise, the temperature was increased to 20° C., 7.5 mL of acetone was added thereto dropwise, and the mixture was aged for 1 hour. The resulting crystal was filtered, washed with 30 mL of acetone, and dried under reduced pressure to obtain 954.2 mg of 2ccPA with a purity of 98.812%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity ($I/I_0$) |
|---|---|
| 15.8817 | 100 |
| 9.5631 | 24 |
| 4.9294 | 8 |
| 4.7920 | 8 |
| 4.4982 | 37 |
| 4.1913 | 10 |
| 3.8017 | 5 |

IR spectrum ($cm^{-1}$): 2920, 2851, 1734, 1210, 1165, 1097, 1012, 775, 738, 722
Melting point: 189° C.

Example 10 Production of 2ccPA Crystal (Good Solvent: 1-Propanol, Crystallization Temperature: 10° C.)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13 hours. After the reaction, the reaction solution was concentrated and dissolved at 60° C. in 7.5 mL of 1-propanol. The resulting mixture was cooled to 10° C. and aged for 1 hour. Subsequently, the resulting crystal was filtered, washed with 70 mL of acetone, and dried under reduced pressure to obtain 645.0 mg of 2ccPA with a purity of 98.419%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity ($I/I_0$) |
|---|---|
| 15.9967 | 100 |
| 9.6046 | 24 |
| 4.9024 | 7 |
| 4.8075 | 12 |
| 4.5027 | 32 |
| 4.1835 | 7 |
| 3.7636 | 6 |

IR spectrum ($cm^{-1}$): 2920, 2851, 1727, 1207, 1170, 1098, 1014, 774, 745, 721
Melting point: 190° C.

Example 11 Production of 2ccPA Crystal (Good Solvent: 1-Propanol, Crystallization Temperature: 20° C.)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 14 hours. After the reaction, the reaction solution was concentrated and dissolved at 50° C. in 6.0 mL of 1-propanol. The resulting mixture was cooled to 20° C. and aged for 1 hour. Thereafter, the resulting crystal was filtered, washed with 30 mL of acetone, and dried under reduced pressure to obtain 866.5 mg of 2ccPA with a purity of 98.750%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity ($I/I_0$) |
|---|---|
| 16.0548 | 100 |
| 9.6255 | 24 |
| 4.9403 | 11 |
| 4.8023 | 12 |
| 4.5073 | 51 |
| 4.1992 | 11 |
| 3.7985 | 6 |

IR spectrum ($cm^{-1}$): 2920, 2851, 1727, 1205, 1174, 1098, 1023, 773, 743, 721
Melting point: 188° C.

Example 12 Production of 2ccPA Crystal (Good Solvent: 1-Propanol, Poor Solvent: Acetone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 15.5 hours. After the reaction, the reaction solution was concentrated and dissolved at 60° C. in 6.0 mL of 1-propanol, followed by cooling to 20° C. Then, 6.0 mL of acetone was added to this solution dropwise, and the mixture was aged at 20° C. for 1 hour. Thereafter, the resulting crystal was filtered, washed with 30 mL of acetone, and dried under reduced pressure to obtain 866.9 mg of 2ccPA with a purity of 98.902%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity ($I/I_0$) |
|---|---|
| 16.0548 | 100 |
| 9.6255 | 23 |
| 4.9349 | 9 |
| 4.8075 | 10 |
| 4.5073 | 35 |
| 4.1952 | 7 |
| 3.7857 | 4 |

IR spectrum ($cm^{-1}$): 2920, 2851, 1727, 1206, 1175, 1097, 1023, 774, 744, 721
Melting point: 187° C.

Example 13 Production of 2ccPA Crystal (Good Solvent: Isopropyl Alcohol, Crystallization Temperature: 20° C.)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 15 hours. After the reaction, the reaction solution was concentrated and dissolved at 65° C. in 6.0 mL of 1-propanol. The resulting mixture was cooled to 20° C. and aged for 1 hour. Thereafter, the resulting crystal was filtered, washed with 30 mL of acetone, and dried under reduced pressure to obtain 942.2 mg of 2ccPA with a purity of 98.588%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 15.9390 | 80 |
| 9.5631 | 20 |
| 4.9186 | 26 |
| 4.7972 | 21 |
| 4.4982 | 100 |
| 4.1874 | 17 |
| 3.7953 | 9 |

IR spectrum (cm⁻¹): 2920, 2851, 1727, 1212, 1175, 1095, 1023, 776, 746, 722
Melting point: 188° C.

Example 14 Production of 2ccPA Crystal (Good Solvent: Isopropyl Alcohol, Poor Solvent: Acetone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 14 hours. After the reaction, the reaction solution was concentrated and dissolved at 60° C. in 6.0 mL of isopropyl alcohol, followed by cooling to 20° C. Then, 6.0 mL of acetone was added to this solution dropwise, and the mixture was aged at 20° C. for 1 hour. Thereafter, the resulting crystal was filtered, washed with 30 mL of acetone, and dried under reduced pressure to obtain 915.8 mg of 2ccPA with a purity of 98.761%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 15.939 | 86 |
| 9.5838 | 21 |
| 4.9132 | 25 |
| 4.7920 | 21 |
| 4.4937 | 100 |
| 4.1874 | 17 |
| 3.7762 | 8 |

IR spectrum (cm⁻¹): 2921, 2851, 1727, 1212, 1175, 1095, 1023, 776, 745, 722
Melting point: 187° C.

Example 15 Production of 2ccPA Crystal (Good Solvent: 1-Butanol, Poor Solvent: Acetone)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 12 hours. After the reaction, the reaction solution was concentrated and dissolved at 65° C. in 6.0 mL of 1-butanol, followed by cooling to 20° C. Then, 6.0 mL of acetone was added to this solution dropwise, and the mixture was aged at 20° C. for 3.5 hours. Thereafter, the resulting crystal was filtered, washed with 30 mL of acetone, and dried under reduced pressure to obtain 598.9 mg of 2ccPA with a purity of 98.773%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 15.9967 | 100 |
| 9.6046 | 25 |
| 4.9024 | 8 |
| 4.8075 | 12 |
| 4.4982 | 36 |
| 4.1719 | 7 |
| 3.7293 | 6 |

IR spectrum (cm⁻¹): 2920, 2851, 1728, 1206, 1175, 1097, 1013, 774, 745, 721
Melting point: 189° C.

Example 16 Production of 2ccPA Crystal (Reaction Solvent and a Crystallization Solvent: Acetone)

The cyclic phosphonic acid ester (9a) (1.0 g) obtained by the production method of G5 was dissolved in 11.6 mL of acetone. Then, 522.3 mg of sodium iodide was added thereto, and the mixture was allowed to react under heating at reflux for 48 hours. After cooling to room temperature, the resulting crystal was filtered, washed with 30 mL of acetone, and dried under reduced pressure to obtain 898.0 mg of 2ccPA with a purity of 86.921%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 16.0548 | 100 |
| 9.6255 | 23 |
| 4.9349 | 27 |
| 4.8075 | 21 |
| 4.5073 | 99 |
| 4.1992 | 15 |
| 3.8145 | 8 |

IR spectrum (cm⁻¹) : 2920, 2851, 1727, 1211, 1175, 1095, 1023, 776, 746, 722
Melting point: 189° C.

Example 17 Production of 2ccPA Crystal (Reaction Solvent and Crystallization Solvent: Methyl Ethyl Ketone, Poor Solvent: Acetone)

The cyclic phosphonic acid ester (9a) (1.0 g) obtained by the production method of G5 was dissolved in 11.6 mL of acetone. Then, 522.3 mg of sodium iodide was added thereto, and the mixture was allowed to react under heating at reflux for 15 hours. After cooling to room temperature, 11.6 mL of acetone was added thereto dropwise, and the resulting crystal was filtered, washed with 30 mL of acetone, and dried under reduced pressure to obtain 950.7 mg of 2ccPA with a purity of 98.429%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 15.7684 | 67 |
| 9.5425 | 16 |
| 4.8282 | 27 |
| 4.4802 | 100 |

| d (Interplanar spacing) | Relative intensity (I/I$_0$) |
| --- | --- |
| 4.1757 | 16 |
| 3.7263 | 10 |

IR spectrum (cm$^{-1}$): 2920, 2851, 1727, 1211, 1175, 1096, 1015, 775, 744, 722
Melting point: 189° C.

Example 18 Production of 2ccPA Crystal (Reaction Solvent and Crystallization Solvent: Methyl Isobutyl Ketone)

The cyclic phosphonic acid ester (9a) (1.0 g) obtained by the production method of G5 was dissolved in 11.6 mL of acetone. Then, 522.3 mg of sodium iodide was added thereto, and the mixture was allowed to react under heating at reflux for 6 hours. After cooling to 10° C. and aging for 1 hour, the resulting crystal was filtered, washed with 30 mL of acetone, and dried under reduced pressure to obtain 950.7 mg of 2ccPA with a purity of 20.777%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I$_0$) |
| --- | --- |
| 15.9390 | 100 |
| 9.5838 | 26 |
| 4.9132 | 6 |
| 4.8023 | 8 |
| 4.4937 | 23 |
| 4.1641 | 6 |
| 3.7730 | 4 |

IR spectrum (cm$^{-1}$): 2921, 2852, 1731, 1208, 1174, 1094, 1011, 778, 745, 722
Melting point: 187° C.

Example 19 Production of 2ccPA Crystal (Good Solvent: Methanol, Poor Solvent: Ethyl Acetate)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13 hours. After the reaction, the reaction solution was concentrated and dissolved at 40° C. in 2.5 mL of methanol, followed by cooling to 10° C. Thereafter, 2.5 mL of ethyl acetate was added thereto dropwise. After the temperature was increased to 20° C., 7.5 mL of ethyl acetate was added dropwise, and the mixture was aged for 1 hour. Thereafter, the resulting crystal was filtered, washed with 30 mL of ethyl acetate, and dried under reduced pressure to obtain 719.8 mg of 2ccPA with a purity of 98.204%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I$_0$) |
| --- | --- |
| 15.9390 | 100 |
| 9.5838 | 22 |
| 4.9186 | 16 |
| 4.7920 | 13 |
| 4.4937 | 62 |
| 4.1835 | 13 |
| 3.7921 | 7 |

IR spectrum (cm$^{-1}$): 2920, 2851, 1728, 1208, 1166, 1097, 1013, 773, 738, 722
Melting point: 190° C.

Example 20 Production of 2ccPA Crystal (Good Solvent: Methanol, Poor Solvent: Butyl Acetate)

The cyclic phosphonic acid ester (9a) (1.0 g) obtained by the production method of G5 was dissolved in 11.6 mL of methyl ethyl ketone. Then, 522.3 mg of sodium iodide was added thereto, and the mixture was allowed to react under heating at reflux for 13 hours. After the reaction, the reaction solution was concentrated and dissolved at 40° C. in 2.5 mL of methanol, followed by cooling to 10° C. Thereafter, 2.5 mL of butyl acetate was added thereto dropwise. After the temperature was increased to 20° C., 7.5 mL of butyl acetate was added dropwise, and the mixture was aged for 1 hour. Then, the resulting crystal was filtered, washed with 30 mL of butyl acetate, and dried under reduced pressure to obtain 548.0 mg of 2ccPA with a purity of 98.350%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I$_0$) |
| --- | --- |
| 15.9390 | 100 |
| 9.5838 | 23 |
| 4.9240 | 9 |
| 4.7920 | 9 |
| 4.4982 | 36 |
| 4.1874 | 9 |
| 3.7921 | 5 |

IR spectrum (cm$^{-1}$): 2920, 2851, 1735, 1210, 1165, 1097, 1012, 776, 738, 722
Melting point: 189° C.

Example 21 Repurification of 2ccPA (Good Solvent: Methanol, Poor Solvent: Methyl Ethyl Ketone)

The 2ccPA (3.00 g) obtained in Example 2 was dissolved at 40° C. in 7.3 mL of methanol, and the solution was cooled to 10° C. After 1 hour of stirring, 7.3 mL of methyl ethyl ketone was added thereto dropwise. Thereafter, the temperature was increased to 20° C., and 22 mL of methyl ethyl ketone was added thereto dropwise again. After 1 hour of aging at 20° C., the resulting crystal was filtered and washed with 36 mL of methyl ethyl ketone to obtain 2.55 g of 2ccPA with a purity of 99.511%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I$_0$) |
| --- | --- |
| 16.0548 | 100 |
| 9.6255 | 24 |
| 4.9186 | 14 |

| d (Interplanar spacing) | Relative intensity (I/I₀) |
|---|---|
| 4.7920 | 14 |
| 4.4982 | 67 |
| 4.1835 | 14 |
| 3.7985 | 8 |

IR spectrum (cm$^{-1}$): 2920, 2851, 1735, 1210, 1165, 1096, 1012, 776, 738, 722
Melting point: 189° C.

Example 22 Repurification of 2ccPA (Good Solvent: Methanol, Poor Solvent: Ethyl Acetate)

The 2ccPA (3.00 g) obtained in Example 2 was dissolved at 40° C. in 7.3 mL of methanol, and the solution was cooled to 10° C. After 1 hour of stirring, 7.3 mL of ethyl acetate was added thereto dropwise. Thereafter, the temperature was increased to 20° C., 22 mL of ethyl acetate was added thereto dropwise again, and the mixture was aged at 20° C. for 1 hour. Subsequently, the resulting crystal was filtered and washed with 36 mL of ethyl acetate to obtain 2.52 g of 2ccPA with a purity of 99.610%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 16.0548 | 100 |
| 9.6255 | 24 |
| 4.9294 | 17 |
| 4.7972 | 15 |
| 4.5073 | 74 |
| 4.1874 | 15 |
| 3.7985 | 8 |

IR spectrum (cm$^{-1}$): 2920, 2851, 1735, 1210, 1165, 1097, 1012, 776, 738, 722
Melting point: 187° C.

Example 23 Repurification of 2ccPA (Good Solvent: Methanol, Poor Solvent: 1-Propanol)

The 2ccPA (3.00 g) obtained in Example 2 was dissolved at 40° C. in 7.3 mL of methanol, and the solution was cooled to 10° C. After 1 hour of stirring, 7.3 mL of 1-propanol was added thereto dropwise. Thereafter, the temperature was increased to 20° C., 22 mL of 1-propanol was added dropwise again, and the mixture was aged at 20° C. for 1 hour. Subsequently, the resulting crystal was filtered and washed with 36 mL of 1-propanol to obtain 1.67 g of 2ccPA with a purity of 99.628%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 16.0548 | 100 |
| 9.6255 | 24 |
| 4.9186 | 15 |
| 4.8075 | 15 |
| 4.4982 | 67 |
| 4.1835 | 13 |
| 3.8049 | 7 |

IR spectrum (cm$^{-1}$): 2920, 2851, 1734, 1210, 1166, 1097, 1012, 775, 738, 722
Melting point: 187° C.

Example 24 Repurification of 2ccPA (Good Solvent: Methanol, Poor Solvent: Methyl Acetate)

The 2ccPA (3.00 g) obtained in Example 2 was dissolved at 40° C. in 7.3 mL of methanol, and the solution was cooled to 10° C. After 1 hour of stirring, 7.3 mL of methyl acetate was added thereto dropwise. Thereafter, the temperature was increased to 20° C., 22 mL of methyl acetate was added dropwise again, and the mixture was aged at 20° C. for 1 hour. Subsequently, the resulting crystal was filtered and washed with 36 mL of methyl acetate to obtain 2.49 g of 2ccPA with a purity of 99.559%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 15.9967 | 100 |
| 9.6046 | 23 |
| 4.9240 | 11 |
| 4.8023 | 10 |
| 4.4982 | 44 |
| 4.1874 | 10 |
| 3.7985 | 5 |

IR spectrum (cm$^{-1}$): 2920, 2851, 1735, 1210, 1165, 1097, 1012, 776, 738, 722
Melting point: 189° C.

Example 25 Repurification of 2ccPA (Good Solvent: Methanol, Poor Solvent: Isopropyl Acetate)

The 2ccPA (3.00 g) obtained in Example 2 was dissolved at 40° C. in 7.3 mL of methanol, and the solution was cooled to 10° C. After 1 hour of stirring, 7.3 mL of isopropyl acetate was added thereto dropwise. Thereafter, the temperature was increased to 20° C., 22 mL of isopropyl acetate was added dropwise again, and the mixture was aged at 20° C. for 1 hour. Subsequently, the resulting crystal was filtered and washed with 36 mL of isopropyl acetate to obtain 2.37 g of 2ccPA with a purity of 99.549%.

The following shows the X-ray powder diffraction spectrum of the obtained 2ccPA white crystal. This X-ray powder diffraction spectrum was obtained by copper radiation of λ=1.54059 Å through a monochromator.

| d (Interplanar spacing) | Relative intensity (I/I₀) |
|---|---|
| 15.9390 | 100 |
| 9.5838 | 22 |
| 4.9186 | 10 |
| 4.7869 | 10 |
| 4.4937 | 45 |

-continued

| d (Interplanar spacing) | Relative intensity (I/I₀) |
|---|---|
| 4.1796 | 10 |
| 3.7985 | 5 |

IR spectrum (cm⁻¹): 2920, 2851, 1735, 1210, 1165, 1097, 1012, 776, 738, 722
Melting point: 187° C.

Example 26 (Synthesis of 2ccPA—Reaction Solvent: Acetone)

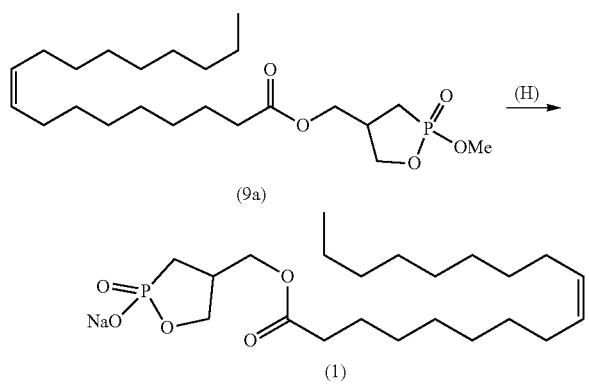

The cyclic phosphonic acid ester compound (9a) (200 mg) was dissolved in 2.3 mL of acetone. Then, 104.5 mg of sodium iodide was added thereto, and the mixture was allowed to react under heating at reflux for 23 hours. After cooling to 20° C., the generated white solid was filtered. The resulting crystal was washed with acetone to thus obtain 174.2 mg of white crystal of 2ccPA (1) (melting point of 189.6° C.).

¹H-NMR (500 MHz, CDCl₃)

δ: 0.79 (t, J=6.5 Hz), 1.19-1.23 (m, 20H), 1.36 (m, 1H), 1.51 (br, 2H), 1.79 (m, 1H), 1.93 (br, 4H), 2.26 (t, J=7.5 Hz, 2H), 2.72 (m, 1H), 3.65-4.10 (m, 4H), 5.20-5.28 (m, 2H)

Synthesis Study According to a Formulation Described in Documents

Comparative Example 1: Synthesis of Phosphonic Acid Dimethyl Ester, Arbuzov Reaction

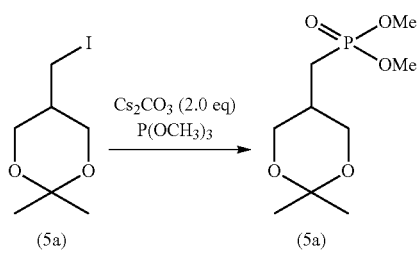

The iodine compound (5a) (15.00 g) was dissolved in 105 mL of trimethyl phosphite, followed by heating under reflux for 14 hours. Then, 210 mL of trimethyl phosphite was added again, and the mixture was heated under reflux for 6 hours. After concentration, the resulting residue was purified with silica gel chromatography (chloroform:methanol=15:1) to obtain 8.34 g of phosphonic acid dimethyl compound (6a) (yield: 60%), which contained by-products with an unknown structure.

Comparative Example 2: Synthesis of (2-methoxy-2-oxo-2λ⁵-[1,2]oxaphosphoran-4-yl)methanol, cyclization reaction

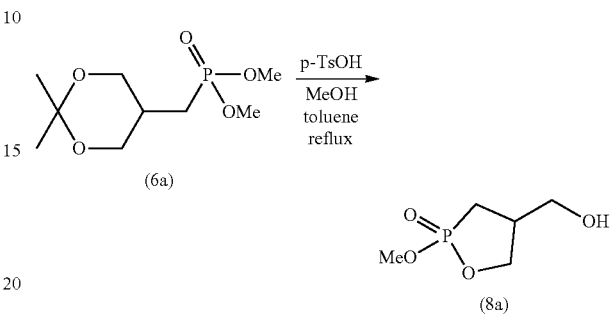

The phosphonic acid dimethyl compound (6a) (8.34 g) obtained in Comparative Example 1 was dissolved in 417 mL of toluene and 14.1 mL of methanol. Then, 1.53 g of p-toluenesulfonic acid monohydrate was added thereto, and the mixture was heated under reflux for 3 hours. Toluene and methanol were then distilled off under reduced pressure, and silica gel chromatography (chloroform:methanol=15:1) was carried out to obtain 2.44 g of cyclic phosphonic acid compound (8a) (yield: 42%).

Comparative Example 3: Synthesis of (9-octadecenoic acid-2-methoxy-2-oxo-2λ⁵-[1,2]oxaphosphoran-4-yl)methyl ester, Condensation Reaction

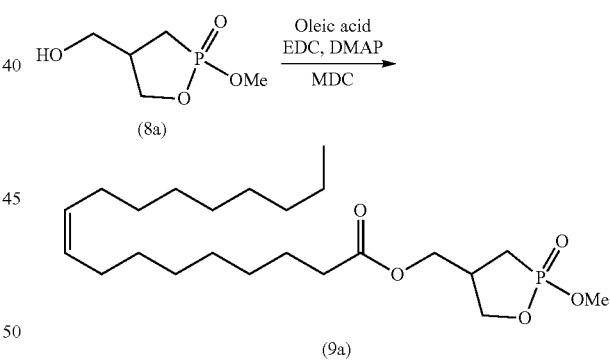

The cyclic phosphonic acid compound (8a) (2.42 g) obtained in Comparative Example 2, 4.11 g of oleic acid, and 534.0 mg of 4-dimethylaminopyridine were dissolved in 48.6 mL of dichloromethane. After the resulting mixture was ice-cooled, 3.35 g of EDC, 1.23 g of oleic acid, 2.23 g of EDC, and 808 mL of dichloromethane were added thereto, followed by stirring at room temperature for 24 hours. The resulting product was diluted with 571 mL of methanol, and 300 mL of water was added thereto. After the layers were separated, the water phase was extracted twice with 300 mL and 100 mL of ethyl acetate, the organic phases were dried over magnesium sulfate, and ethyl acetate and methanol were distilled off under reduced pressure. The resulting residue was purified with silica gel chromatography (only with ethyl acetate) to obtain 2.65 g of cyclic phosphonic acid ester compound (9a) (yield: 42%).

Comparative Example 4: Synthesis of (9-octadecenoic acid-2-methoxy-2-oxo-2λ⁵-[1,2]oxaphosphoran-4-yl)methyl Ester Proton Type, Demethylation Reaction

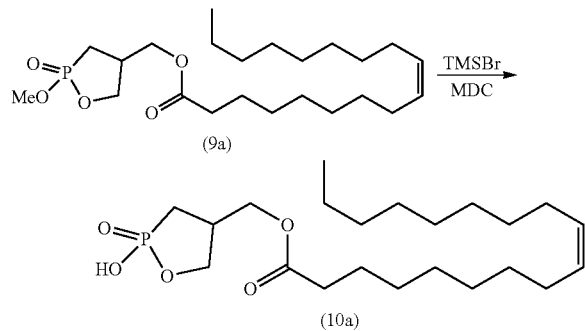

The cyclic phosphonic acid ester compound (9a) (2.51 g) synthesized in Comparative Example 3 was dissolved in 303 mL of dichloromethane. After cooling to −15° C., 2.31 mL of bromo trimethylsilane was added thereto, and the mixture was stirred at −15° C. for 4.5 hours. The reaction solution was poured into 200 mL of ice water, and extracted with 750 mL of diethyl ether. After the layers were separated, extraction was performed again twice with 200 mL of diethyl ether. The organic phases were dried over sodium sulfate, and the solvent was distilled off under reduced pressure. Thereafter, silica gel chromatography (chloroform:methanol=5:1) was carried out to obtain 367.6 mg of compound (10a: proton type of 2ccPA) (yield: 15%).

Comparative Example 5: Synthesis of (9-octadecenoic acid-2-methoxy-2-oxo-2λ⁵-[1,2]oxaphosphoran-4-yl)methyl Ester Sodium Salt

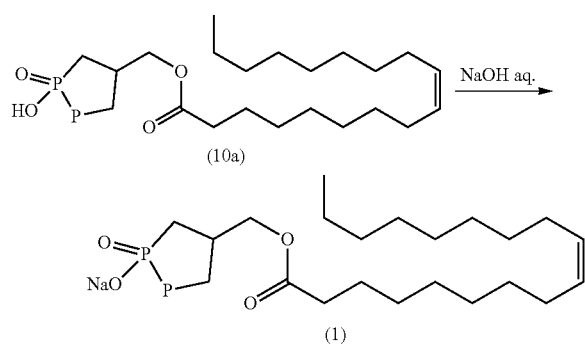

The compound (10a) obtained in Comparative Example 4 (418.6 mg) was dissolved in 30 mL of diethyl ether. Then, 20 mL of 0.05 M aqueous sodium hydroxide solution was added thereto, and the mixture was stirred. After the resulting mixture was separated into layers, the water phase was freeze-dried to obtain 250.8 mg of 2ccPA (1) (yield: 517%; purity: 67.934%).

Test Example 1: Stability Test at 35° C.

The 2ccPA crystal obtained in Example 3 (present invention), the 2ccPA obtained in Comparative Example 5 (a formula described in documents), and an amorphous of 2ccPA were individually stored at 35° C. for one month, and a stability test was performed. Table 1 below shows the results.

As the amorphous of 2ccPA above, 300 mg of 2ccPA (obtained in Example 3) dissolved in 5 mL of water and freeze-dried was used.

In the stability test, about 15 mg each of the 2ccPA crystal of the present invention, the 2ccPA of a formula described in documents, and an amorphous of 2ccPA were weighed, and individually diluted with 5 mL of acetonitrile/water (1/1). Then, 5 μL each of the diluted solutions was analyzed weekly using the LC-2010CHT (Shimazu Corporation).

TABLE 1

| Number of days | 0 | 7 | 14 | 21 | 28 | 42 | 56 |
| --- | --- | --- | --- | --- | --- | --- | --- |
| A formula described in documents | 67.934% | 66.665% | 67.517% | 62.77% | 59.841% | | |
| 2ccPA crystal of the present invention | 99.561% | 99.605% | 99.576% | 99.631% | 99.626% | 99.593% | 99.493% |
| Amorphous of 2ccPA | 99.599% | 83.363% | 45.02% | 34.738% | 27.077% | | |

As shown in the results in Table 1, the 2ccPA produced in accordance with a formula described in documents in Comparative Examples 1 to 5 had insufficient purity and were unstable. Although the amorphous of 2ccPA had satisfactory purity, decomposition proceeded each week, and the stability was unsatisfactory.

In contrast, the 2ccPA crystal obtained by the production method of the present invention had high purity and excellent stability. Even 56 days later, a purity as high as 99.493% was maintained; thus, the crystal of the present invention had excellent storage stability, compared to 2ccPA obtained by known production methods.

The invention claimed is:

1. A crystal of a cyclic phosphonic acid sodium salt (2ccPA) represented by formula (1):

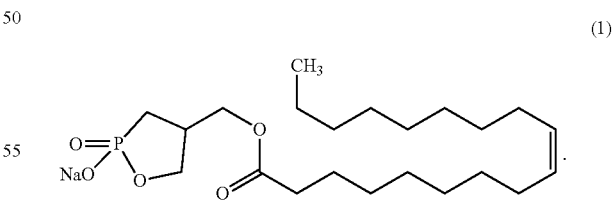

2. The crystal according to claim 1, having an X-ray powder diffraction spectrum comprising a characteristic peak expressed in degrees 2θ at 15° to 17°.

3. The crystal according to claim 1, having an X-ray powder diffraction spectrum comprising a characteristic peak expressed in degrees 2θ at 9° to 10°.

4. The crystal according to claim 1, having an X-ray powder diffraction spectrum comprising characteristic peaks expressed in degrees 2θ at 3° to 5°.

5. The crystal according to claim 1, having an X-ray powder diffraction spectrum obtained with monochromated copper radiation of λ=1.54059 Å comprising a highest intensity at lattice spacing (d) of 15.7684 to 16.1724.

6. The crystal according to claim 1, having an X-ray powder diffraction spectrum obtained with monochromated copper radiation of λ=1.54059 Å comprising a characteristic peak at lattice spacing (d) of 15.7684 to 16.1724.

7. The crystal according to claim 1, having an X-ray powder diffraction spectrum obtained with monochromated copper radiation of λ=1.54059 Å comprising characteristic peaks at the following lattice spacings (d):
15.7684 to 16.1724
9.5425 to 9.6675
4.9024 to 4.9403
4.7869 to 4.8335
4.4802 to 4.5164
4.1641 to 4.2070
3.7263 to 3.8145.

8. The crystal according to claim 1, having an X-ray powder diffraction spectrum obtained with monochromated copper radiation of λ=1.54059 Å with lattice spacing (d) satisfying any one of the requirements (a) to (y):
(a) Lattice spacing (d)
16.1724
9.6675
4.9186
4.8335
4.5164
4.1835
3.7921
(b) Lattice spacing (d)
15.9390
9.5838
4.9294
4.7972
4.4982
4.1913
3.7953
(c) Lattice spacing (d)
15.8817
9.5631
4.9186
4.7869
4.4937
4.1835
3.7794
(d) Lattice spacing (d)
15.8817
9.5631
4.9294
4.7920
4.4982
4.1874
3.8017
(e) Lattice spacing (d)
15.8817
9.5631
4.9186
4.7869
4.4937
4.1874
3.7921
(f) Lattice spacing (d)
15.8248
9.5425
4.9078
4.7920
4.4937
4.1796
3.7762
(g) Lattice spacing (d)
16.0548
9.6046
4.9294
4.8075
4.5073
4.2070
3.7857
(h) Lattice spacing (d)
15.9967
9.6046
4.9349
4.8023
4.5073
4.1913
3.8017
(i) Lattice spacing (d)
15.8817
9.5631
4.9294
4.7920
4.4982
4.1913
3.8017
(j) Lattice spacing (d)
15.9967
9.6046
4.9024
4.8075
4.5027
4.1835
3.7636
(k) Lattice spacing (d)
16.0548
9.6255
4.9403
4.8023
4.5073
4.1992
3.7985
(l) Lattice spacing (d)
16.0548
9.6255
4.9349
4.8075
4.5073
4.1952
3.7857
(m) Lattice spacing (d)
15.9390
9.5631
4.9186
4.7972
4.4982
4.1874
3.7953
(n) Lattice spacing (d)
15.939
9.5838
4.9132
4.7920
4.4937

4.1874
3.7762
(o) Lattice spacing (d)
15.9967
9.6046
4.9024
4.8075
4.4982
4.1719
3.7293
(p) Lattice spacing (d)
16.0548
9.6255
4.9349
4.8075
4.5073
4.1992
3.8145
(q) Lattice spacing (d)
15.7684
9.5425
4.8282
4.4802
4.1757
3.7263
(r) Lattice spacing (d)
15.9390
9.5838
4.9132
4.8023
4.4937
4.1641
3.7730
(s) Lattice spacing (d)
15.9390
9.5838
4.9186
4.7920
4.4937
4.1835
3.7921
(t) Lattice spacing (d)
15.9390
9.5838
4.9240
4.7920
4.4982
4.1874
3.7921
(u) Lattice spacing (d)
16.0548
9.6255
4.9186
4.7920
4.4982
4.1835
3.7985
(v) Lattice spacing (d)
16.0548
9.6255
4.9294
4.7972
4.5073
4.1874
3.7985
(w) Lattice spacing (d)
16.0548
9.6255
4.9186
4.8075
4.4982
4.1835
3.8049
(x) Lattice spacing (d)
15.9967
9.6046
4.9240
4.8023
4.4982
4.1874
3.7985
(y) Lattice spacing (d)
15.9390
9.5838
4.9186
4.7869
4.4937
4.1796
3.7985.

9. An analgesic agent comprising the crystal according to claim 1.

10. An anti-cancer agent comprising the crystal according to claim 1.

11. An osteoarthritis therapeutic agent comprising the crystal according to claim 1.

* * * * *